US011577142B2

(12) United States Patent
Howenstein et al.

(10) Patent No.: US 11,577,142 B2
(45) Date of Patent: Feb. 14, 2023

(54) SWING ANALYSIS SYSTEM THAT CALCULATES A ROTATIONAL PROFILE

(71) Applicant: Blast Motion Inc., Carlsbad, CA (US)

(72) Inventors: Jacob Howenstein, San Diego, CA (US); Bhaskar Bose, Carlsbad, CA (US)

(73) Assignee: Blast Motion Inc., San Marcos, CA (US)

( * ) Notice: Subject to any disclaimer, the term of this patent is extended or adjusted under 35 U.S.C. 154(b) by 0 days.

(21) Appl. No.: 17/359,407

(22) Filed: Jun. 25, 2021

(65) Prior Publication Data

US 2021/0331057 A1   Oct. 28, 2021

Related U.S. Application Data

(63) Continuation-in-part of application No. 17/228,635, filed on Apr. 12, 2021, which is a continuation of
(Continued)

(51) Int. Cl.
*A63B 69/36* (2006.01)
*G01C 21/16* (2006.01)
(Continued)

(52) U.S. Cl.
CPC ...... *A63B 69/3685* (2013.01); *A63B 69/3635* (2013.01); *G01C 21/00* (2013.01);
(Continued)

(58) Field of Classification Search
CPC ............ A63B 69/3685; A63B 69/3635; A63B 2069/0008; A63B 2220/18;
(Continued)

(56) References Cited

U.S. PATENT DOCUMENTS 1,712,537 A   5/1929 White
3,182,508 A   5/1965 Varju
(Continued)

FOREIGN PATENT DOCUMENTS

EP   2025369 A2   2/2009
EP   2479993   7/2012
(Continued)

OTHER PUBLICATIONS

International Search Report received in PCT/US2016/042668, dated Oct. 4, 2016, 21 pages.
(Continued)

*Primary Examiner* — Nini F Legesse
(74) *Attorney, Agent, or Firm* — Arc IP Law, PC; Joseph J. Mayo

(57) ABSTRACT

A system that measures a swing of equipment (such as a bat or golf club) with inertial sensors, and analyzes sensor data to create a rotational profile. Swing analysis may use a two-lever model, with a body lever from the center of rotation to the hands, and an equipment lever from the hands to the sweet spot of the equipment. The rotational profile may include graphs of rates of change of the angle of the body lever and of the relative angle between the body lever and the equipment lever, and a graph of the centripetal acceleration of the equipment. These three graphs may provide insight into players' relative performance. The timing and sequencing of swing stages may be analyzed by partitioning the swing into four phases: load, accelerate, peak, and transfer. Swing metrics may be calculated from the centripetal acceleration curve and the equipment/body rotation rate curves.

18 Claims, 48 Drawing Sheets

Related U.S. Application Data application No. 16/835,247, filed on Mar. 30, 2020, now Pat. No. 10,974,121, which is a continuation-in-part of application No. 16/189,889, filed on Nov. 13, 2018, now Pat. No. 10,716,989, and a continuation-in-part of application No. 16/181,955, filed on Nov. 6, 2018, now Pat. No. 10,621,425, and a continuation-in-part of application No. 16/166,490, filed on Oct. 22, 2018, now Pat. No. 10,607,349, said application No. 16/181,955 is a continuation of application No. 15/815,571, filed on Nov. 16, 2017, now Pat. No. 10,121,066, said application No. 16/189,889 is a continuation of application No. 15/628,613, filed on Jun. 20, 2017, now Pat. No. 10,124,230, said application No. 16/166,490 is a continuation of application No. 15/590,398, filed on May 9, 2017, now Pat. No. 10,109,061, said application No. 15/628,613 is a continuation-in-part of application No. 15/214,339, filed on Jul. 19, 2016, now Pat. No. 9,694,267, said application No. 15/590,398 is a continuation of application No. 15/087,776, filed on Mar. 31, 2016, now Pat. No. 9,646,199, which is a continuation-in-part of application No. 14/801,568, filed on Jul. 16, 2015, now Pat. No. 9,396,385.

(51) Int. Cl.
| | |
|---|---|
| *G01P 15/08* | (2006.01) |
| *G06K 9/00* | (2022.01) |
| *G01C 21/00* | (2006.01) |
| *G06Q 10/0639* | (2023.01) |
| *G06T 7/20* | (2017.01) |
| *G06V 40/20* | (2022.01) |
| *G16H 20/30* | (2018.01) |
| *A63B 69/00* | (2006.01) |

(52) U.S. Cl.
CPC .......... *G01C 21/16* (2013.01); *G01P 15/0888* (2013.01); *G06K 9/00523* (2013.01); *G06K 9/00536* (2013.01); *G06Q 10/0639* (2013.01); *G06T 7/20* (2013.01); *G06V 40/23* (2022.01); *A63B 2069/0008* (2013.01); *A63B 2220/18* (2013.01); *A63B 2220/833* (2013.01); *G16H 20/30* (2018.01)

(58) Field of Classification Search
CPC .......... A63B 2220/833; A63B 2220/40; G01C 21/00; G01C 21/16; G01P 15/0888; G01P 15/18; G06K 9/00523; G06K 9/00536; G06Q 10/0639; G06T 7/20; G06V 40/23; G16H 20/30
USPC .................. 473/221–223, 257, 409, 453, 454
See application file for complete search history.

(56) References Cited

U.S. PATENT DOCUMENTS

| | | |
|---|---|---|
| 3,226,704 A | 12/1965 | Petrash |
| 3,270,564 A | 9/1966 | Evans |
| 3,776,556 A | 12/1973 | McLaughlin |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,515,365 A | 5/1985 | Horikoshi et al. |
| 4,759,219 A | 7/1988 | Cobb et al. |
| 4,898,389 A | 2/1990 | Plutt |
| 4,902,014 A | 2/1990 | Bontomase et al. |
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashima et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,443,260 A | 8/1995 | Stewart et al. |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,707,299 A | 1/1998 | McKenna |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,993,333 A | 11/1999 | Heckaman |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,253,159 B1 | 6/2001 | Bett et al. |
| 6,254,492 B1 | 7/2001 | Taggett |
| 6,266,623 B1 | 7/2001 | Vock et al. |
| 6,292,130 B1 | 9/2001 | Cavallaro et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Antilla |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |

(56) References Cited

U.S. PATENT DOCUMENTS

| | | |
|---|---|---|
| 7,175,177 B2 | 2/2007 | Meifu et al. |
| 7,205,894 B1 | 4/2007 | Savage |
| 7,212,943 B2 | 5/2007 | Aoshima et al. |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | Mcnitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,731,598 B1 | 6/2010 | Kim et al. |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk |
| 8,352,211 B2 | 1/2013 | Vock et al. |
| 8,400,548 B2 | 3/2013 | Bilbrey et al. |
| 8,425,292 B2 | 4/2013 | Lui et al. |
| 8,477,027 B2 | 7/2013 | Givens |
| 8,527,228 B2 | 9/2013 | Panagas |
| 8,565,483 B2 | 10/2013 | Nakaoka |
| 8,589,114 B2 | 11/2013 | Papadourakis |
| 8,696,482 B1 * | 4/2014 | Pedenko ............ A63B 24/0003 473/223 |
| 8,723,986 B1 | 5/2014 | Merrill |
| 8,725,452 B2 | 5/2014 | Han |
| 8,764,576 B2 | 7/2014 | Takasugi |
| 8,781,610 B2 | 7/2014 | Han |
| 8,831,905 B2 | 9/2014 | Papadourakis |
| 8,876,621 B2 | 11/2014 | Shibuya |
| 8,888,603 B2 | 11/2014 | Sato et al. |
| 8,905,856 B2 | 12/2014 | Parke et al. |
| 8,929,709 B2 | 1/2015 | Lokshin |
| 8,944,932 B2 | 2/2015 | Sato et al. |
| 8,944,939 B2 | 2/2015 | Clark et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,032,794 B2 | 5/2015 | Perkins et al. |
| 9,060,682 B2 | 6/2015 | Lokshin |
| 9,146,134 B2 | 9/2015 | Lokshin et al. |
| 9,500,464 B2 | 11/2016 | Coza |
| 9,646,199 B2 | 5/2017 | Bose et al. |
| 9,656,122 B2 | 5/2017 | Papadourakis |
| 10,124,230 B2 | 5/2018 | Thronbrue et al. |
| 10,456,653 B2 * | 10/2019 | Thornbrue ......... G06Q 10/0639 |
| 10,460,157 B2 | 10/2019 | Matsunaga et al. |
| 10,716,989 B2 * | 7/2020 | Thornbrue ......... G06K 9/00523 |
| 10,974,121 B2 * | 4/2021 | Thornbrue ............ G01C 21/00 |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty |
| 2003/0074659 A1 | 4/2003 | Louzoun |
| 2003/0109322 A1 | 6/2003 | Funk et al. |
| 2003/0163287 A1 | 8/2003 | Vock et al. |
| 2003/0191547 A1 | 10/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 * | 4/2006 | Eyestone ............ A63B 69/3632 473/219 |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1 | 8/2006 | Hunter et al. |
| 2006/0199659 A1 | 9/2006 | Caldwell |
| 2006/0247070 A1 | 11/2006 | Funk et al. |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2006/0293112 A1 | 12/2006 | Yi |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1 | 11/2007 | Bentley |
| 2007/0298896 A1 | 12/2007 | Nusbaum |
| 2008/0027502 A1 | 1/2008 | Ransom |
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0182685 A1 | 7/2008 | Marty et al. |
| 2008/0190202 A1 | 8/2008 | Kulach et al. |

(56) References Cited

U.S. PATENT DOCUMENTS

| | | |
|---|---|---|
| 2008/0211768 A1 | 9/2008 | Breen et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0144785 A1 | 6/2009 | Walker et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0144457 A1 | 6/2010 | Kim |
| 2010/0178994 A1 | 7/2010 | Do et al. |
| 2010/0201512 A1 | 8/2010 | Stirling et al. |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0309097 A1 | 12/2010 | Raviv et al. |
| 2010/0323794 A1 | 12/2010 | Su |
| 2011/0004871 A1 | 1/2011 | Liu |
| 2011/0029235 A1 | 2/2011 | Berry |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0126184 A1 | 5/2011 | Lisboa |
| 2011/0165998 A1 | 7/2011 | Lau et al. |
| 2011/0195780 A1 | 8/2011 | Lu |
| 2011/0225178 A1 | 9/2011 | Ingrassia et al. |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2011/0238308 A1 | 9/2011 | Miller et al. |
| 2012/0004034 A1 | 1/2012 | Pope et al. |
| 2012/0023354 A1 | 1/2012 | Chino |
| 2012/0052972 A1 | 3/2012 | Bentley |
| 2012/0088544 A1 | 4/2012 | Bentley et al. |
| 2012/0115626 A1 | 5/2012 | Davenport |
| 2012/0115682 A1 | 5/2012 | Homsi |
| 2012/0116548 A1 | 5/2012 | Goree et al. |
| 2012/0120572 A1 | 5/2012 | Bentley |
| 2012/0142415 A1 | 6/2012 | Lindsay |
| 2012/0157241 A1 | 6/2012 | Nomura et al. |
| 2012/0179418 A1 | 7/2012 | Takasugi et al. |
| 2012/0179742 A1 | 7/2012 | Acharya et al. |
| 2012/0191405 A1 | 7/2012 | Molyneux et al. |
| 2012/0295726 A1 | 11/2012 | Cherbini |
| 2012/0316004 A1 | 12/2012 | Shibuya |
| 2013/0029791 A1 | 1/2013 | Rose et al. |
| 2013/0095924 A1 | 4/2013 | Geisner et al. |
| 2013/0095941 A1 | 4/2013 | Bentley et al. |
| 2013/0110415 A1 | 5/2013 | Davis et al. |
| 2013/0128022 A1 | 5/2013 | Bose et al. |
| 2013/0173212 A1 | 7/2013 | Saiki et al. |
| 2013/0178304 A1 | 7/2013 | Chan |
| 2013/0191063 A1 | 7/2013 | Nomura |
| 2013/0225309 A1 | 8/2013 | Bentley et al. |
| 2013/0245966 A1 | 9/2013 | Burroughs et al. |
| 2013/0267335 A1 | 10/2013 | Boyd et al. |
| 2013/0271602 A1 | 10/2013 | Bentley et al. |
| 2013/0281223 A1 | 10/2013 | Lee et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0343729 A1 | 12/2013 | Rav-Acha et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1 | 5/2014 | Shibuya et al. |
| 2014/0156214 A1 | 6/2014 | Nomura |
| 2014/0172873 A1 | 6/2014 | Varoglu et al. |
| 2014/0200092 A1 | 7/2014 | Parke et al. |
| 2014/0200094 A1* | 7/2014 | Parke ................ G06V 40/23 473/409 |
| 2014/0206481 A1 | 7/2014 | Zuger |
| 2014/0213382 A1 | 7/2014 | Kang et al. |
| 2014/0229135 A1 | 8/2014 | Nomura |
| 2014/0229138 A1 | 8/2014 | Goree et al. |
| 2014/0257743 A1 | 9/2014 | Lokshin et al. |
| 2014/0257744 A1 | 9/2014 | Lokshin et al. |
| 2014/0334796 A1 | 11/2014 | Galant et al. |
| 2014/0376876 A1 | 12/2014 | Bentley et al. |
| 2014/0378239 A1 | 12/2014 | Sato et al. |
| 2014/0379293 A1 | 12/2014 | Sato |
| 2014/0379294 A1 | 12/2014 | Shibuya et al. |
| 2014/0379295 A1 | 12/2014 | Sato et al. |
| 2015/0007658 A1 | 1/2015 | Ishikawa et al. |
| 2015/0012240 A1 | 1/2015 | Sato |
| 2015/0042481 A1 | 2/2015 | Nomura |
| 2015/0098688 A1 | 4/2015 | Lokshin |
| 2015/0124048 A1 | 5/2015 | King |
| 2015/0131845 A1 | 5/2015 | Forouhar et al. |
| 2015/0348591 A1 | 5/2015 | King |
| 2015/0256689 A1 | 9/2015 | Erkkila et al. |
| 2015/0258402 A1 | 9/2015 | Bynum |
| 2016/0129332 A1* | 5/2016 | Davenport ......... A63B 53/0466 473/223 |
| 2016/0166902 A1* | 6/2016 | Day ................. A63B 60/16 473/223 |
| 2016/0175673 A1* | 6/2016 | Shibuya ............ G06Q 10/0639 473/223 |
| 2017/0061817 A1 | 3/2017 | Mettler |
| 2017/0157484 A1 | 6/2017 | Altshuler et al. |
| 2018/0021648 A1 | 1/2018 | Thornbrue et al. |
| 2018/0021653 A1 | 1/2018 | Thornbrue et al. |
| 2018/0070056 A1 | 3/2018 | DeAngelis et al. |

FOREIGN PATENT DOCUMENTS

| | | |
|---|---|---|
| EP | 2652738 | 10/2013 |
| EP | 2781240 | 9/2014 |
| JP | 2002210055 A | 7/2002 |
| JP | 2004207985 | 7/2004 |
| JP | 2005176030 | 6/2005 |
| JP | 2011000367 | 1/2011 |
| JP | 2012196241 | 10/2012 |

(56) References Cited

FOREIGN PATENT DOCUMENTS

| | | |
|---|---|---|
| JP | 2013188426 | 9/2013 |
| KR | 10-20030085275 | 11/2003 |
| KR | 10-20060041060 | 5/2006 |
| KR | 10-20070119018 | 12/2007 |
| KR | 10-20100074068 | 7/2010 |
| KR | 101079319 | 6/2011 |
| KR | 10-20100020131 | 9/2011 |
| WO | 1994027683 | 12/1994 |
| WO | 2007130057 A1 | 11/2007 |
| WO | 2009056688 A1 | 5/2009 |
| WO | 2011057194 | 5/2011 |
| WO | 2014085744 A1 | 6/2014 |

OTHER PUBLICATIONS

International Search Report received in PCT/US2016/042671, dated Oct. 13, 2016, 17 pages.
International Search Report and Written Opinion received in PCT/US2016/042676, dated Oct. 24, 2016 (12 pages).
International Preliminary Report on Patentability received in PCT/US2015/026917, dated Nov. 3, 2016 (5 pages).
International Search Report received for PCT Application No. PCT/US2012/065716, dated Jan. 3, 2013, 10 pages.
MyCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, dated Mar. 6, 2012, 8 pages.
International Search Report received for PCT Application No. PCT/US2011/049461, dated Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.
International Search Report for PCT Application No. PCT/US2013/021999, dated Apr. 30, 2013, 8 pages.
International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
MiCoach Pacer User Manual, 31 pages, (2009).
Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
TRACE—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
PocketPro Golf Designs, PocketPro Full Swing Analysis in Your Pocket, www.PocketPro.org, (2011).
Clemson University, Golf Shot Tutorial, http://www.webnucleo.org/home/online_tools/newton/0.4/html/about_this_tool/tutorials/golf_1.shp.cgi, retrieved on Nov. 10, 2011.
MiCoach SPEED_CELL TM, User Manual, 23 pages, (2011).
Nike+iPod, User Guide, 32 pages (2010).
SureShotGPS SS9000X, Intelligent Touch, Instruction Manual, 25 page, 2011.
Activereplay, "TRACE—The Most Advanced Activity Monitor for Action Sports", http://www.kickstarter.com/projects/activereplay/trace-the-most-advanced-activity-monitor-for-actio, 13 pages, Oct. 1, 2013.
ZEPP Golfsense@Launch2011, https://www.youtube.com/watch?v=VnOcu8szilk (video), Mar. 14, 2011.
Epson US Newsroom, "Epson America Enters Sports Wearables Market with Introduction of M-Tracer MT500GII Golf Swing Analyzer", www.news.epson.com, Jan. 5, 2015, 4 pages.
International Search Report and Written Opinion dated Dec. 22, 2015 received in PCTUS1561695, 7 pages.
Search Report Received in PCT2013021999 dated Jan. 21, 2016.
Patent Examination Report received in Australia Application No. 2011313952, dated Mar. 15, 2016, 5 pages.
"About Banjo" webpages retrieved from internet, dated 2015.
International Search Report and Written Opinion mailed in PCTUS1642674 dated Aug. 12, 2016, 9 pages.
International Preliminary Report on Patentability in PCTUS2015061695, dated Jun. 1, 2017, 5 pages.
European Search Report received in PCTUS2015026896 dated May 11, 2017, 13 pages.
International Search Report and Written Opinion received in PCT/US2017/52114, dated Oct. 3, 9 pages.
International Search Report and Written Opinion Received in PCT/US2017/37987, dated Nov. 9, 2017, 12 pages.
Supplementary Extended European Search Report received in 11820763.8 dated Nov. 13, 2017, 16 pages.
Supplementary Extended European Search Report received in 11833159.4 dated Nov. 6, 2017, 14 pages.
Supplementary Partial European Search Report received from EP Application Serial No. 11820763.8, dated Aug. 8, 2017, 15 pages.
Supplementary Partial European Search Report received from EP Application Serial No. 11833159.4, dated Aug. 8, 2017, 15 pages.
Supplemental Search Report Received from EP Application Serial No. 16825295.5, dated Jun. 6, 2019, 7 pages.
David E. Culler, et al., "Smart Sensors to Network the World", published in Scientific American Magazine, No. 06/2004, dated Jun. 1, 2004, pp. 85-91.
International Search Report and Written Opinion received in PCT/US2017/039209, dated Aug. 24, 2017, 7 pages.
*Zepp Labs, Inc.* v. *Blast Motion, Inc.* Petition for Inter Partes Review of U.S. Pat. No. 8,903,521 filed on Feb. 24, 2016, as IPR2016-00672, and accompanying Declaration of Dr. Steven M. Nesbit.
*Zepp Labs, Inc.* v. *Blast Motion, Inc.* Petition for Inter Partes Review of U.S. Pat. No. 9,039,527 filed on Feb. 24, 2016, as IPR2016-00674, and accompanying Declaration of Dr. Steven M. Nesbit.
*Zepp Labs, Inc.* v. *Blast Motion, Inc.* Petition for Inter Partes Review of U.S. Pat. No. 8,941,723 filed on Feb. 24, 2016, as IPR2016-00675, and accompanying Declaration of Dr. Steven M. Nesbit.
*Zepp Labs, Inc.* v. *Blast Motion, Inc.* Petition for Inter Partes Review of U.S. Pat. No. 8,905,855 filed on Feb. 24, 2016, as IPR2016-00676, and accompanying Declaration of Dr. Steven M. Nesbit.
*Zepp Labs, Inc.* v. *Blast Motion, Inc.* Petition for Inter Partes Review of U.S. Pat. No. 8,944,928 filed on Feb. 24, 2016, as IPR2016-00677, and accompanying Declaration of Dr. Steven M. Nesbit.

(56) References Cited

OTHER PUBLICATIONS

Chris Otto, et al., "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", www.electronicdesign.com/communications/wireless-sensor-architecture-uses-bluetooth-standard, Aug. 7, 2000, 5 pages.
Don Tuite, "Motion-Sensing MEMS Gyros and Accelerometers are Everywhere", www.electronicdesign.com/print/analog/motion-sensing-mems-gyros-and-accelerometers-are-everywhere, Jul. 9, 2009, 6 pages.
InvenSense News Release, "InvenSense Unveils World's 1st IMU Solution for Consumer Applications", ir.invensense.com, 2016, 2 Pages.
Dean Takahashi, "Facebook, Twitter, Last.fm coming to Xbox Live this Fall", Jun. 1, 2009, Webpage printout, 5 pages.
The iClub System, Products pages, www.iclub.net, 2001-2005, 5 pages.
Websters New College Dictionary, Definition of "Virtual Reality", Third Edition, 2005, 3 Pages.
SmartSwing, "SmartSwing Introduces Affordable Intelligent Golf Club", www.smartswinggolf.com , Jan. 2006, 2 pages.
Henrick Arfwedson, et al., "Ericsson's Bluetooth modules", Ericsson Review No. 4, 1999, 8 pages.
ZigBees, "Zigbee information", www.zigbees.com , 2015, 4 pages.
SolidState Technology, "MEMS enable smart golf clubs", www.electroiq.com , 2005, 3 pages.
IGN, "Japanese WII Price Release Date Revealed", www.ign.com , 2006, 1 page.
First Annual Better Golf Through Technology Conference 2006 webpage, www.bettergolfthroughtechnology.com , Massachusetts Institute of Technology, Cambridge Massachusetts, Feb. 2006, 1 page.
Concept2rowing, "Training" web content, www.concept2.com , 2009, 1 page.
Expresso, Products pages, www.expresso.com/products , 2009, 2 pages.
Manish Kalia, et al., "Efficient Policies for Increasing Capacity in Bluetooth: An Indoor Pico-Cellular Wireless System", IBM India Research Laboratory, Indian Institute of Technology, 2000, 5 pages.
R. Rao, et al., "Demand-Based Bluetooth Scheduling", Pennsylvania State University, 2001, 13 pages.
Supplementary Extended European Search Report received in 15782595.1 dated Nov. 27, 2017, 5 pages.
Supplementary European Search Report received in 15860384.5 dated Jun. 21, 2018, 9 pages.
International Search Report and Written Opinion received in PCT/US18033757, dated Aug. 31, 2018, 8 pages.
International Preliminary Report on Patentability received in PCT/US2017/037987, dated Dec. 27, 2018, 11 pages.
International Preliminary Report on Patentability received in PCT/US2018/033757, dated Dec. 5, 2019, 6 pages.
Extended European Search Report received in 17851741.3, dated Nov. 12, 2019, 8 pages.

\* cited by examiner

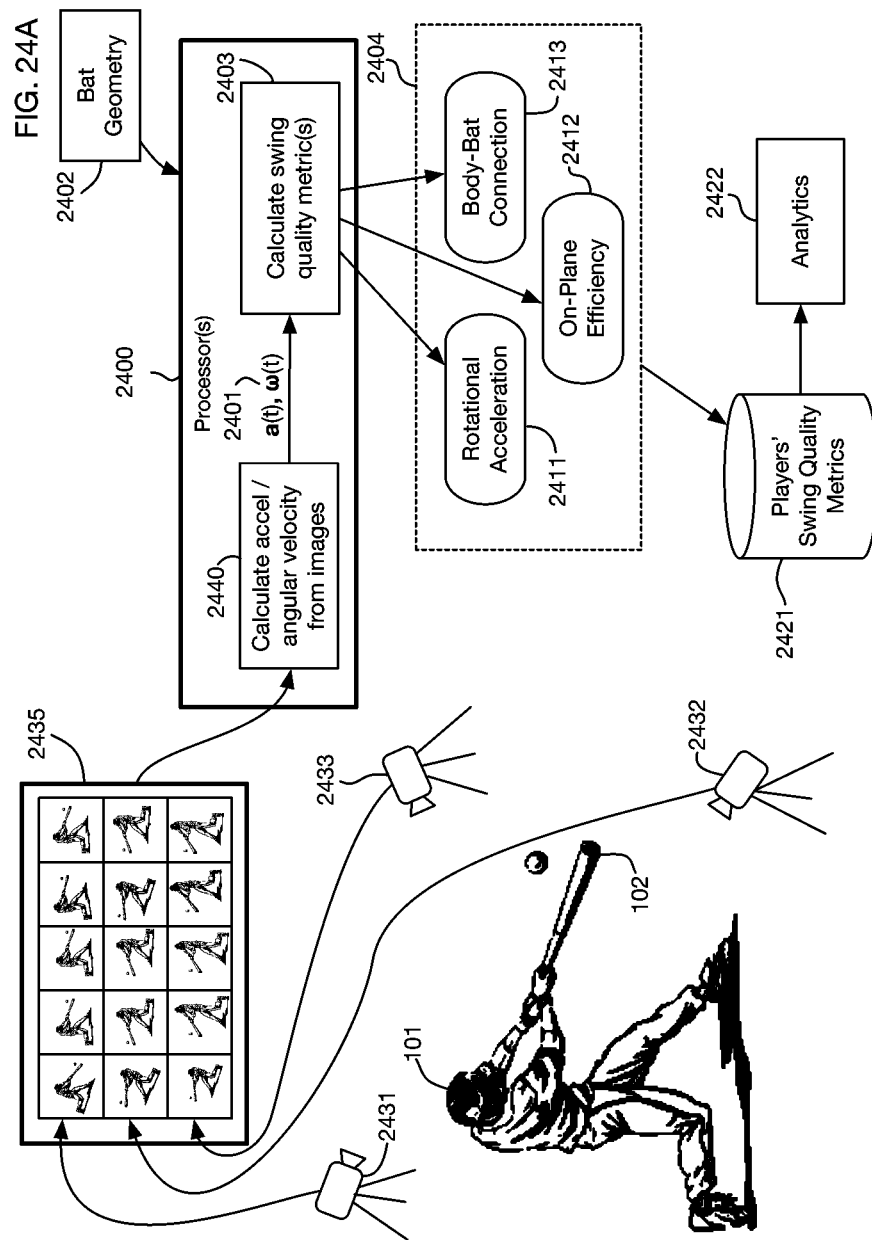

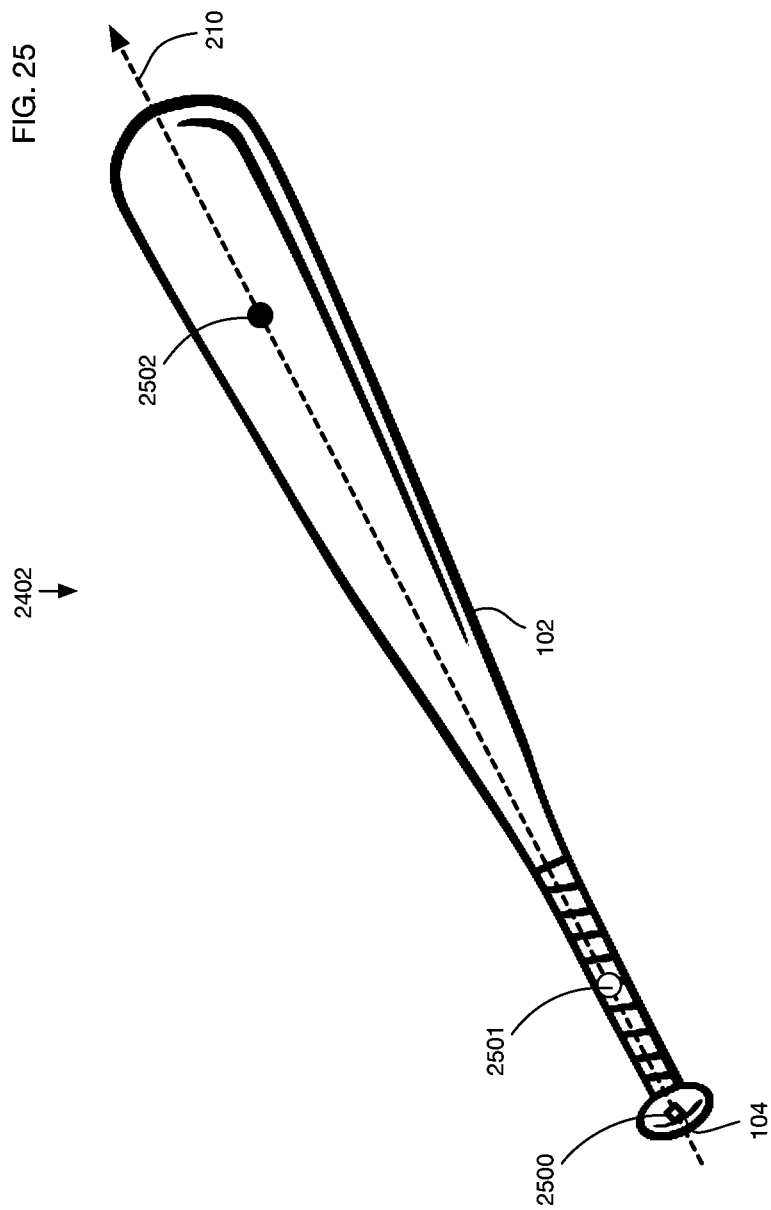

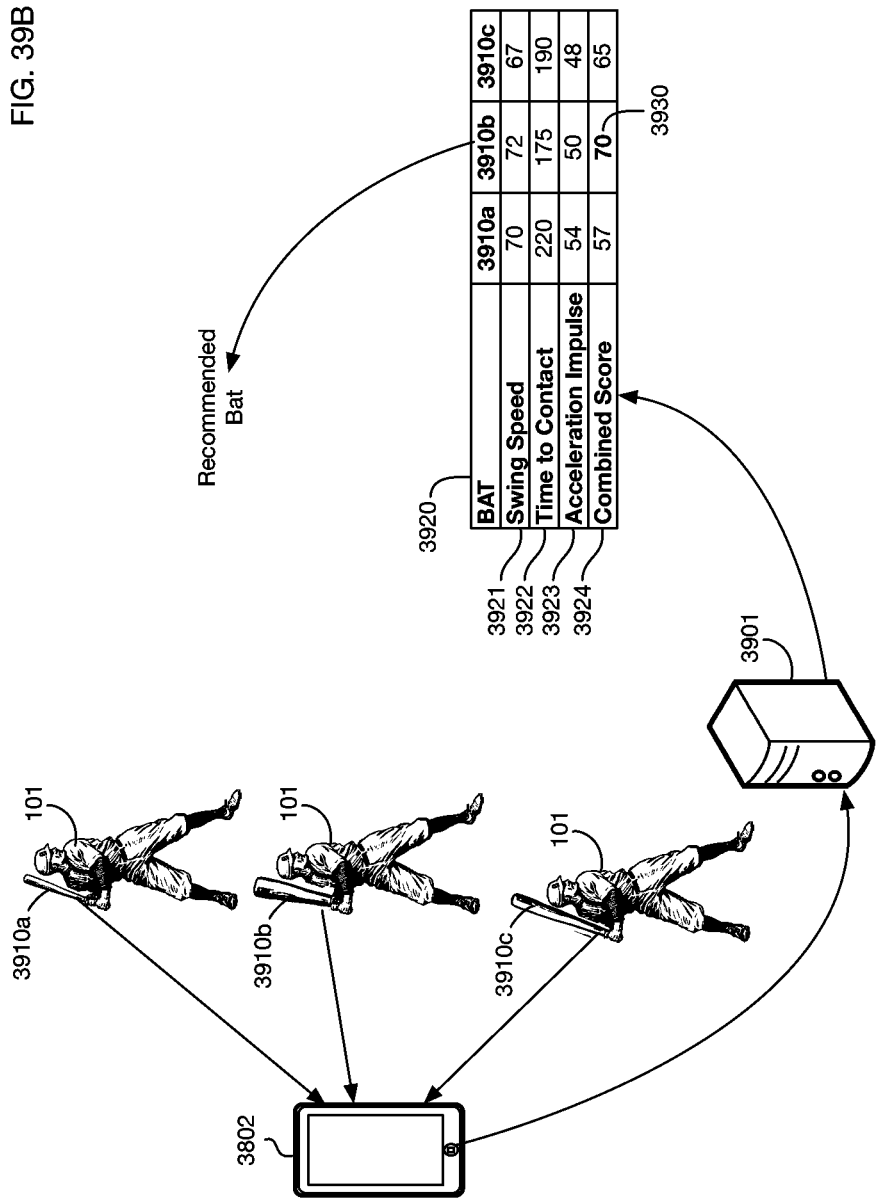

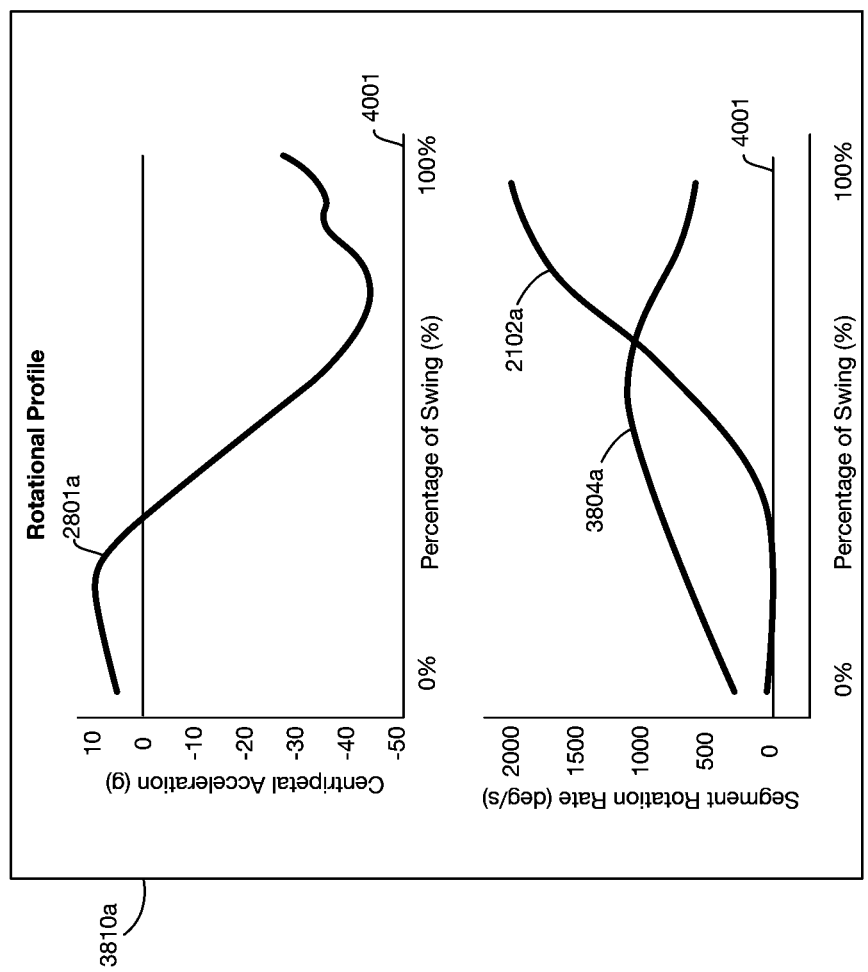

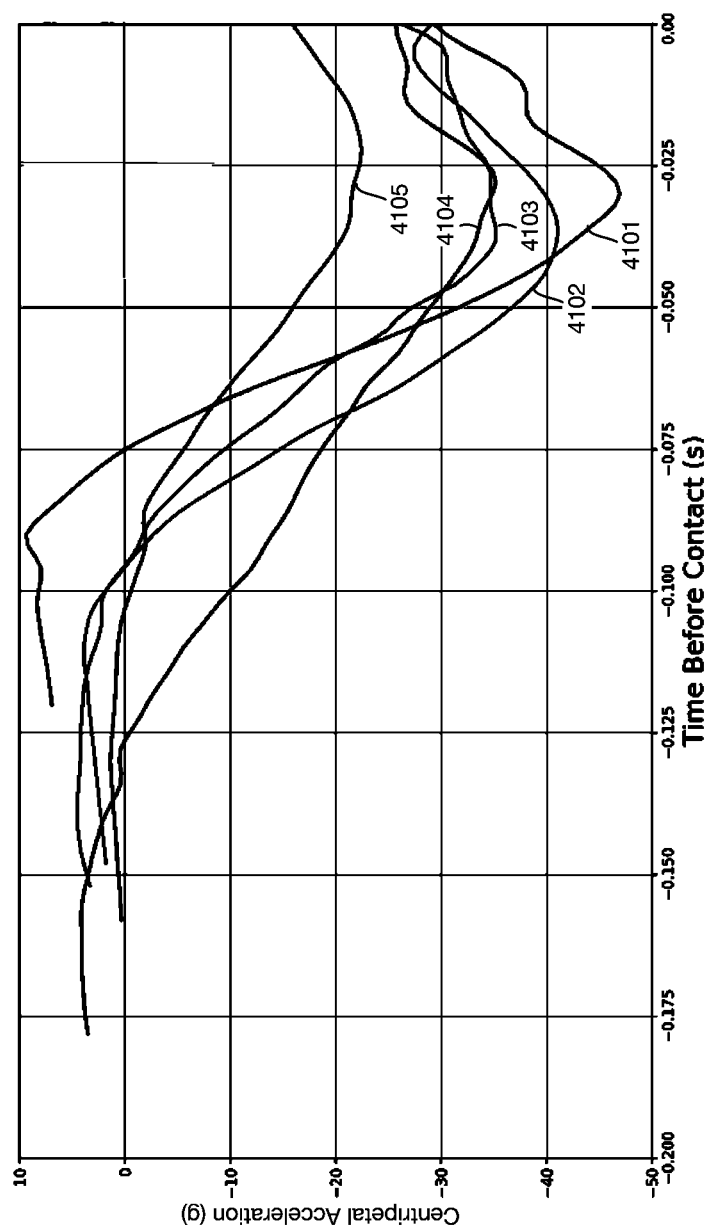

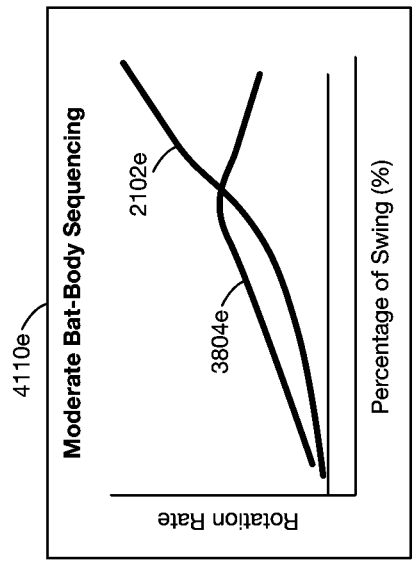
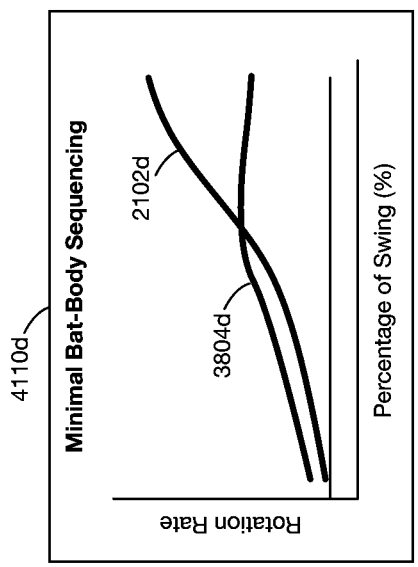
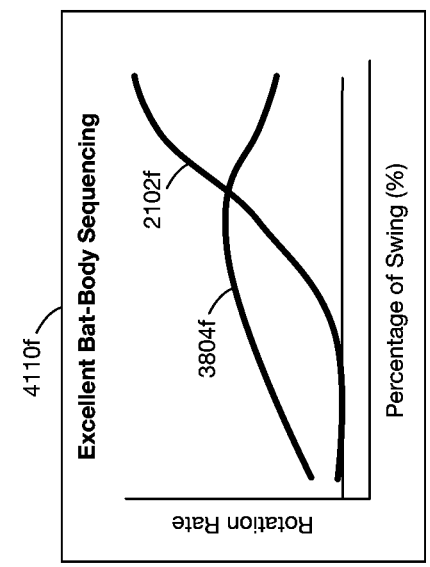
FIG. 41B

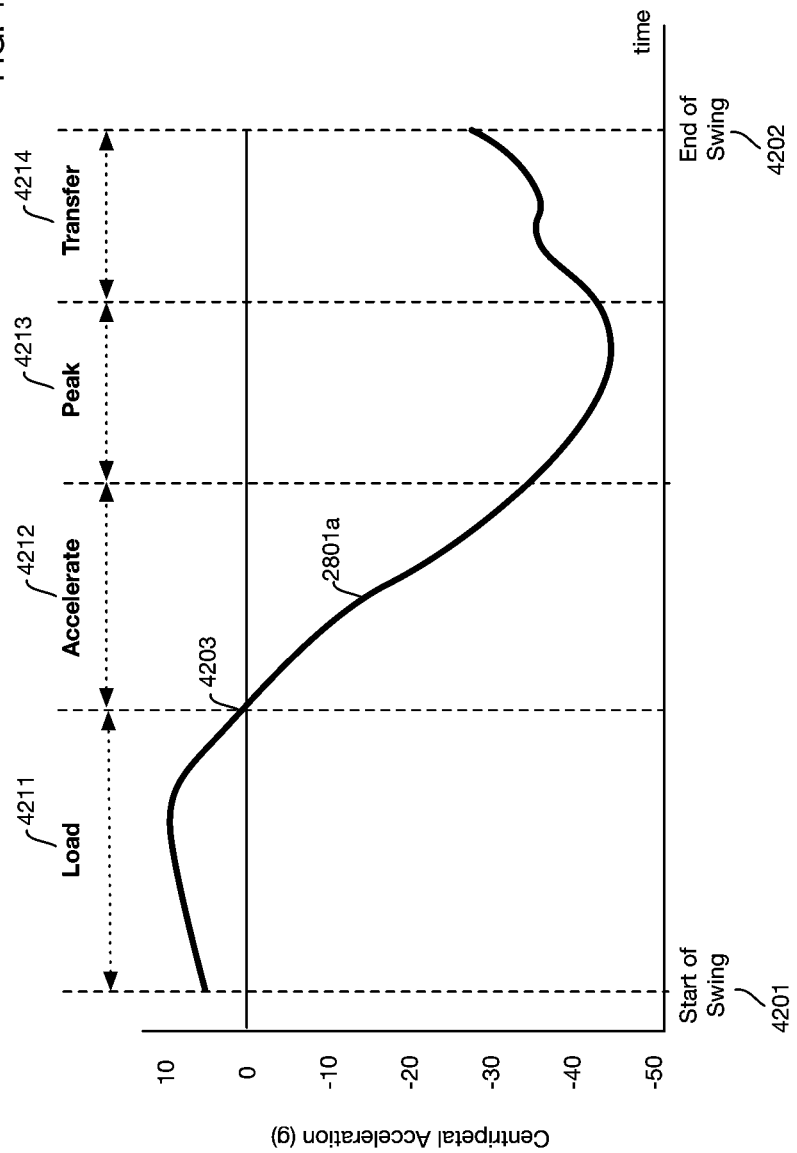

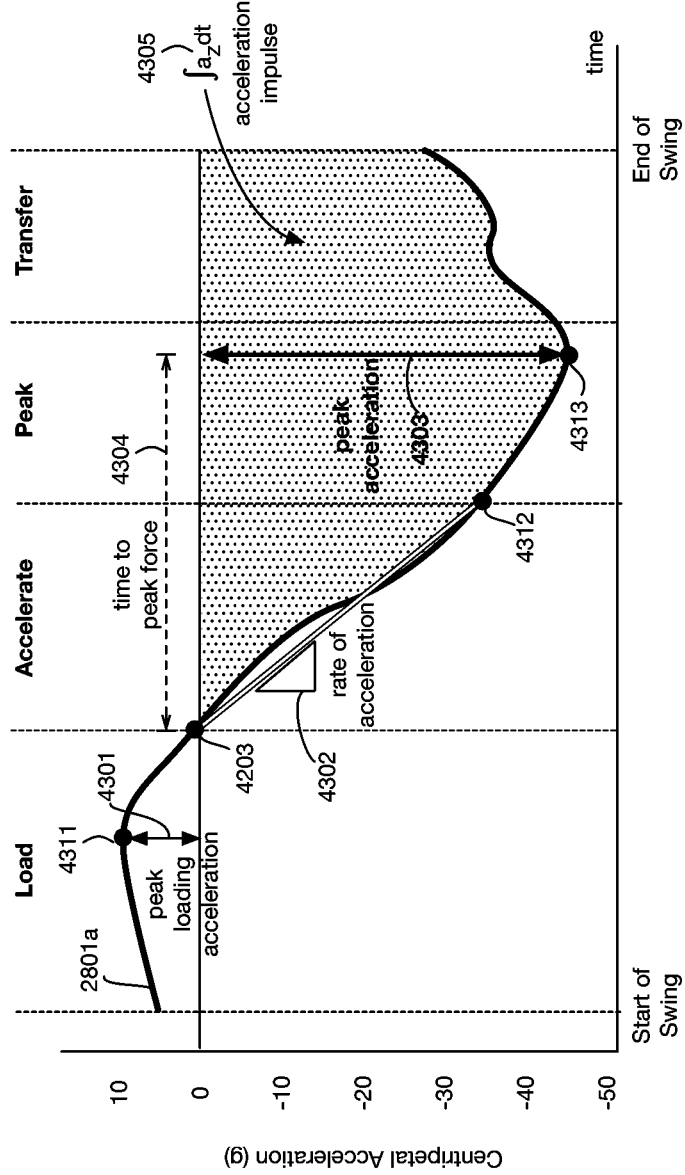

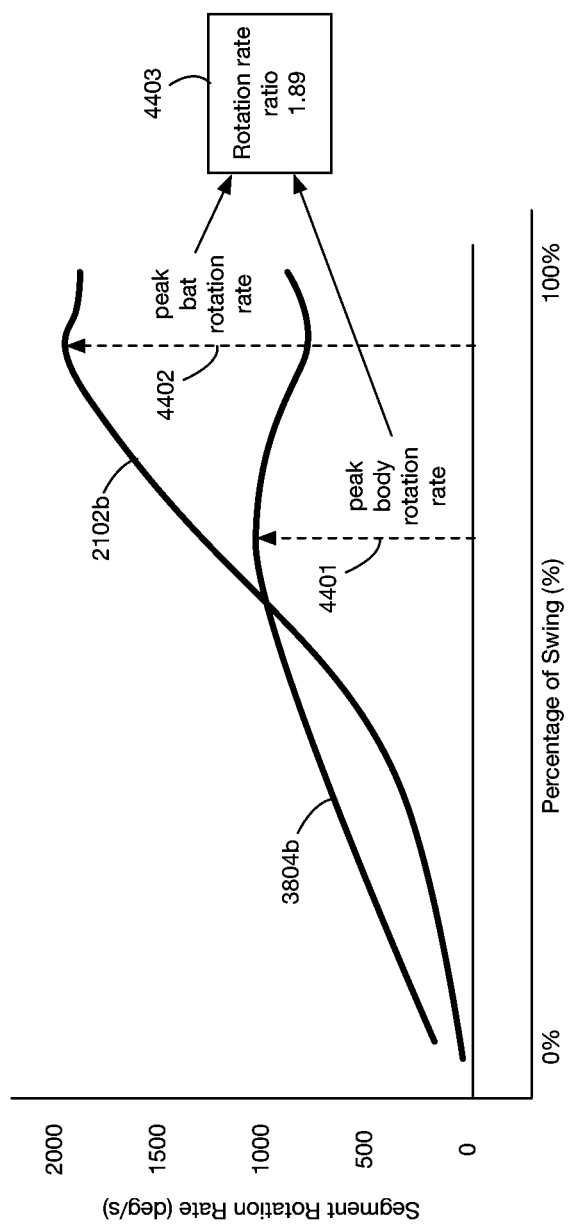

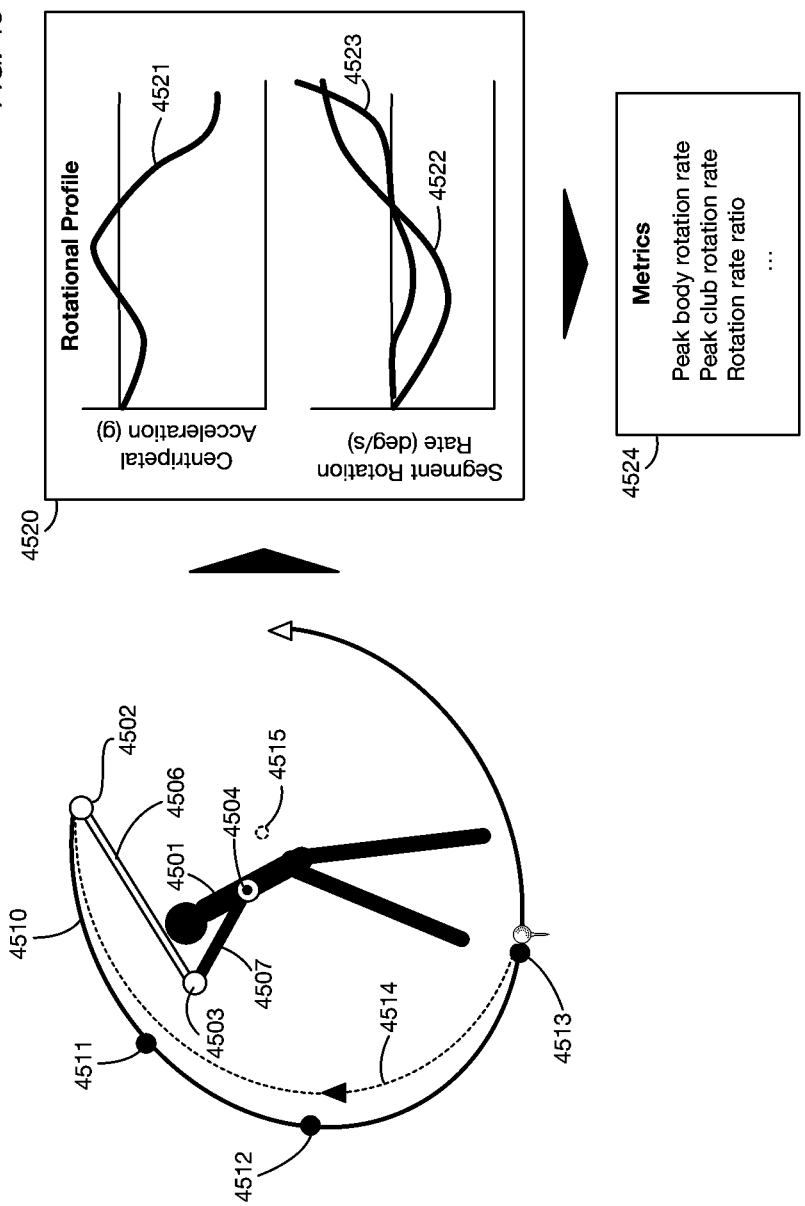

SWING ANALYSIS SYSTEM THAT CALCULATES A ROTATIONAL PROFILE

This application is a continuation-in-part of U.S. Utility patent application Ser. No. 17/228,635, filed 12 Apr. 2021, which is a continuation of U.S. Utility patent application Ser. No. 16/835,247, filed 30 Mar. 2020, issued as U.S. Pat. No. 10,974,121 on 13 Apr. 2021, which is a continuation-in-part U.S. Utility patent application Ser. No. 16/189,889, filed 13 Nov. 2018, which is a continuation of U.S. Utility patent application Ser. No. 15/628,613, filed 20 Jun. 2017, issued as U.S. Pat. No. 10,124,230, which is a continuation-in-part of U.S. Utility patent application Ser. No. 15/214,339, filed 19 Jul. 2016, issued as U.S. Pat. No. 9,694,267, the specifications of which are hereby incorporated herein by reference.

This application is also a continuation-in-part of U.S. Utility patent application Ser. No. 17/228,635, filed 12 Apr. 2021, which is a continuation of U.S. Utility patent application Ser. No. 16/835,247, filed 30 Mar. 2020, issued as U.S. Pat. No. 10,974,121 on 13 Apr. 2021, which is also a continuation-in-part of U.S. Utility patent application Ser. No. 16/166,490, filed 22 Oct. 2018, which is a continuation of U.S. Utility patent application Ser. No. 15/590,398, filed 9 May 2017, issued as U.S. Pat. No. 10,109,061 which is a continuation of U.S. Utility patent application Ser. No. 15/087,776, filed 31 Mar. 2016, issued as U.S. Pat. No. 9,646,199, which is a continuation in part of U.S. Utility patent application Ser. No. 14/801,568, filed 16 Jul. 2015, issued as U.S. Pat. No. 9,396,385, the specifications of which are hereby incorporated herein by reference.

This application is also a continuation-in-part of U.S. Utility patent application Ser. No. 17/228,635, filed 12 Apr. 2021, which is a continuation of U.S. Utility patent application Ser. No. 16/835,247, filed 30 Mar. 2020, issued as U.S. Pat. No. 10,974,121 on 13 Apr. 2021, which is also a continuation-in-part U.S. Utility patent application Ser. No. 16/181,955, filed 6 Nov. 2018, which is a continuation of U.S. Utility patent application Ser. No. 15/815,571, filed 16 Nov. 2017, issued as U.S. Pat. No. 10,121,066, the specifications of which are hereby incorporated herein by reference.

BACKGROUND OF THE INVENTION

Field of the Invention

One or more embodiments setting forth the ideas described throughout this disclosure pertain to the field of motion capture sensors and analysis of motion capture data. More particularly, but not by way of limitation, one or more aspects of the invention enable a swing analysis system that calculates a rotational profile.

Description of the Related Art

Methods for analyzing swings of a piece of equipment, such as a golf club, tennis racquet or baseball swings for example include video capture systems that record high speed video of a swing and that analyze the motion of the piece of equipment, club, racquet or bat, etc., and the player from the video. These systems are typically expensive and complex, and they are not portable. Another method is to attach a motion sensor to the piece of equipment, e.g., a bat, etc., and to analyze motion data captured by the sensor during the swing. A significant challenge for these sensor based solutions is interpretation of the sensor data. In particular, sensors typically capture data in a local reference frame defined by the sensor geometry. This sensor reference frame moves and rotates constantly throughout a swing. For example, for a baseball bat, this challenge is more complex since the bat has rotational symmetry around its long axis; thus the batter can hold the bat in multiple orientations while swinging, which changes the sensor data. This applies to other sports that involve a swing of a piece of equipment and any discussion oriented towards a bat herein is not limiting, and can be applied to any other type of equipment that involves a swing as well. There are no known methods that transform swing sensor data from a sensor based reference frame to a meaningful reference frame that is insensitive to these changes in orientation. Existing methods emphasize vector magnitudes (such as total swing speed) in defining swing metrics because these magnitudes are invariant to rotations in the sensor reference frame. However, individual components of sensor measurements along carefully chosen transformed axes provide more detailed and more physically meaningful information.

In baseball and related sports, the trajectory of specific point on the bat or other piece of equipment, for example the sweet spot, is of particular importance since this is the optimum location on the bat for striking the ball. There are no known methods that combine analysis of the sweet spot trajectory with a swing plane reference frame.

Another limitation of existing methods for analyzing swings is that the quantities measured and reported cannot be easily correlated to swing mechanics or to the factors that make for efficient and effective swings.

For at least the limitations described above there is a need for a swing analysis system that calculates a rotational profile.

BRIEF SUMMARY OF THE INVENTION

Embodiments of the invention enable a system to analyze a swing of a piece of equipment, for example a baseball bat, tennis racquet, or golf club, etc., by transforming sensor data captured during the swing to a reference frame that reflects the physics and geometry of the swing itself. This reference frame is called a swing plane reference frame. Metrics defined with respect to the swing plane reference frame provide a detailed characterization of a swing; these metrics can be compared across swings to analyze the factors that affect swing performance. For simplicity, examples directed at baseball bat swings are detailed herein, however, the exemplary embodiments described herein may also be applied to any other piece of equipment that involves a swing, including but not limited to a golf club, tennis racquet, etc.

One or more embodiments of the invention may obtain sensor data from a sensor coupled to a bat while the bat is swung to hit or otherwise contact a ball. The bat may be for example, without limitation, a baseball bat, a softball bat, or a cricket bat. The sensor may for example be an inertial motion sensor that includes any or all of a three axis accelerometer, a three axis gyroscope, and a three axis magnetometer. The sensor may be a compound sensor that incorporates multiple individual sensors of any types. A compound sensor may include multiple sensors at different locations on the bat; for example, without limitation, some sensors may be located on the knob of the bat, and other sensors may be located at the tip of the bat. Sensor data may be collected throughout the swing, for example at a rate of 10 Hz, 100 Hz, 1000 Hz, or more. The sensor data may be analyzed to determine the time of impact between the bat and a ball. For example, accelerometer data, i.e., or acceleration data, may detect the shock of the impact. A bat trajectory may be calculated from the sensor data. The trajectory may include motion data samples at multiple points in time throughout the swing; each motion data sample may describe one or more of the bat's position, orientation, velocity, angular velocity, acceleration, or angular acceleration at a point in time.

Analysis of the bat trajectory may include calculating an impact velocity vector for the velocity of the bat at the time of impact with the ball. Using the impact velocity vector, a reference frame called the swing plane reference frame may be defined for the swing. The swing plane reference frame may be formed from three axes: a first axis may be the longitudinal axis of the bat; a second axis may be the impact velocity vector; and a third axis may be orthogonal to the swing plane spanned by the first (bat) axis and the second (impact velocity) axis. The angular velocity vector of the bat, which is the rotational axis that is perpendicular to the bat's instantaneous plane of rotation, may also be used to define or calculate one or more of the axes of the swing plane reference frame. The bat trajectory may then be transformed to the swing plane reference frame for further analysis. This analysis may include creating one or more swing metrics from the transformed bat trajectory.

Illustrative metrics that may be defined using the transformed bat trajectory include the following: Swing plane speed at any point in time during the swing may be defined as an instantaneous rotational speed of the bat trajectory projected onto the swing plane. In one or more embodiments, this swing plane speed may be calculated by projecting angular velocity onto the normal vector of the swing plane. Swing duration may then be calculated by defining the start of downswing as the latest time prior to impact when the swing plane speed has magnitude zero. Subtracting the start of downswing from the time of impact generates a duration metric called the time to contact, which measures how quickly the batter responds. The amount of bat motion may be measured as the total angle traversed by the bat both in the swing plane (yielding a metric called total swing angle) and in a plane orthogonal to the swing plane (yielding a different metric called off plane angle). A measure of bat acceleration through the swing may be defined by measuring the swing plane speed at the halfway point of a swing; the ratio of this halfway point swing plane speed to the peak swing plane speed through the swing is defined as the swing tempo metric.

One or more embodiments may obtain a database of swings from multiple players. Analysis of the database may be used to generate one or more performance rating functions that rate swings on their relative performance. These performance rating functions may be applied to rate future swings, and to provide feedback to users on the performance and characteristics of their swings. Metrics and other data associated with swings in the database may be combined into feature vectors that may be used for classification and matching algorithms. For example, analysis of the database may be used to group swings into swing styles, where swings associated with the same swing style have similar feature vectors. Feature vector clustering and matching may be used to provide feedback to a user on the style of his or her swing, and to identify other users with similar swings. The feature vector may also include other data related to the swing event, such as for example incoming pitch trajectory or classification, outgoing ball trajectory, or game outcome (such as foul, fly-out, home run, etc.) in order to refine classification and analysis.

In situations where sensor data is unavailable or is saturated at the limit of the sensor's range for a time interval during a swing, one or more embodiments may extrapolate sensor data prior to or after the interval to estimate actual values during this interval. Extrapolation may for example use a Bézier curve. The curve may be for example a cubic Bézier curve with four control points that are selected to match the values and the slopes of the sensor data curve at the endpoints of the interval. One or more embodiments may use a Kalman filter, or a similar state space estimator, to extrapolate sensor data into the time interval. A Kalman filter may for example incorporate a kinematic model of the bat in order to predict motion parameters when sensor readings are not able to fully track the motion, for example because the motion is outside the sensor's measurement range.

One or more embodiments of the invention may calculate a trajectory of the sweet spot or of a similar or other point on a bat or piece of equipment, and may derive metrics describing a swing from this trajectory. The sweet spot trajectory may be calculated from sensor data, for example from a sensor coupled to the bat, which may for example include accelerometer or gyroscope data. Data may be transformed to a reference frame that may for example be centered at the sweet spot at the time of impact. A reference frame may be defined for example, without limitation, with a z-axis pointing vertically upward, and an x-axis oriented so that the longitudinal axis of the bat is in the xz-plane at impact. The time of impact may be calculated by searching the sensor data time series for event signatures that may for example have acceleration and angular velocity exceeding respective threshold values. A sweet spot as utilized herein may also indicate a range of location or shape of area on the piece of equipment where an impact occurs or is to occur, wherein the sweet spot meets a predefined threshold, or value, for maximum energy transfer, maximum ball speed or least vibration or any other metric related to efficiency or power for example, or using any other metric to define the location or range or area or area range on the piece of equipment.

One or more embodiments may detect a virtual impact for an air swing, when a bat may not physically strike a ball. For example, one or more embodiments may detect an air swing by determining whether the swing is a valid air swing, and then detecting a point in the swing when angular velocity in the xy-plane is maximum. A valid air swing may for example require that peak xy angular velocity and peak z-axis acceleration exceed respective threshold values.

One or more embodiments may calculate a start of downswing for a swing, and may calculate a time to contact metric as a difference between the time of impact and the start of downswing.

One or more embodiments may calculate the trajectory of the position of the hands on the bat through the swing. This trajectory may be used for example to calculate a center of rotation for the swing. For example, the center of rotation may be calculated as a point equidistant from the hand position at three different points on the hand trajectory. An axis of rotation may be calculated as an axis perpendicular to the plane through these three points. A body tilt angle may be calculated as the angle between the axis of rotation and the vertical direction.

One or more embodiments may calculate and use a two-lever model of the swing, which models the swing mechanics as a body lever extending from the center of rotation to the hand position, and a bat lever that extends from the hand position to the sweet spot. A body ratio metric may be calculated based on the ratio of the rotation of the body lever through the swing to the rotation of the bat lever. The angle between the bat lever and the body lever changes through the swing as the batter cocks and then releases the wrist. A hinge angle may be calculated through the swing based on the relative orientation between the bat lever and the body lever; for example, the hinge angle may be defined as the angle between the bat lever and the tangent to the body lever. The hinge angle at impact may be used as a swing metric.

A commit event may be calculated to reflect when the batter releases the wrist during the swing. For example, the time of commit may be calculated as the time when the angular velocity of the hinge angle exceeds a threshold value. The hinge angle at the time of commit may be used as a swing metric. The hinge release metric may be calculated as the difference between the hinge angle at impact and the hinge angle at commit.

One or more embodiments may determine a swing plane for the swing. The swing plane may be calculated based on the position, orientation, and velocity of the bat at the time of impact. For example, the swing plane may be a plane through the sweet spot at impact, which is spanned by the bat's longitudinal axis at impact and by the velocity vector of the sweet spot at impact.

At any point in the swing, the distance between the sweet spot and the swing plane may be calculated as an off-plane distance. An on-plane event may be calculated as the point in the swing when the off-plane distance is within a specified threshold and remains within this threshold until impact. An on-plane metric may be calculated as the angular range of motion of the bat or of one or both of the body and bat levers between the on-plane event and the impact event.

The bat forward velocity at any point in time may be calculated as the velocity of the sweet spot projected onto a plane perpendicular to the longitudinal axis of the bat. Bat speed at impact may be calculated as the forward bat speed at the time of impact. A peak bat speed may be calculated as the maximum forward bat speed through the swing. Swing power may be calculated as a product of the bat speed at impact, the mass of the bat, and the average acceleration of the sweet spot during the swing.

A swing plane tilt angle metric may be calculated as the angle between the bat's longitudinal axis at impact and the horizontal. An attack angle metric may be calculated as the angle between the sweet spot velocity vector at impact and the horizontal.

One or more embodiments of the invention may include utilizing sound or at least one Virtual Reality (VR), Augmented Reality (AR) or Mixed Reality (MR) display, glasses or goggles to provide bio-feedback to the user. For example, in one or more embodiments, a sound or visual display may be utilized to provide feedback to the user to indicate a correct position, or movement has been achieved. This enables a user to work on portions of a swing or an entire swing using different body positions, for example to simulate different feet positions in a sand trap for a golf swing for example and obtain feedback regarding the position and/or swing using sound or visual feedback. In addition, by providing metrics regarding the body position, body movement, piece of equipment position, piece of equipment movement or any combination thereof, embodiments of the invention enable a user to work on developing more power and improving skills in a bio-feedback environment and/or combine environment. Embodiments of the system also enable rehabilitation and general training of the body based on the data gathered by the system to suggest areas of the body to strength or stretch to improve the range of motion to avoid injury through use of correct biomechanics.

One or more embodiments of the invention may include an inertial sensor on or in a bat, and a processor that analyzes data from the inertial sensor to generate one or more swing quality metrics. The processor may be attached to a memory that contains a bat geometry definition, which may for example define a hand position and a sweet spot position along the longitudinal axis of the bat. The processor may receive a time series of inertial sensor data, including acceleration data from a three-axis accelerometer and angular velocity data from a three-axis gyroscope. It may then calculate the trajectory of the hand position, the trajectory of the sweet spot, and the trajectory of the bat's longitudinal axis, and the time the bat impacts the ball. From the hand trajectory, the processor may calculate the body tilt axis as the normal to the plane that passes through three distinct points of the hand trajectory. It may calculate the swing plane that is spanned by the velocity vector of the sweet spot at impact and the bat longitudinal axis at impact. It may calculate one or more swing quality metrics based on any or all of the data described above, including for example based on one or more of the time series of inertial sensor data, the time of impact, the trajectories of the hand position, sweet spot, and bat longitudinal axis, the body tilt axis, and the swing plane.

In one or more embodiments, the sweet spot position on the bat may correspond to any or all of an optimum location on the bat for striking the ball, a position on the bat that maximizes energy transfer or ball speed, and a position on the bat that minimizes vibration when hitting the ball.

In one or more embodiments, the longitudinal acceleration—the acceleration of the bat along its longitudinal axis—may be used to calculate a rotational acceleration metric. The start of centripetal acceleration may be calculated as the time at or near a change in sign of the longitudinal acceleration, and an early rotation time may be calculated as a fixed offset after this start of centripetal acceleration. The fixed offset may be for example in the range of 10 to 50 milliseconds. A rotational acceleration metric may be calculated as the difference between the longitudinal acceleration between the early rotation time and the start of centripetal acceleration.

One or more embodiments may calculate a rotation-on-plane ratio at points in time during the swing, and use this ratio to calculate an on-plane efficiency metric. This ratio may be based on angular velocity values transformed to a swing plane coordinate system with the z-axis along the bat longitudinal axis, the y-axis normal to the swing plane, and the x-axis orthogonal to the y and z axes. The rotation-on-plane ratio may be calculated as the ratio of the magnitude of the y-axis angular velocity to the magnitude of the vector sum of the x and y axis angular velocities. The on-plane efficiency may be calculated as the average of the rotation-on-plane ratio between the start of centripetal acceleration and the time of impact.

One or more embodiments may calculate a body-bat angle at points in time during the swing, and use this angle to calculate one or more connection or disconnection metrics. The body-bat angle may be calculated as the angle between the bat longitudinal axis and the body tilt axis. A connection-at-impact metric may be calculated as the body-bat angle at the time of impact. A connection-early metric may be calculated as the body-bat angle at the start of centripetal acceleration. A disconnection-at-impact metric may be calculated as the absolute value of the difference between the connection-at-impact and 90 degrees. A disconnection-early metric may be calculated as the absolute value of the difference between the connection-early and 90 degrees. An average-disconnection metric may be calculated as the average of the disconnection-at-impact and the disconnection-early.

One or more embodiments of the invention may include a swing analysis system that calculates a rotational profile. A bat (or other equipment) may have an inertial sensor coupled to the bat; the sensor may include for example an accelerometer, a gyroscope, and a network interface. Inertial sensor data may be captured at a sequence of times through a swing of the bat by a user. This data may be transmitted to a processor over a network connection, and the processor may analyze the data. This analysis may include calculation of the bat trajectory through the swing, which may include the hand position and sweet spot position through the swing. It may include calculation of the center of rotation of the swing, of a body lever between the center of rotation and the hand position, and of a bat lever from the hand position to the sweet spot position. A body rotation angle may be calculated as the angle between the body lever at any point in time and the initial body lever at the start of the swing. A hinge angle may be calculated as the angle between the bat lever and a tangent perpendicular to the body lever. The body rotation rate may be calculated as the rate of change of the body rotation angle, and the bat rotation rate may be calculated as the rate of change of the hinge angle. A rotational profile of the swing may then be calculated, which includes the body rotation rate over time, the bat rotation rate over time, and the centripetal acceleration of the bat along the bat's longitudinal axis over time.

One or more embodiments may include a database with rotational profiles associated with multiple users, and a swing analysis coupled to the database that compares rotational profiles across users. The swing analysis system may also generate a recommended bat for a user.

In one or more embodiments, the processor that analyzes sensor data may partition the time sequence for the swing into phases. Phases may for example include a load phase that starts at the start of swing, an accelerate phase following the load phase that starts when the centripetal acceleration changes from positive to negative, a peak phase following the acceleration phase, and a transfer phase following the peak phrase and extending to the end of swing when the bat impacts the ball.

In one or more embodiments, the rotational profile may also include one or more swing metrics. These metrics may be calculated for example from any or all of the inertial sensor data, the body rotation rate, the bat rotation rate, and the centripetal acceleration.

Swing metrics may include the peak loading acceleration, which is the maximum positive centripetal acceleration during the load phase. They may include the rate of acceleration, which is an average rate of change of the centripetal acceleration during the accelerate phase. They may include the peak acceleration, which is the minimum negative centripetal acceleration after the load phase and before the end of the swing. They may include the acceleration impulse, which is an integral of the centripetal acceleration between the start of the accelerate phase and the end of swing. They may include the time to peak force, which is the time difference between the start of the accelerate phase and the time when the centripetal acceleration reaches its minimum negative value after the start of the accelerate phase.

Swing metrics may include the peak bat rotation rate, which is the maximum value of the bat rotation rate between the start of the load phase and the end of the swing. They may include the peak body rotation rate, which is the maximum value of the body rotation rate between the start of the load phase and the end of the swing. They may include a ratio between the peak bat rotation rate and the peak body rotation rate.

BRIEF DESCRIPTION OF THE DRAWINGS

The above and other aspects, features and advantages of the ideas conveyed through this disclosure will be more apparent from the following more particular description thereof, presented in conjunction with the following drawings wherein:

FIG. 24A shows a variation of the embodiment of FIG. 24 that uses video cameras instead of inertial sensors to capture motion data.

FIG. 25 shows illustrative bat geometry data that may be used in one or more embodiments to calculate swing quality metrics.

FIG. 39B shows an illustrative equipment fitting process that compares swing metrics obtained from swings using different equipment options.

FIG. 40 shows illustrative components of a rotational profile: centripetal acceleration, body rotation rate, and bat rotation rate.

FIG. 41A shows illustrative centripetal acceleration curves for baseball players of different skill levels.

FIG. 41B shows illustrative body rotation rate and bat rotation rate curves for baseball players of different skill levels.

FIG. 42 illustrates partitioning a swing into four phases: load, accelerate, peak, and transfer.

FIG. 43 shows five illustrative metrics that may be calculated from the centripetal acceleration curve.

FIG. 44 shows three illustrative metrics that may be calculated from the body rotation rate and bat rotation rate curves.

FIG. 45 shows an example of calculating a rotational profile for a golf swing.

DETAILED DESCRIPTION OF THE INVENTION

A swing analysis system that calculates a rotational profile will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

Figure 1:
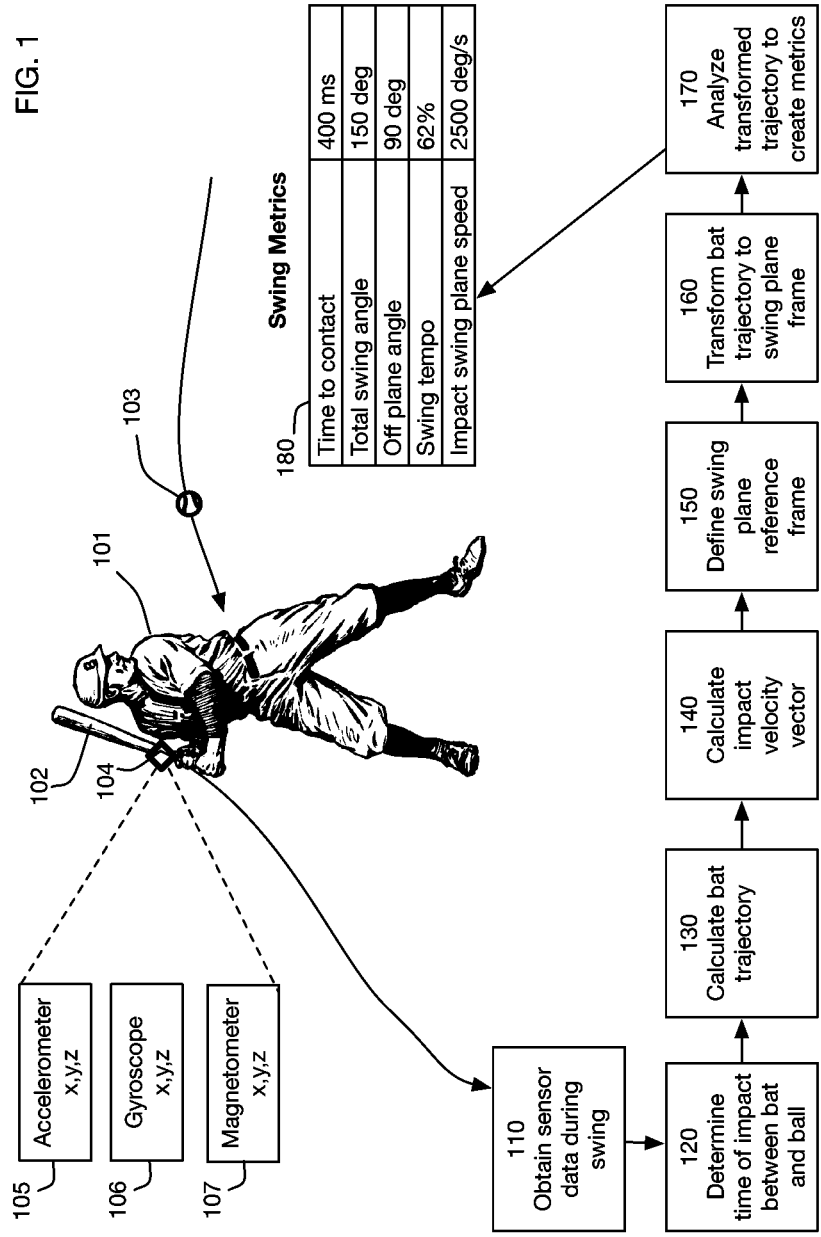
FIG. 1 shows an overview flowchart of an embodiment that processes sensor data in a swing plane reference frame to generate several swing metrics for the swing of a baseball bat.

FIG. 1 shows an overview of an embodiment of the invention. User 101 swings a baseball bat 102 to hit an incoming ball 103. Data is collected throughout the swing from sensor 104 attached to the bat. Sensor 104 may incorporate any type of sensor technology or technologies to measure any quantities, such as for example any aspects of the motion, position, or orientation of the bat. The sensor may be coupled with the proximal end of the bat, the distal end of the bat or anywhere in between. In one or more embodiments the sensor 104 may comprise two or more sensors at different locations on the bat. For example, without limitation, sensor 104 may contain any or all of a three axis accelerometer 105, a three axis gyroscope 106, and a three axis magnetometer 107. These sensor types are illustrative; one or more embodiments may use sensor data from any type or types of sensors to track the swing of bat 102. In one or more embodiments the sensor 104 may not be physically attached to the bat; for example, the sensor may be stationary and it may observe the moving bat using technologies such as video, radar, LIDAR, or ultrasound. In one or more embodiments, data from multiple types of sensors may be combined using sensor fusion. For example, sensor data from an inertial sensor on a bat may be fused with radar data or other information from external devices to calculate a bat trajectory. Sensors may measure motion or other parameters on any number of axes. Sensors may measure these parameters at any desired frequency; higher measurement frequency may for example support more detailed analysis of the swing. For example, without limitation, sensor 104 may collect data once per second, ten times per second, one hundred times per second, one thousand times per second, ten thousand times per second, or at frequencies above ten thousand times per second.

In the embodiment shown in FIG. 1, bat 102 is a baseball bat. One or more embodiments may obtain and analyze data for the swing of any type of bat or similar object, including for example, without limitation, a baseball bat, a softball bat, a cricket bat, and in one or more embodiments, a tennis racket, a table tennis racket, a badminton racket, a squash racket, a racquetball racket, a golf club, a polo mallet, a hockey stick, a field hockey stick, and a lacrosse stick or any other type of equipment that involves a swing.

Data from sensor 104 is obtained in step 110. One or more embodiments may use any data transfer technology or technologies to obtain sensor data. For example, without limitation, data may be transferred over a wireless network, over a wired network, or using a data storage medium that is moved from one system to another. Data may be obtained in real time during a swing, obtained after a swing occurs, or obtained using a combination of real-time transfer and transfer after a swing event.

Steps 120 through 170 analyze data from sensor 104 to characterize the swing, resulting in swing metrics 180. These steps may be performed in any order, or in parallel. These steps may be performed on any system or combination of systems. For example, without limitation, any or all of these steps may be performed on a computer, a mobile computer, a laptop computer, a notebook computer a desktop computer, a tablet computer, a mobile phone, a smart phone, a smart watch, a microprocessor, a server, or a network of any of these devices. In one or more embodiments the sensor 104 may contain a processor or processors that perform some or all of the steps 110 through 170.

Step 120 determines the time of impact between bat 102 and ball 103. This step may for example detect a signature in the sensor data that indicates a collision. For example, if sensor 104 includes an accelerometer such as accelerometer 105, a rapid spike in acceleration may be a signature of an impact. Similarly, if sensor 104 includes a gyroscope such as gyroscope 106, a rapid reduction in angular velocity may be a signature of an impact. One or more embodiments may for example use sensors that directly measure impact, such as pressure sensors or contact switches. In one or more embodiments, a swing endpoint may be defined even if the bat does not hit the ball, for example during practice swings, air swings, or strikes. This swing endpoint may be based for example, without limitation, on parameters such as the location of the bat relative to the plate or to an incoming ball, the aim angle of the bat, or the point in time when the bat achieves maximum velocity or maximum angular velocity. A calculated swing endpoint may be used instead of an actual impact time for any of the subsequent metric calculations described below.

Step 130 calculates a trajectory of the bat 102 from a starting point of the swing through the impact time determined in step 120. In one or more embodiments the trajectory may also extend beyond the impact or prior to the start of the swing. The bat trajectory may be a time series of motion data samples, each of which represents the state of the bat at a point in time during the swing. For example, each sample may include data on any or all of the bat's position, orientation, velocity, angular velocity, acceleration, or angular acceleration. In one or more embodiments a sample may include data for multiple locations on the bat. Methods to calculate an object's trajectory from motion sensor data are known in the art. For example, one or more embodiments may use inertial navigation algorithms known in the art to calculate the position and orientation of the bat over time from acceleration data (for example from accelerometer 105) and from angular velocity data (for example from gyroscope 106). Data from other sensors, such as for example magnetometer 107, may for example provide redundant measurements to correct errors in inertial navigation algorithms.

Because the orientation and position of sensor 104 changes throughout the swing, the bat trajectory calculated in step 130 may not be in a convenient form for analysis. Therefore, in step 150 a standardized reference frame is defined based on the swing itself. We refer to this reference frame as the swing plane reference frame. In step 160 the bat trajectory is transformed to this reference frame. In step 170 the transformed trajectory is used to analyze the swing, and to generate one or more swing metrics describing and characterizing the swing. Illustrative swing metrics 180 describe for example the timing of the swing, the speed of the swing, and the angles traversed during the swing.

Figure 2:
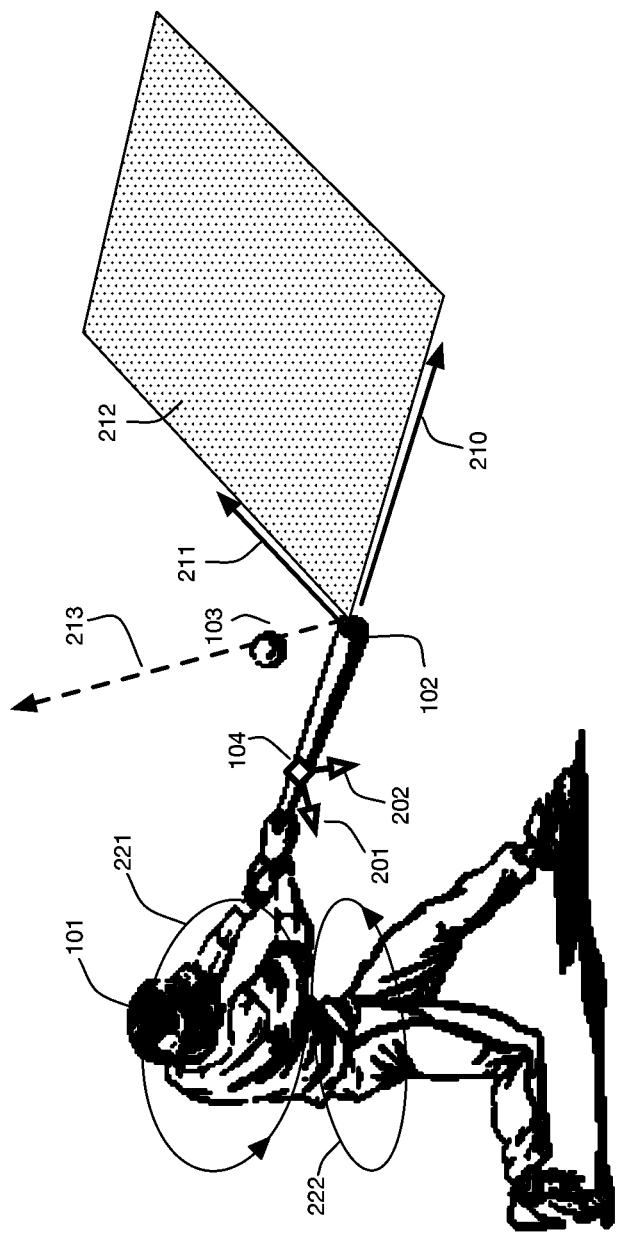
FIG. 2 shows a reference frame based on a swing plane defined by the bat orientation and by the velocity vector of the bat at the time of impact with the ball.

FIG. 2 illustrates definition and calculating of the swing plane reference frame. This reference frame is defined by the bat's orientation and motion at the time of impact between the bat 102 and the ball 103. A swing plane 212 is defined by two axes: a first axis 210 is the longitudinal axis of the bat (along the bat's long dimension); a second axis 211 is in the direction of the bat's velocity at the time of impact. The velocity vector at impact may also be calculated as a tangent vector to the bat's instantaneous rotation round the angular velocity axis. This impact velocity vector 211 may be calculated or obtained from the bat trajectory. In one or more embodiments a specific point on the bat, such as for example the sweet spot, may be used to define the impact velocity vector. The swing plane 212 is the plane spanned by the vectors 210 and 211. To complete the reference frame, a third orthogonal off-plane axis 213 is selected as the normal vector to the plane 212. The swing plane 212 defined by the axes 210 and 211 provides a reference frame that can be calculated from data generated by bat sensor 104. Other planes of rotation that may be relevant to the kinematics of the swing include for example the rotational plane 221 for the batter's shoulders, and the rotational plane 222 for the batter's hips. In one or more embodiments additional sensors, for example sensors attached to the batter's shoulders and hips, may be used to calculate these body rotational planes in addition to the swing plane 212.

Figure 3:
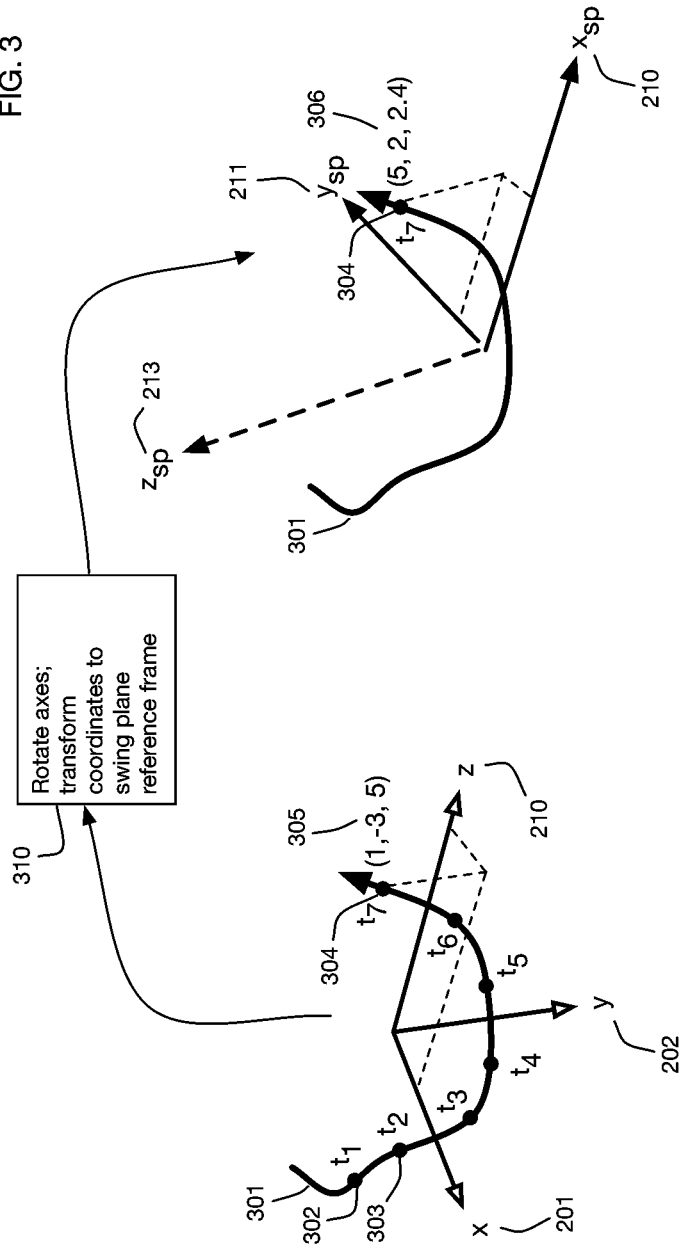
FIG. 3 illustrates transformation of a bat trajectory from a local sensor frame to the swing plane reference frame of FIG. 2.

In the example shown in FIG. 2, sensor 104 has a local reference frame in which sensor data is measured. This local reference frame in general may have a completely different orientation from the swing plane reference frame defined by axes 210, 211, and 213. For example, the sensor local reference frame may have axes 201, 202, and 210; in this example one axis of the sensor local reference frame is aligned with the bat longitudinal axis, but the other axes are in arbitrary directions due to the rotational symmetry of the bat around this axis. To facilitate standardized analysis of swings and comparison of swings across players, bat trajectory information is transformed from the sensor local reference frame into the swing plane reference frame. FIG. 3 illustrates this transformation. Bat trajectory 301 includes motion data samples at various points in time, such as for example points 302, 303, and 304. These samples may include any information on the state of the bat, such as position, orientation, or derivatives of these values like velocity and angular velocity. For illustration, the bat trajectory 301 is shown as a single curve in three dimensional space (for example as a curve of bat position over time); however, in one or more embodiments the bat trajectory may include any data with any number of dimensions. In the sensor local reference frame defined, for illustration, by axes 201, 202, and 210, each sample point has coordinates such as coordinates 305 for point 304. Transformation 310 maps the sample points into the swing plane reference frame, for example using a rotation of the axes 201, 202, and 210 into axes 210, 211, and 213. For example, in the swing plane reference frame, point 304 on the bat trajectory 301 has coordinates 306.

Figure 4:
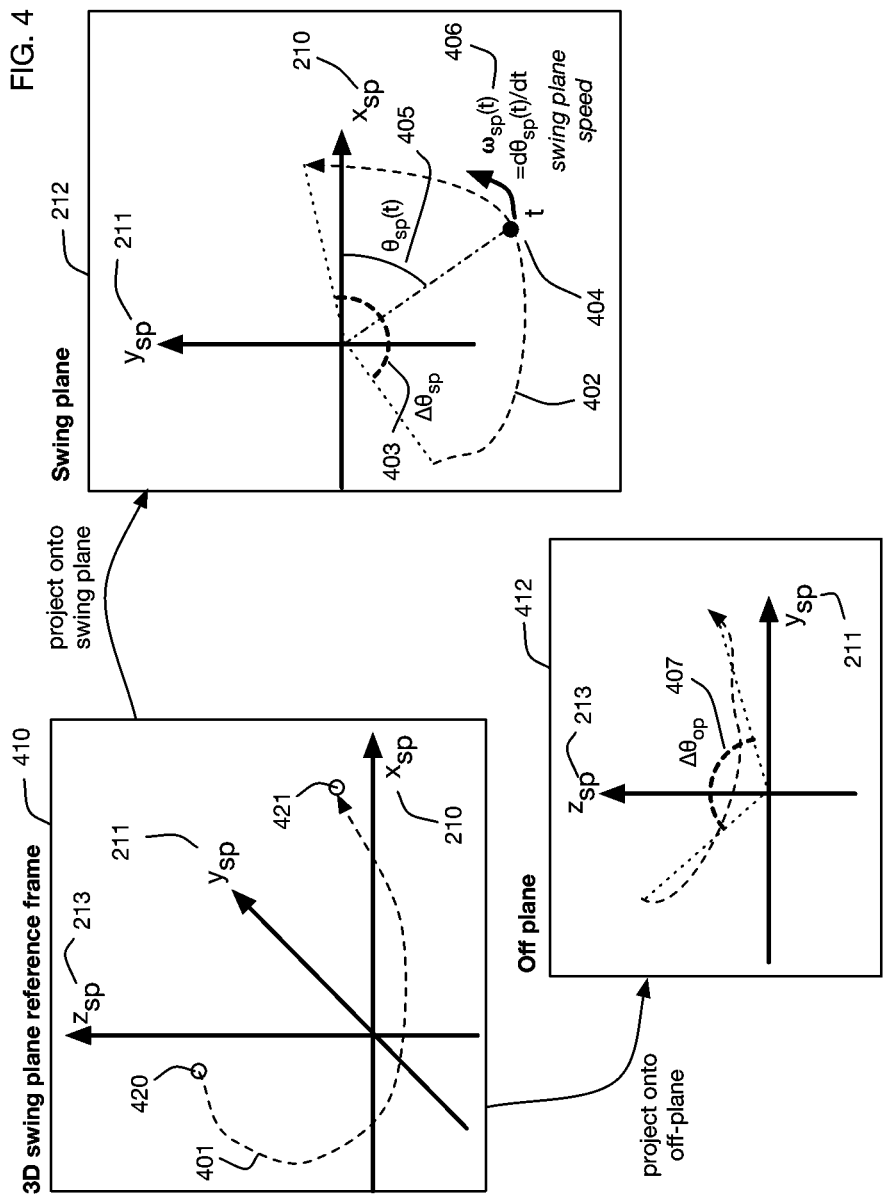
FIG. 4 illustrates various metrics derived from the swing plane reference frame, including a total swing angle in the swing plane, an off-plane swing angle, and a swing plane speed.

One or more embodiments of the invention may analyze the bat trajectory in the swing plane reference frame to measure and characterize the swing. FIG. 4 shows illustrative metrics for angular change that are defined relative to the swing plane reference frame. Bat trajectory 401 is a three dimensional curve in the three dimensional swing plane reference frame 410 defined by axes 210, 211, and 213. Trajectory 401 has starting point 420, representing a start of the swing, and endpoint 421, representing for example the time of impact between the bat and the ball. This curve may be projected onto the two-dimensional swing plane 212 defined by axes 210 and 211, and various metrics may be calculated from this projection. For example, the 2D curve 402 is the projection of the bat trajectory 401 onto plane 212. As the curve 402 proceeds from the starting point to the endpoint of the trajectory, it subtends an angle 403 ($\Delta\theta_{sp}$) in the swing plane (with vertex at the origin). This angle 403, which we refer to as the total swing angle, is a swing metric that indicates the total amount of bat movement during the swing in the swing plane. Similarly, the bat trajectory 401 may be projected onto a plane 412 orthogonal to the swing plane, and the angle 407 subtended by the projected trajectory is a different swing metric that we refer to as the off-plane angle. The total swing angle metric and the off-plane angle metric provide a useful characterization of how the batter is moving the bat through the swing. Projection of the trajectory 401 onto swing plane 212 also provides a measure of the instantaneous angular velocity 406 of the trajectory at any point in time, such as at illustrative point 404. This instantaneous angular velocity in the swing plane, which we refer to as the swing plane speed, is a more useful metric of the bat's motion than for example the total linear velocity of the bat, which includes an off-plane component of velocity that is not as relevant for the power of the swing. The swing plane speed 406 may be calculated for example as the derivative of the instantaneous angle 405 between the point 404 on the projected trajectory 402 and the axis 210. In one or more embodiments that include a gyroscope, which measures angular velocity directly, the swing plane speed may be calculated by projecting the measured angular velocity onto the axis orthogonal to the swing plane 212.

Figure 5:
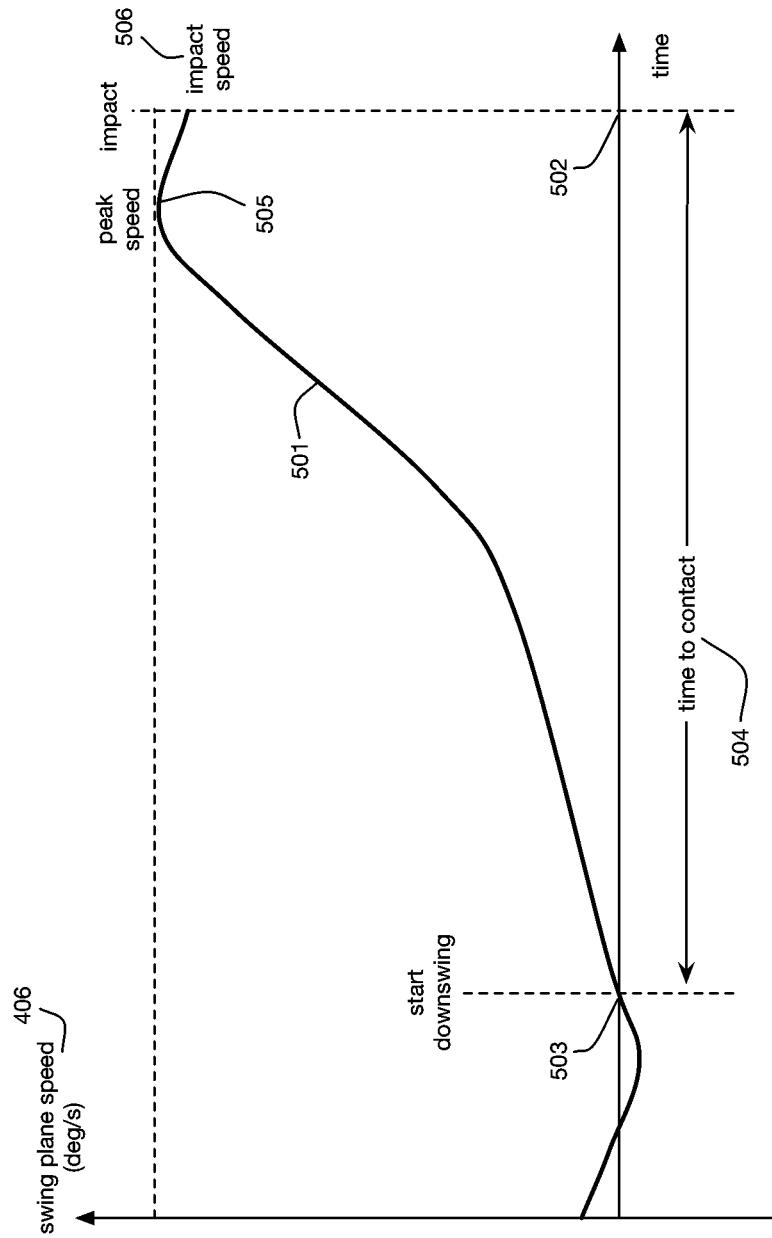
FIG. 5 illustrates derivation of a time to contact swing metric that measures how quickly the batter responds.

The curve of swing plane speed over time through the swing provides additional useful information about the swing. FIG. 5 shows an illustrative curve 501 of the swing plane speed 406 as a function of time. The curve typically increases through the swing as the batter accelerates the bat. The swing plane speed reaches a maximum value 505 during the swing. For some swings, the peak speed 505 may occur at the time of impact 502; however, this is not necessarily the case for all swings. The impact swing plane speed 506 is an important swing metric since it greatly affects the distance and power of the hit. The swing plane speed curve may be used to define an unambiguous point in time for the start of the downswing of a swing: this start of downswing 503 may be defined as the last point in time when the swing plane speed is zero prior to the impact. This definition is based on an unambiguous physical event rather than an arbitrarily defined threshold crossing. This provides a clear advantage in terms of metric consistency and physical significance. If there is no zero crossing, as is the case in certain swing styles, we define the start of downswing where the slope and magnitude of the swing plane component meet certain threshold criteria. This fallback definition does not provide the clear advantages of the zero crossing; however, because it is based on the swing plane component, it provides greater consistency than a definition based on vector magnitude, particularly across heterogeneous swing styles where much of the variability (e.g., bat waggle) occurs in the off-plane component.

Using the start of downswing 503 and the time of impact 502, a total swing time, which we refer to as the time to contact metric, may be defined as the difference 504 between the impact time 502 and the start of downswing time 503. This time to contact metric is an important metric related to the batter's ability to read the pitch.

Figure 6:
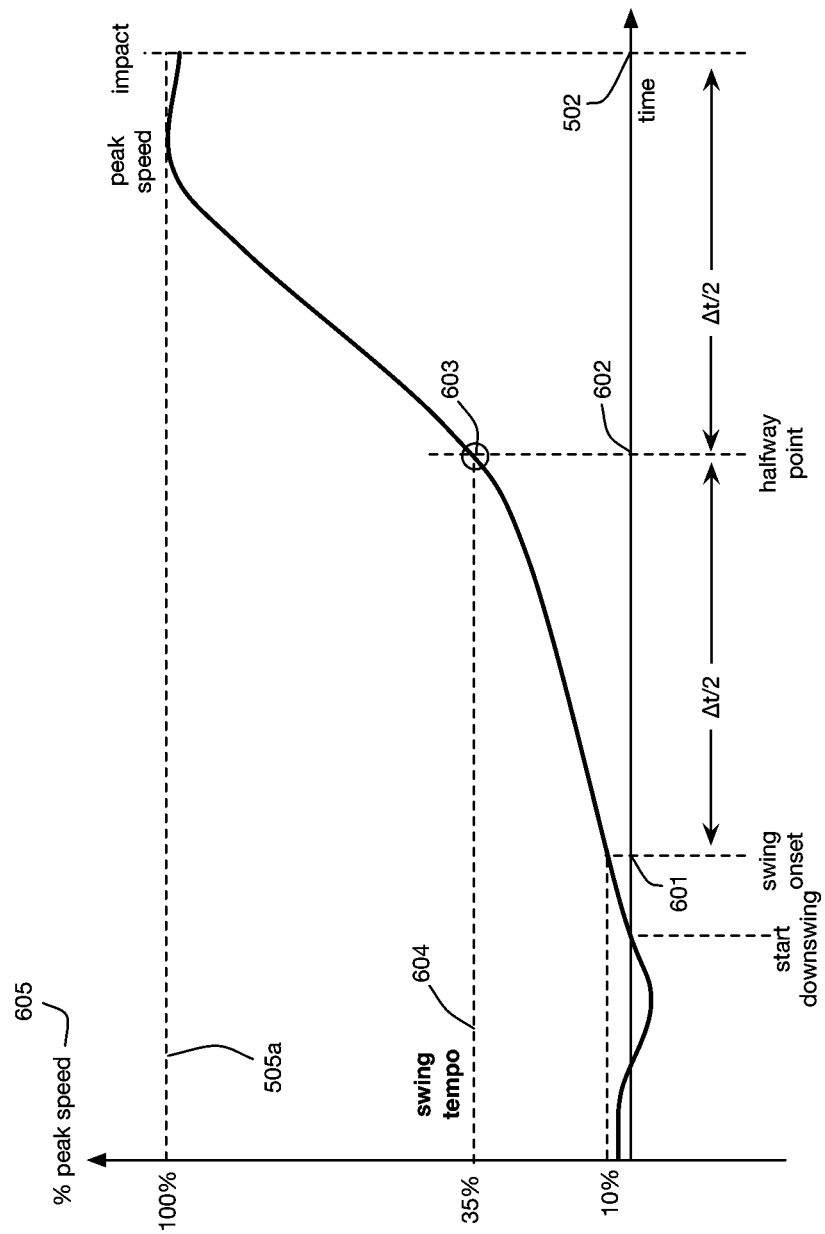
FIG. 6 illustrates derivation of a swing tempo metric based on swing plane speed, which indicates how quickly the swing plane speed increases through the swing.

The rate at which the swing plane speed increases through the swing also provides a useful metric. FIG. 6 illustrates a method to standardize this metric by measuring the fraction of the peak speed achieved at the halfway point of the swing. To allow meaningful comparison across players with different swing styles, the swing plane speed curve is normalized so that swing plane speed is measured as a percentage 605 of the peak speed. Thus the normalized swing speed curve starts at zero at the start of downswing, and increases to 100% at the peak speed. A halfway point 602 is defined for the swing, and the fraction 603 of the peak speed at this point is defined as the swing tempo metric 604. In one or more embodiments the halfway point may be defined as halfway between the start of downswing and the time of impact. However, empirical analysis of swings shows that a more robust halfway point may be defined by selecting a swing onset time 601 as a time at which the swing plane speed reaches a specified small fraction of the peak speed, such as for example 10%, and by defining the halfway point as halfway between the swing onset time and the time of impact.

This definition of the swing tempo metric is based on the insight from comparing statistical distributions, where the greatest variability in deviation from an ideal curve occurs at the half-way point between two fixed endpoints. The significance of this metric comes from an understanding of the kinematic chain (hips, shoulders, arms, wrists) for transferring energy from the body to a baseball bat. A rotationally efficient swing will derive a certain amount of energy from the hips and shoulders compared to the arms and wrists. We can infer how rotationally efficient a baseball swing is by the percentage of speed in the "body" half of the swing relative to the "arm" half. An ideal swing tempo range is learned from empirical data collected from elite-level batters. Deviation from the ideal tempo range, either high or low, is used to provide feedback and prescribe drills to the batter in order to improve performance. A low tempo typically indicates that the swing is dominated by arms (e.g., casting), while a high tempo indicates that a swing is dominated by body (at the expense of bat control).

In one or more embodiments, additional tempo metrics may be defined at other points in a swing, in addition to the halfway point tempo metric described above. For example, without limitation, an early tempo metric may be defined as the fraction of peak speed achieved at the 25% point of the swing, a mid-tempo metric may be defined as the fraction of peak speed achieved at the 50% point of the swing (as discussed above), and a late tempo metric may be defined as the fraction of peak speed achieved at the 75% point of the swing. The three tempo metrics may isolate the effect of different segments of the kinematic chain of the swing; for example, the early tempo metric may characterize the rotation of hips and torso, the mid-tempo metric may characterize the rotation of the torso and arms, and the late tempo metric may characterize the rotation of the arms and bat. These percentages are illustrative; one or more embodiments may measure swing tempo at any point or points in a swing.

Figure 7:
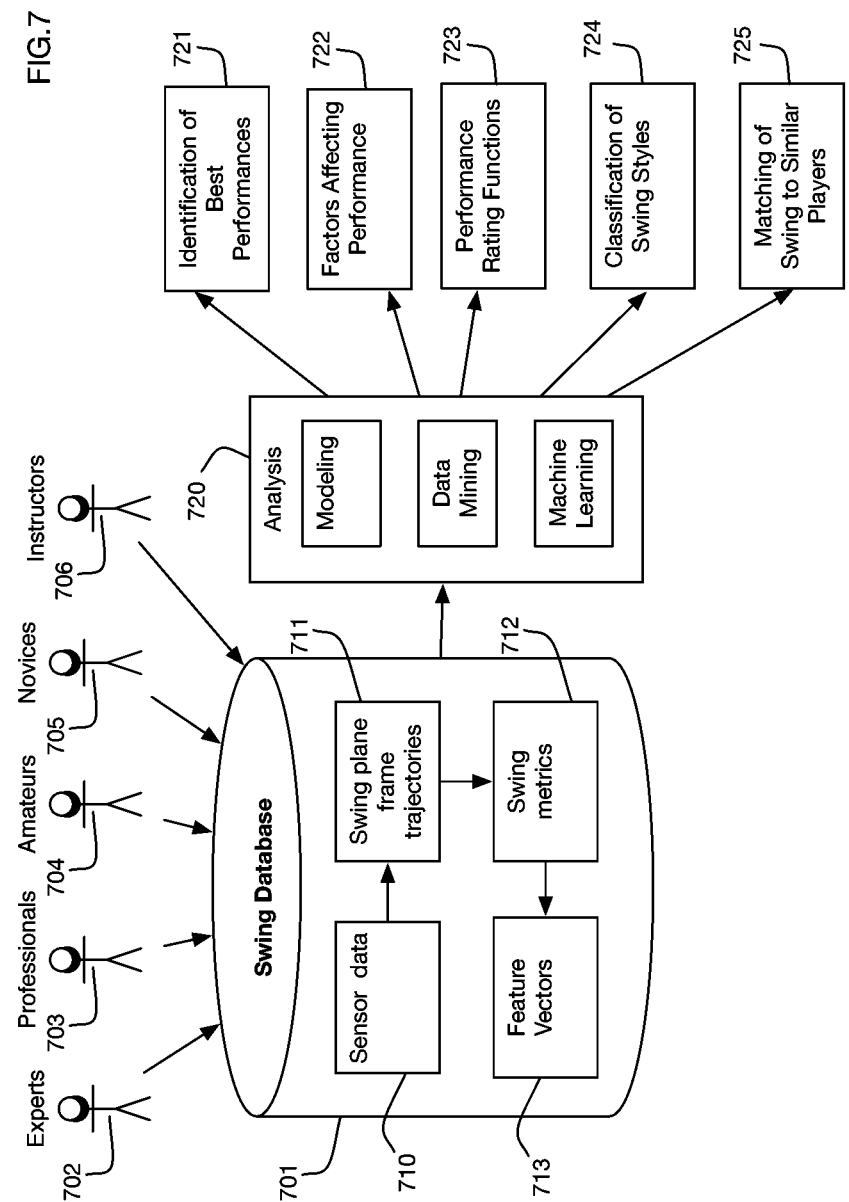
FIG. 7 illustrates an embodiment that collects swing data from multiple users into a swing database, and that analyzes this database to generate methods of rating and classifying swings.

In one or more embodiments, swing data and swing metrics may be collected from multiple users and organized in a swing database for further analysis. FIG. 7 illustrates an embodiment that collects data into swing database 701 from multiple types of users, including for example, without limitation, experts 702, professionals 703, amateurs 704, novices 705, and instructors 706. Data in the swing database may include for example, without limitation, sensor data 710, bat trajectories in the swing plane frame 711, and swing metrics 712 (such as for example the total swing angle, off-plane angle, time to contact, impact swing plane speed, and tempo metrics described above). Multiple metrics may be combined into feature vectors 713 that may be used to classify, categorize, compare, or analyze swings. Data from the database may be used for various analysis procedures 720, which may include for example any or all of modeling swings and batters, data mining the database for patterns or trends, and applying machine learning techniques to learn relationships, functions, or categories. Outputs of the analyses 720 may include for example identification of best performances 721 that flag certain swings or groups of swings as illustrative of ideal or maximum performance; factors affecting performance 722 that identify swing characteristics that contribute to or detract from high performance; performance rating functions 723 that rate swings on how close they are to ideal performance levels; classifications of swing styles 724 that map swings into categories reflecting similar characteristics or similar performance; and matching of swings to similar players 725 that indicate which other swings or other players are most similar to a given swing or player.

Figure 8:
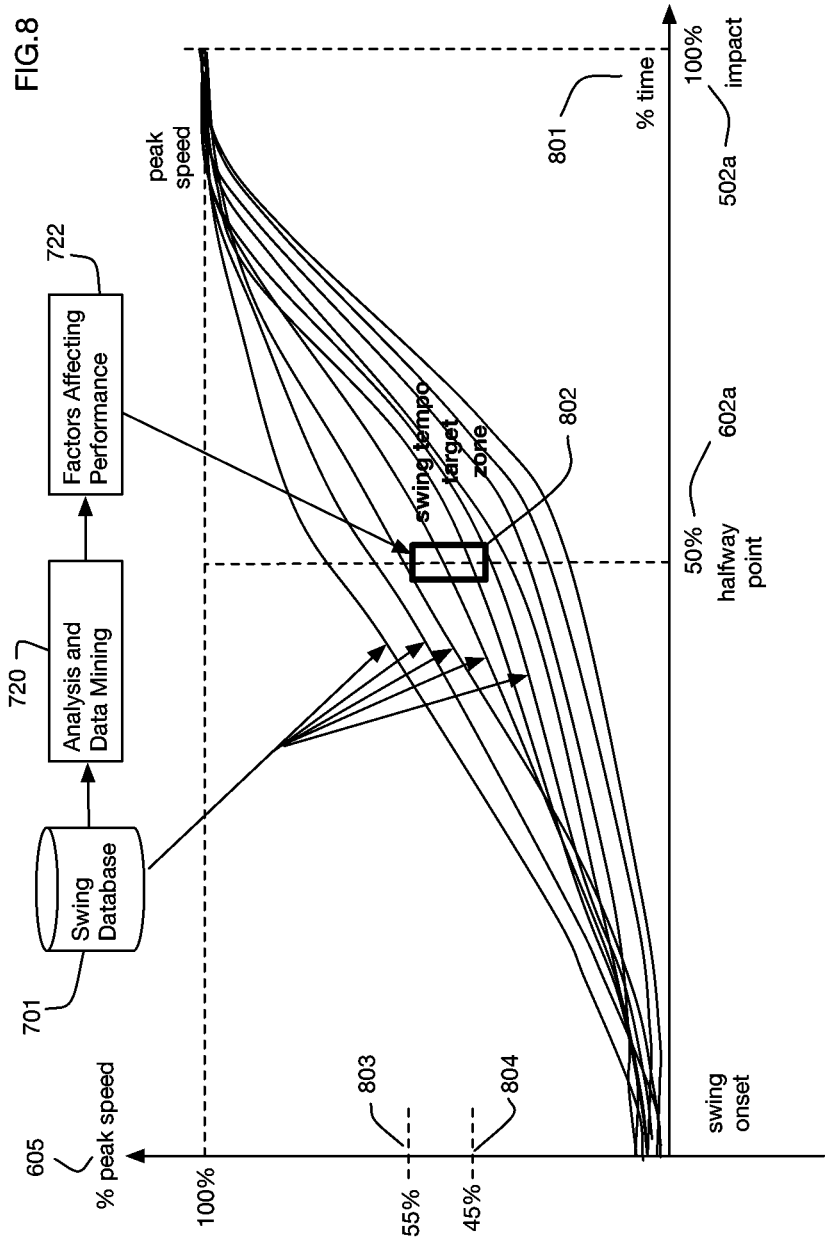
FIG. 8 illustrates an embodiment that analyzes swing tempo from multiple users to determine a target zone for peak performance.

FIG. 8 illustrates an example of the data analysis methods described with respect to FIG. 7, using the swing tempo metric defined above. Using swing database 701 as input, data analysis and data mining process 720 compares swing plane speed curves across players to determine factors affecting performance 722. This analysis indicates that best performance occurs when swing tempo is in a target zone 802, for example in a range between 804 and 803. This analysis uses normalized swing plane speed curves for the swings in database 701, with the swing plane speed axis normalized to the percentage of peak speed 605, and the time axis 801 normalized to a percentage of swing time between swing onset (0%) and impact 502a (100%). The normalized swing plane speed at halfway point 602a (50%) is the swing tempo metric for each swing.

Figure 9:
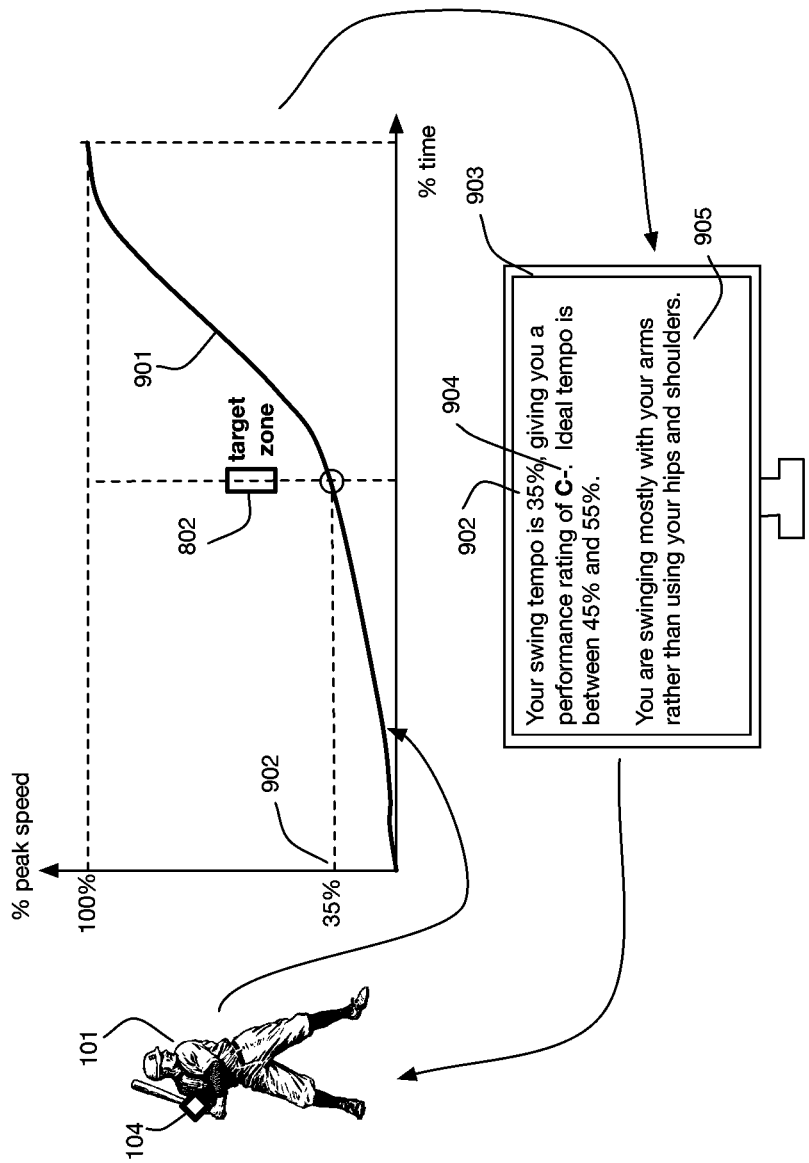
FIG. 9 shows an embodiment that provides feedback to a user on his or her swing by comparing the swing tempo to the target zone described in FIG. 8.

Using the analysis illustrated in FIG. 8, an individual swing may be evaluated by comparing it to the empirically derived criteria for best performance. FIG. 9 illustrates an example with batter 101 generating a swing plane speed curve 901 for a swing. The measured swing tempo 902 for this swing is compared to the target zone 802 in order to rate the swing's performance. Feedback is then provided to batter 101, for example on computer screen 903. This feedback provides the swing tempo metric 902, as well as a performance rating 904 that is based on comparing the swing to performance criteria derived from empirical analysis. The feedback may also include specific critiques such as 905 that diagnose the swing or suggest corrections or improvements.

One or more embodiments may provide feedback to a batter or to other users (such as a coach or trainer) using any desired method or system. For example, without limitation, feedback may be displayed on any computer, laptop, notebook, tablet, mobile phone, smart watch, or wearable device. Feedback may be provided using a specific app, or transmitted via general messaging systems such as email or text messages. Feedback may be audio, visual, haptic, or any combination thereof.

Figure 10:
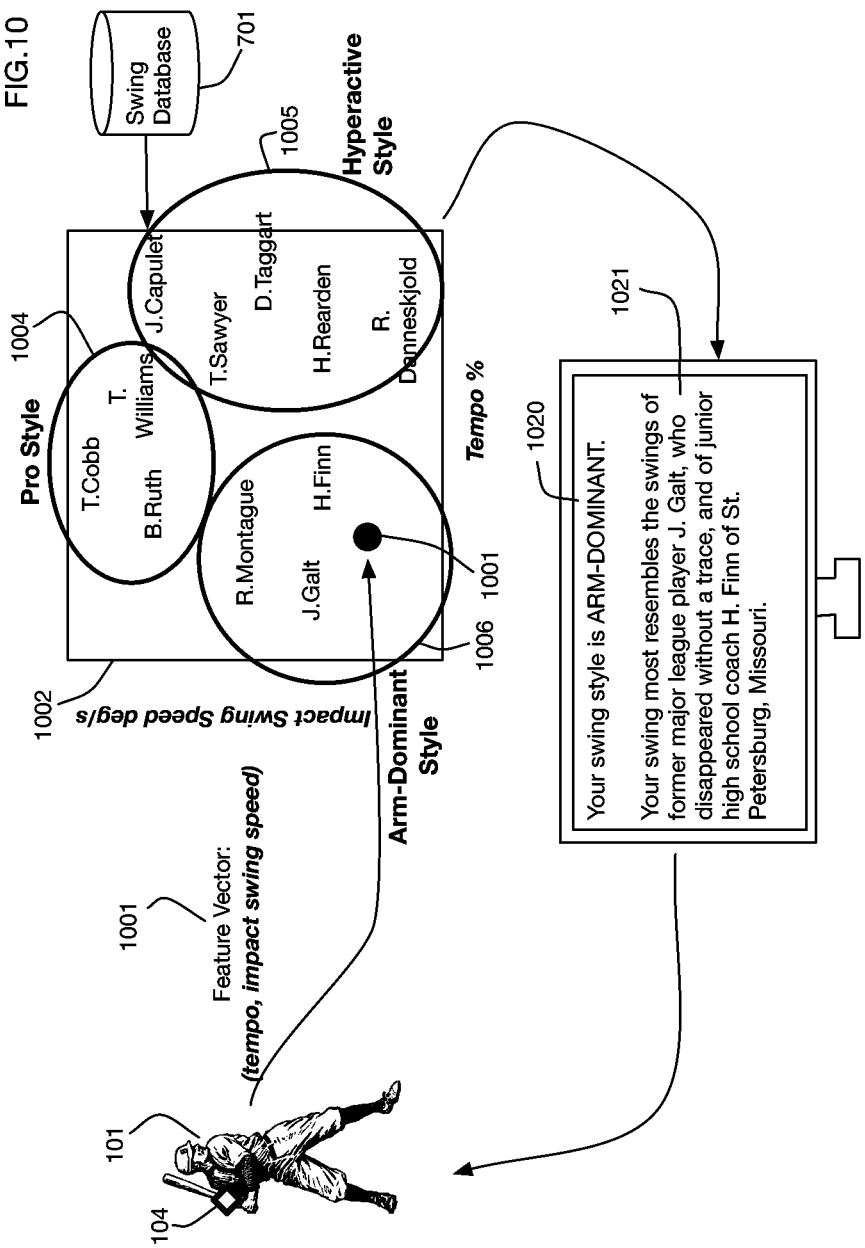
FIG. 10 illustrates an embodiment that classifies swings into swing styles based on a feature vector that combines multiple swing metrics; feedback to a user indicates the swing style as well as identifying other players with similar swings.

FIG. 10 continues the example of FIG. 9 to illustrate additional analysis and feedback for a swing based on comparisons with swings in a swing database. In this example, a feature vector 1001 is generated for a particular swing by batter 101. For illustration, this feature vector is a combination of the swing tempo and the impact swing plane speed. One or more embodiments may generate feature vectors using any combinations of metrics or of any data derived from sensor data or bat trajectories. Swings from swing database 701 are compared on grid 1002 using this feature vector, and are analyzed (for example using cluster analysis techniques known in the art) to categorize swings into a set of swing styles. For example, the analysis may partition swings into three swing styles 1004, 1005, and 1006. The feature vector 1001 corresponding to the swing by batter 101 places the swing into swing style cluster 1006. Feedback to the batter indicates this swing style 1020. In addition, the batter's swing may be matched against typical swings from other users to provide feedback 1021 that identifies other users with swings that resemble the batter's swing.

Figure 11:
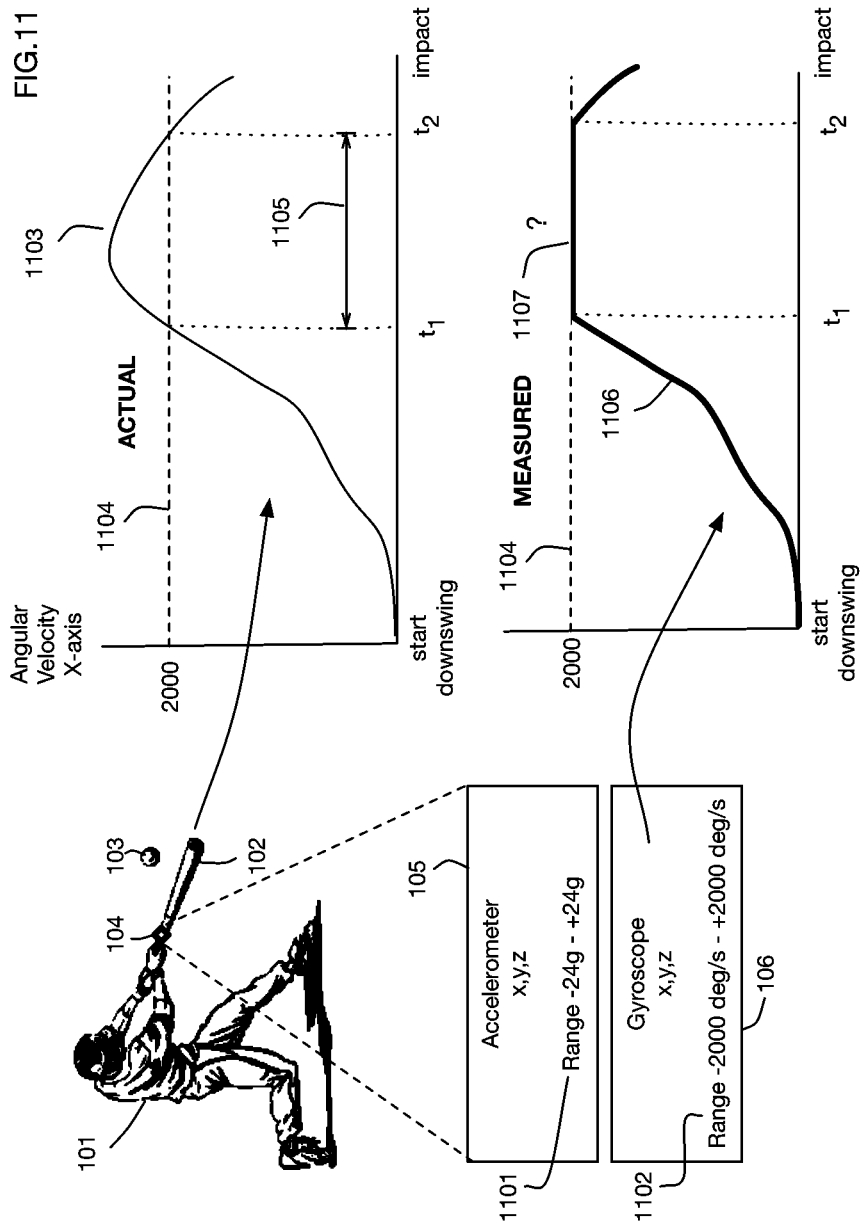
FIG. 11 shows a potential issue that may arise when a sensor has a limited range and the actual motion of the bat exceeds this measurement range during a time interval within the swing.

In some situations, one or more of the sensors that measure the motion the bat may have insufficient range to measure the complete motion throughout the entire swing. FIG. 11 shows an example of this situation where the sensor 104 on bat 102 includes accelerometer 105 with range 1101, and gyroscope 106 with range 106. Taking the angular velocity around the x-axis of the sensor as an illustrative example, the actual x-axis angular velocity 1103 exceeds the upper limit 1104 of measurement range 1102 during time interval 1105. Therefore, the measured sensor values 1106 cannot track the true values 1103 of the motion during this interval 1105. Instead the measured value 1107 during this interval is saturated at the upper limit 1104. This saturation may affect the accuracy of swing metrics. This example using the x-axis of the gyroscope is illustrative; a similar issue may occur with any sensor (including for example the accelerometer 105 as well as the gyroscope 106) and with data from any axis of any sensor.

Figure 12:
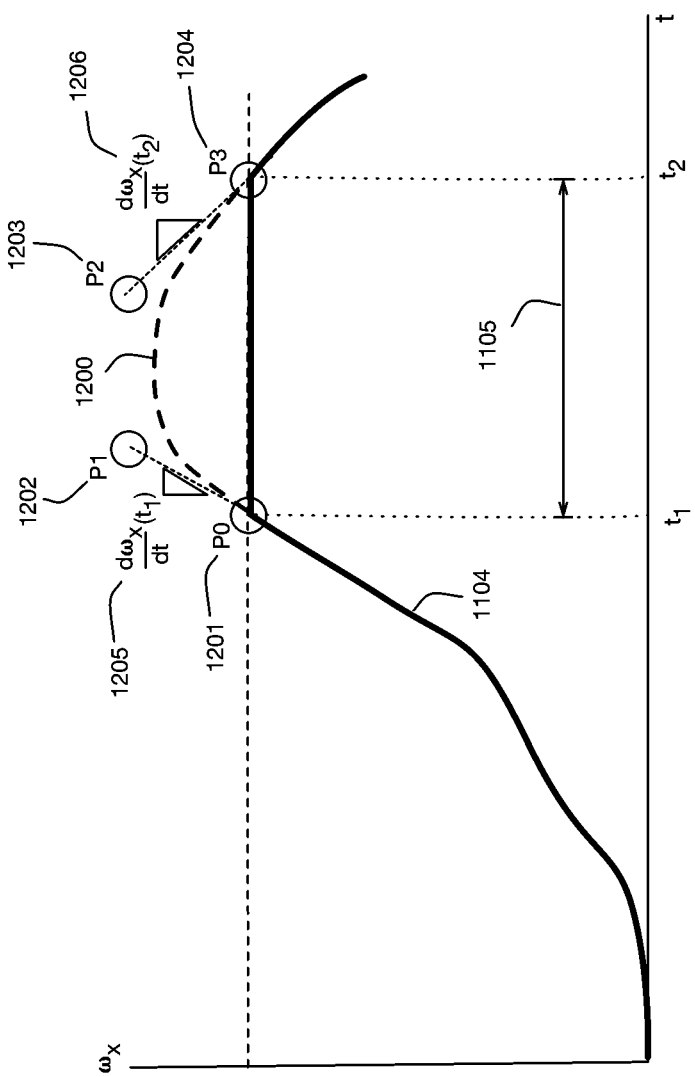
FIG. 12 illustrates an embodiment that addresses the limited range situation shown in FIG. 11 by extrapolating sensor data from before and after the time interval, in this example using a cubic Bézier curve.

To address this issue, one or more embodiments of the invention may extrapolate sensor data from prior to or after the time interval 1105 when the sensor is saturated. Extrapolation may also be used when sensor data is unavailable for a period of time for any other reason, for example because of a limited sampling rate, a recalibration period, or a defective sensor. Extrapolation may be used for any sensor or sensors, or any axis of any sensor or sensors. Embodiments may use any method to extrapolate sensor data into any time interval. FIG. 12 illustrates an embodiment that extrapolates sensor data from both endpoints of the time interval by constructing a Bézier curve 1200 for the values in the interval. In this example, the curve 1200 is a cubic Bézier curve defined by the four control points 1201, 1202, 1203, and 1204. This is illustrative; one or more embodiments may use Bézier curves or any other splines or curves of any order. Control points 1201 and 1204 match the values of the sensor measurements 1104 at the endpoints of interval 1105. The internal control points 1202 and 1203 are chosen to match the slopes of curve 1104 at these endpoints. Specifically, the tangent value 1205 of the curve 1104 at point 1201 is the slope of the line between control points 1201 and 1202, and the tangent value 1206 of the curve 1104 at point 1204 is the slope of the line between control points 1203 and 1204. Points 1202 and 1203 may also be chosen to limit for example the maximum value of the curve 1200 in the interval.

One or more embodiments may select control points for a Bézier curve in such a way as to satisfy the initial and/or final conditions (magnitude and slope) and also to satisfy additional constraints on the maximum absolute value and maximum extrapolation duration. For two-sided extrapolation (no impact events), four control points may be used as shown for example in FIG. 12: the initial and final points are placed where the curve crosses the saturation threshold, and two interior control points are along a line matching the slope of the curve at some distance, which is constrained by some maximum time duration and by a maximum absolute value. This approach provides control of the shape of the extrapolation curve better than a cubic polynomial fit, which will match the same slope and value constraints but may exceed the other physical constraints. If the initial or final edge of the saturation interval is an impact event, then the unconstrained edge may be represented by a single control point, resulting in a three-point Bézier curve. Again, the time and value for this single control point may be selected to achieve the desired shape of the extrapolated curve into the impact event. Because a Bézier curve is not parametric in time, it may be necessary to resample the extrapolated curve at the original sample times. This type of Bézier extrapolation may be applied to an individual saturated sensor axis (independent of the other components) or a composite value (e.g., the x-y resultant or total vector magnitude). The shape of the composite curve may be easier to model or constrain than the underlying individual components for particular kinematic events, resulting in increased accuracy of the extrapolated result. If the underlying component values are needed, they can be obtained by solving for the unknown saturated component(s) from the extrapolated composite result and unsaturated component values (the result will be under-determined if more than one component is saturated).

Figure 13:
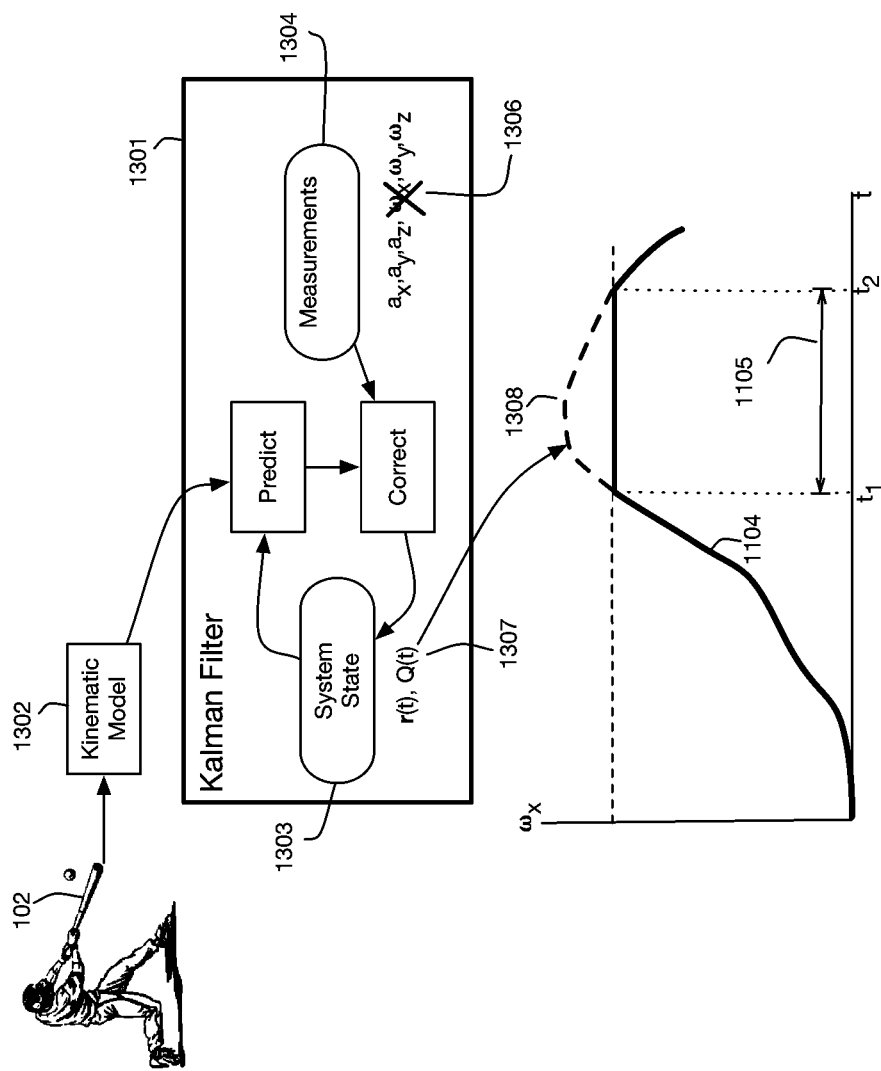
FIG. 13 illustrates an embodiment that extrapolates sensor data using a Kalman filter to estimate values when the measurement range of the sensor is exceeded.

Another approach to extrapolation that may be used in one or more embodiments is to use a Kalman filter (or a variation of a Kalman filter like an Extended Kalman Filter or an Unscented Kalman Filter). FIG. 13 illustrates an example that uses this approach. Kalman filter 1301 incorporates a kinematic model 1302 of the bat 102. The system state 1303 is estimated for each sample point, and this estimate is corrected based on measurements 1304. The state 1303 for example may include the position r(t) and the orientation Q(t) of the bat, and the measurements 1304 may include for example accelerometer values $a_x$, $a_y$, $a_z$ and gyroscope values $\omega_x$, $\omega_y$, $\omega_z$. During time intervals when one or more measurements are not available or are saturated, such as x-axis angular velocity 1306 during time interval 1105, the filter 1301 continues to predict state values 1303. Therefore, the curve 1104 can be extrapolated to curve 1308 through interval 1105; for example, the orientation 1307 may be differentiated to estimate the x-axis angular velocity 1308 in this interval.

In general, one or more embodiments may use a recursive state space estimator (e.g., Kalman filter) with a kinematic model of the physical body or equipment being measured. The state-space propagation model may be used to impose appropriate physical constraints. The state space estimate and its uncertainty (covariance) may be updated using the non-saturated measurements from the various sensors. An estimate of the missing (saturated) parameter may then be derived from the state space estimate. Likewise, the uncertainty in the estimated parameter may be derived from the model uncertainty. Either the state space propagation model or the measurement model (or both) may be non-linear, in which case a linearized (EKF) or sigma-point (UKF) filter may be used. Finally, the uncertainty in the extrapolated time series (or the state space estimate itself) may be propagated to derived metrics. For example, in a baseball swing like the swing illustrated in FIG. 13, the gyroscope may be saturated into impact, which affects the accuracy of the swing speed measurement. Using this approach, it is possible to estimate the actual swing speed and provide an uncertainty interval (error bars).

Figure 14:
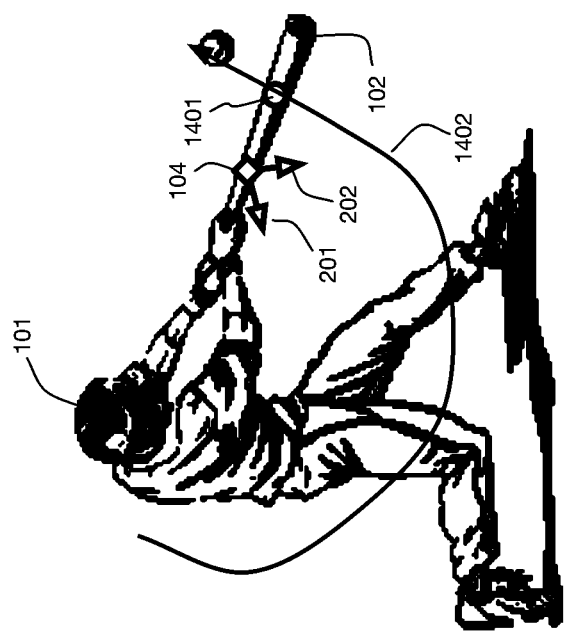
FIG. 14 illustrates an embodiment that tracks the trajectory of the sweet spot of a bat and that calculates swing metrics from this sweet spot trajectory.

In one or more embodiments, a swing of a bat or similar equipment may be decomposed into key events and metrics that provide insight into overall swing quality. Some of these events and metrics may be related to or derived from the trajectory of a sweet spot of the bat. FIG. 14 shows an illustrative swing of bat 102 by batter 101. The bat is equipped with a sensor 104, which may for example include a motion sensor with an accelerometer and a gyroscope. One or more embodiments may obtain sensor data from sensor or sensors 104, and may use this sensor data to calculate the trajectory 1402 over time of sweet spot 1401 of the bat through all or a portion of the swing. The sweet spot location on a bat may be determined by any desired method. For example, several common definitions for the sweet spot of the bat are that it produces the maximum energy transfer to the ball, that it produces the maximum batted ball speed, or that it results in the least vibrational sensation (sting) in the player's hands. These results are not always produced by the same spot on a bat. In addition, the spot may vary based on bat type (wood or aluminum), weight, shape, and other factors. For a more in-depth discussion of the definition, size, and location of the sweet spot for different bat types, see for example Daniel A. Russel, "Physics and Acoustics of Baseball and Softball Bats."

In one or more embodiments, an illustrative definition of a sweet spot may be a location somewhere between four and eight inches from the tip of the bat, such as for example a single point on the centerline of the bat six inches from the tip.

Figure 15:
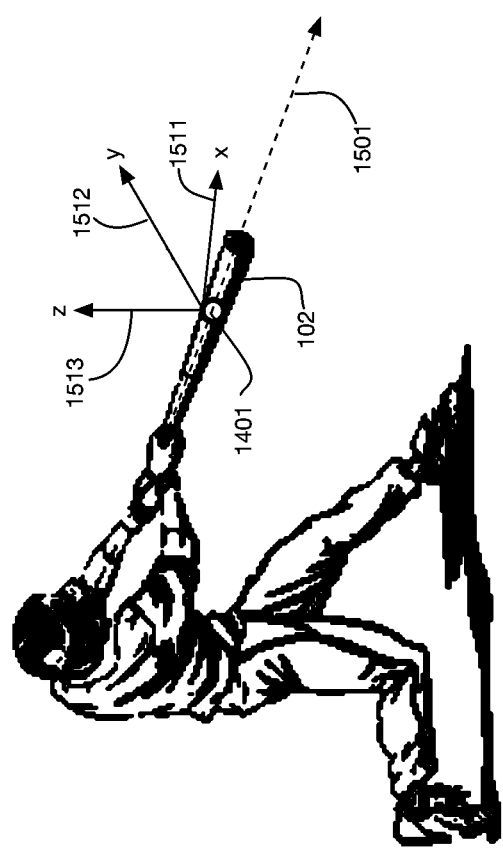
FIG. 15 illustrates a reference frame used in one or more embodiments to measure bat motion and to calculate swing metrics; this reference frame has the origin at the sweet spot, a vertical z-axis, and the bat is in the xz-plane at impact.

In one or more embodiments, data from sensor 104 may be integrated or otherwise analyzed to estimate the sensor velocity and position in an inertial (world) coordinate frame. The known position of the sweet spot relative to the sensor may then be used to calculate the sweet spot trajectory 1402 in this reference frame. In one or more embodiments, the world reference frame may be defined as illustrated in FIG. 15, which shows the bat at the point of impact with a ball (or at another point in time defined as a real or virtual time of impact). The origin of the reference frame is at the sweet spot of the bat 1401 at the moment of impact. Gravity is in the −z direction; hence the z axis 1513 points vertically upward. The world coordinate system is not based on an absolute horizontal reference point such as home plate or absolute north. Instead, the world frame is rotated so that the bat longitudinal axis 1501 is in the xz plane pointing in the +x direction 1511 (for right handed batters) or −x direction (for left-handed batters). The forward velocity of the bat is in the yz plane pointing in the +y direction 1512. Because of this definition, the actual orientation of the world coordinate frame will vary from swing to swing.

Figure 16:
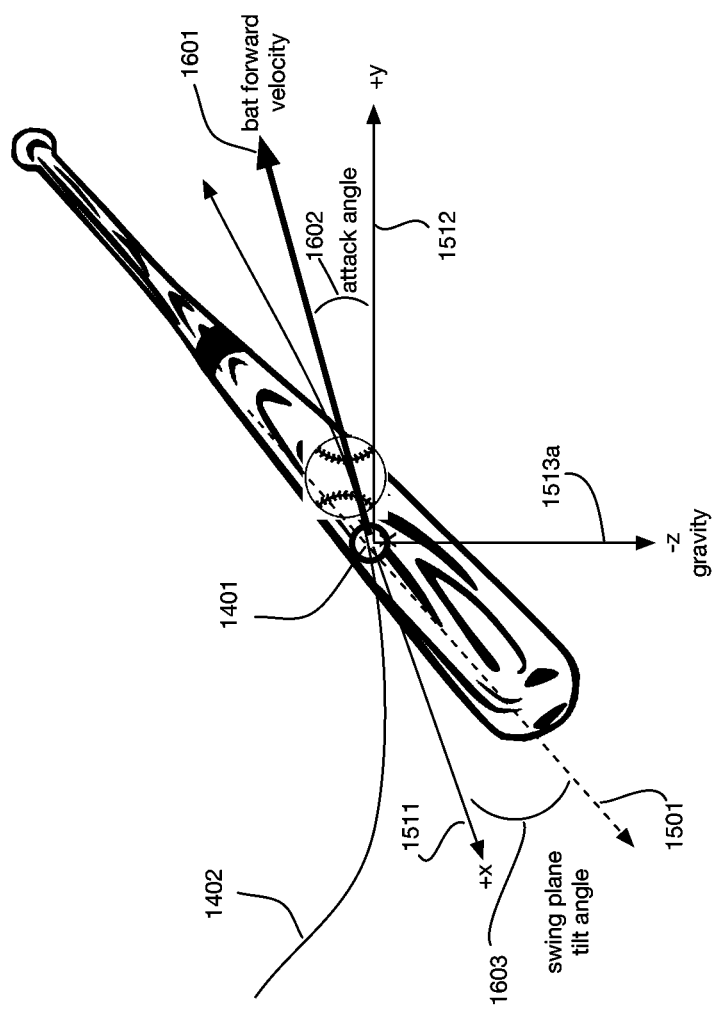
FIG. 16 shows another view of the reference frame of FIG. 15, and illustrates several swing metrics including the bat forward velocity at impact, the attack angle, and the swing plane tilt angle.

FIG. 16 shows a close-up view of the reference frame illustrated in FIG. 15, shown again at the point of impact of the swing. The reference frame origin is the location 1401 of the sweet spot of the bat at impact. The −z axis 1513a is in the direction of gravity, pointing vertically downward. Bat longitudinal axis 1501 is in the plane defined by the x axis 1511 and the −z axis 1513a. The y-axis 1512 is perpendicular to the x-axis and to the z-axis. In general, the bat may not be horizontally level at the time of impact; instead there may be a nonzero angle 1603 between the bat axis 1501 and the (horizontal) x-axis 1511, which is referred to as the vertical bat angle. Vertical bat angle is defined as the vertical direction of the bat with respect to horizontal at impact. Vertical bat angle is negative below horizontal and positive above horizontal. The swing plane tilt angle 1603 is the vertical bat angle at the moment of impact. The swing plane tilt angle is usually negative, meaning the bat is pointing toward the ground. A level bat would result in a swing plane tilt angle of 0°. Swing plane tilt angle is important for understanding adjustability and correlations to pitch types and locations. Pitch location will determine changes in the bat angle at impact. Adjusting the swing plane tilt angle to meet the pitch should be done early in the swing in order to achieve maximum efficiency. Adjustment later in the swing drains energy from the speed of the bat. The swing plane tilt angle should match the location of the pitch. Steeper angles are required for low, inside pitches, and shallower angles are required for high, outside pitches.

The velocity of the bat at impact may also in general not be horizontal; the attack angle 1602 is the angle of the bat's forward velocity at impact 1601 with respect to the horizontal y-axis 1512. Attack angle is negative below horizontal and positive above horizontal. A positive value indicates swinging up, and a negative value indicates swinging down, where zero is perfectly level. Attack angle is important for two reasons: First, matching the bat path to the pitch path increases the likelihood of contact. Because the pitch is thrown from an elevated mound, it is typically on a downward angle as it crosses the plate. Therefore, a positive attack angle provides more opportunity to execute against a variety of pitches, which vary in height, speed, and angle. Second, a positive attack angle will usually maximize launch distance, increasing the scoring value of the at-bat.

The average fastball crosses the plate at a 6° downward angle, while an average breaking ball crosses the plate at 10°. Other factors include swing speed and style, pitch velocity and location, and game situation. Given the variation in incoming pitch descent angles and desired launch angle, the optimal attack angle is usually between +2° to +14° degrees. In a real game scenario, adaptation may be required to put the ball in play. The ideal attack angle results in the maximum distance for a given bat speed. For slow bat speeds, the ideal attack angle is around 21°, and it gets smaller with increasing speed. Discussions of ideal launch angle, exit speed, and scoring value appear for example in Nathan, "Optimizing the Swing," at www.hardballtimes.com/optimizing-the-swing, and in Arthur, "The New Science of Hitting," at www.fivethirtyeight.com/features/the-new-science-of-hitting.

The bat forward velocity 1601 is the projection of the velocity vector of the sweet spot onto the plane perpendicular to the bat longitudinal axis 1501; it ignores any speed in the direction of the bat axis 1501.

Figure 17:
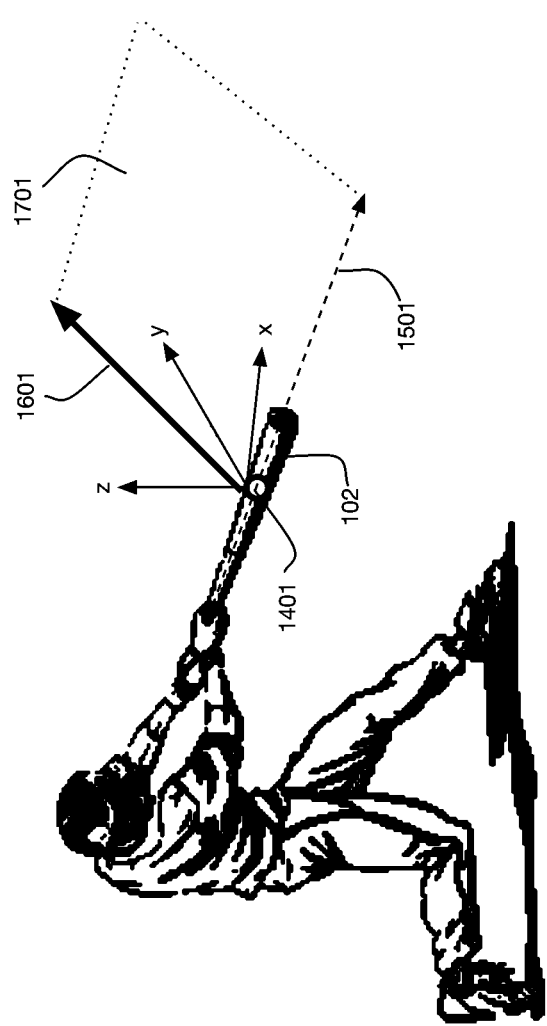
FIG. 17 shows a swing plane that is spanned by the bat's longitudinal axis and the velocity of the sweet spot at impact.

FIG. 17 illustrates a definition of a swing plane from which various swing metrics may be derived. Swing plane 1701 may for example be defined as a plane through the sweet spot 1401 which is spanned by the bat longitudinal axis 1501 at impact and by the bat forward velocity 1601 at impact. This swing plane is oriented so that it contains both the length of the bat and bat velocity at the moment of impact. The swing plane normal vector may found by normalizing the cross product of the bat length and bat velocity vectors. The normal vector is centered at the sweet spot of the bat at the moment of impact, i.e., at (0, 0, 0).

Figure 18:
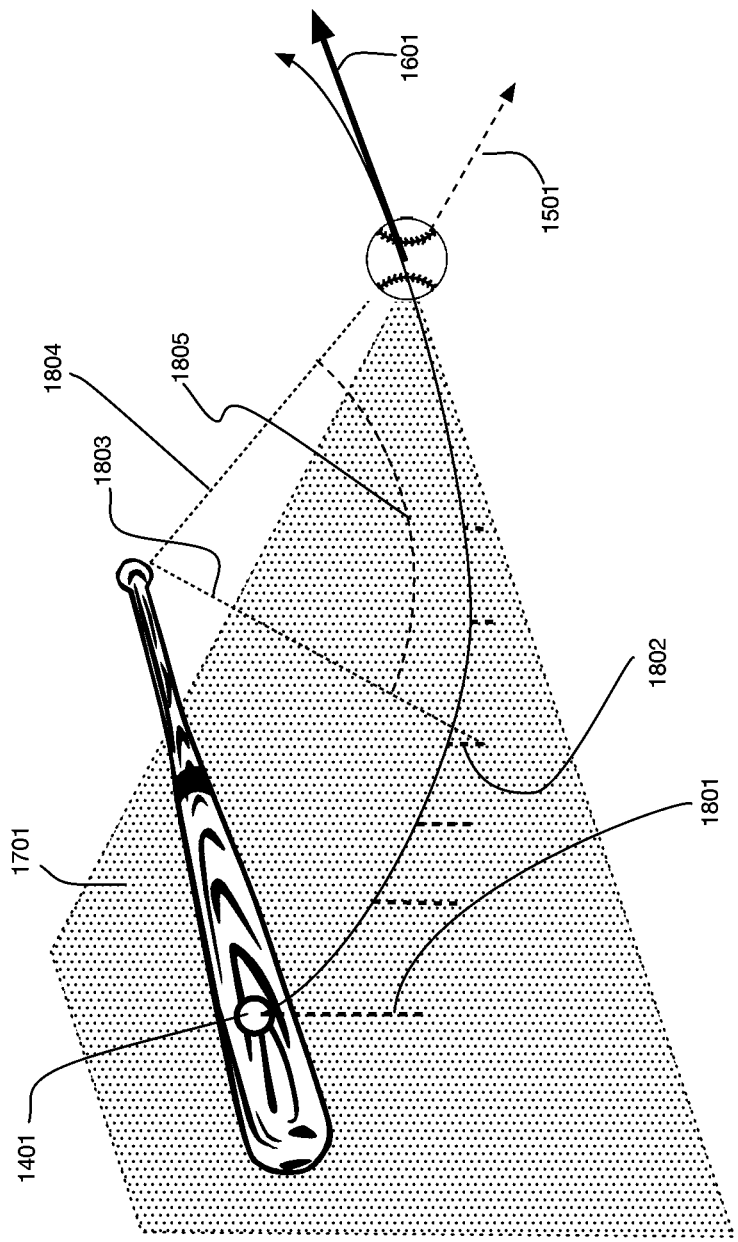
FIG. 18 shows the off-plane distance between the bat sweet spot and the swing plane during the swing, and it illustrates swing metrics that include the time when the bat is on-plane (within a specified threshold distance from the swing plane), and the on-plane metric that measures the angular range of motion while the bat is on-plane prior to impact.

A swing may be analyzed for example by decomposing the motion into swing plane versus off-plane components. Off-plane motion may for example be characterized by the distance of the sweet spot of the bat from the swing plane at any moment in time. FIG. 18 illustrates this distance of the sweet spot 1401 to the swing plane 1701 at several points in a swing prior to impact. For example, at the position of the bat shown in the figure, the off-plane distance is 1801. As the swing progresses towards impact, the sweet spot approaches more closely to the swing plane 1701. When the distance reaches a specified threshold 1802, the swing is considered "on-plane" at that moment (provided that it remains at or below this distance from that moment until impact). For example, the threshold may be set to 3 inches.

Based on the distance between the sweet spot and the swing plane, an on-plane metric may be defined as the total angular range of motion (for example in degrees) of the swing where the sweet spot of the bat is within the threshold value (such as three inches) from the swing plane. For example in FIG. 18 the on-plane metric is the angle 1805 between the ray 1803 at the on-plane event and the ray 1804 at the impact event. This metric measures an aspect of the quality of the swing because the player typically wants the energy from the body and arms to increase forward bat speed rather than change its direction. Changing bat direction takes more energy as bat speed increases, so an efficient swing gets on plane early and stays on plane as it approaches impact. Ideally, a batter will read the pitch early and adjust the entire body to align the swing plane with the pitch location. This enables maximum bat speed for every pitch type. In one or more embodiments, the system may report the percentage of total velocity that is generated while the bat in on plane. For example, if the velocity is 40% of the peak when the bat gets on plane, then the "on plane" metric is 60%.

Figure 19:
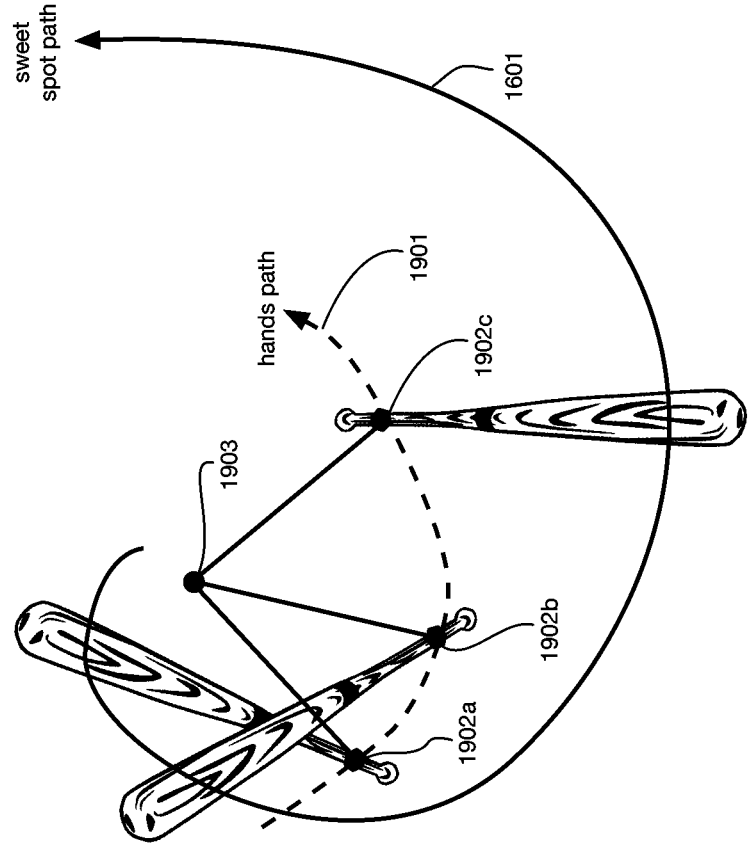
FIG. 19 illustrates an embodiment of a center of rotation calculation, which determines a point equidistant from the hand position on the bat at multiple points on the swing.

One or more embodiments may analyze the motion of a position on the bat where the hands grip the bat, in addition to or instead of analyzing the motion of the bat sweet spot. FIG. 19 illustrates an embodiment that determines a center of rotation 1903 for a swing by determining the position of the hands at three points in the swing, at location 1902*a*, 1902*b*, and 1902*c*. The center of rotation is selected for example as the point 1903 that is equidistant from these three points. One or more embodiments may use any point or points on hands trajectory 1901 to determine one or more centers of rotation for the swing. For example, point 1902*a* may be selected as the time when the xy magnitude of the gyroscope value from the sensor is at 50% of its impact value; point 1902*b* may be selected as the time when the xy magnitude of the gyroscope value is at 80% of its impact value; and point 1902*c* may be selected as the impact time. Using the hand positions at these times, the center of rotation may be calculated using the formula for the circumcenter of a triangle defined for example in en.wikipedia.org/wiki/Circumscribed_circle.

Three points on hands trajectory 1901 also define a plane, and therefore define an axis of rotation through the center of rotation 1903 that is perpendicular to that plane. The orientation of this axis of rotation may also be used in one or more embodiments as a metric describing the swing. The three points that define the center of rotation lie in a plane that is typically tilted downward in front of the body. The axis of rotation may be calculated for example using the cross product of any two of the radius vectors from the center of rotation calculation.

In one or more embodiments, a two-lever model may be used to describe and analyze a swing. During the early part of the downswing, an experienced batter rotates the core, arms, and bat as a single, connected unit. Then the batter commits by snapping the wrist, which moves the tip of the bat away from the body. The elbow may also extend, depending on ball location. This optimal kinematic sequence results in maximum speed and control.

The kinematic chain includes core, shoulder, elbow, and wrist rotation. In some situations, it may not be feasible to measure all these movements directly using, for example, a single inertial sensor on the bat. Instead, one or more embodiments may use a simplified two-lever mechanical model to distinguish "body" rotation from "bat" rotation. The body contribution ends at the hands. It measures rotation around the body center of rotation, which is primarily core, shoulder, and some elbow extension. The bat component measures motion around the hand position, which is primarily due to elbow and wrist rotation. In a connected swing, the shoulder and elbow contributions are small, and the body component of our model closely approximates core body rotation.

Figure 20:
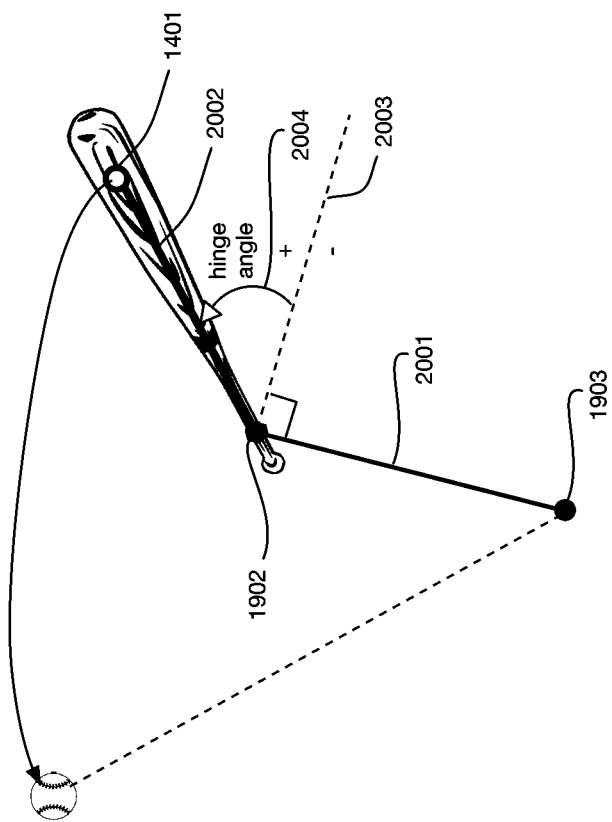
FIG. 20 illustrates a two-lever model of a swing that is used to calculate swing metrics such as a hinge angle between a bat lever and a body lever.

FIG. 20 illustrates a swing model that employs a simple two-lever mechanical system. This model focuses on the swing-plane and ignores any off-plane motion, which is characterized independently. The body lever is hinged at the body center of rotation and ends at the hand position. The bat lever is hinged at the hand position and extends along the axis of the bat. This model is illustrated in FIG. 20. Body lever 2001 extends from center of rotation 1903 to hand position 1902, and bat lever 2002 extends from hand position 1902 to sweet spot 1401.

Total bat speed is a combination of body rotation and bat rotation. The body ratio may be calculated the percentage of total rotation that is attributed to the body. An efficient swing uses both the body, arms, and wrists in the appropriate kinematic sequence. A swing that is mainly body rotation or mainly arm rotation is not as powerful as a swing that uses the entire kinematic chain. The body should contribute about 40% to 50% of the total rotational speed. There may be some variation due to individual style, but a value that is consistently outside this range usually indicates a poor kinematic sequence.

As the bat moves through the swing, the angle between the bat lever and the body lever changes. An angle that reflects the relative orientation of the bat lever and the body lever is called the hinge angle. In the illustrative embodiment shown in FIG. 20, the hinge angle 2004 is the angle between the bat lever 2002 and the tangent 2003 that is perpendicular to the body lever 2001 in the two-lever mechanical model. Hinge angle is negative when the tip of the bat is angled toward the body and positive when the tip is angled away from the body.

One or more embodiments may incorporate a method of calculating a commit event. The commit event, also known as wrist release, occurs when the hinge angle is "released". In other words, the moment when the hinge angle starts to move in a positive direction away from the body. Commit is the transition point in the kinematic chain between body-only motion and the wrist snap contribution. A batter begins the swing with the bat angled towards the body. At commit, this hinge angle is released and the wrist is snapped forward to add speed to the bat and to contact the ball.

Figure 21:
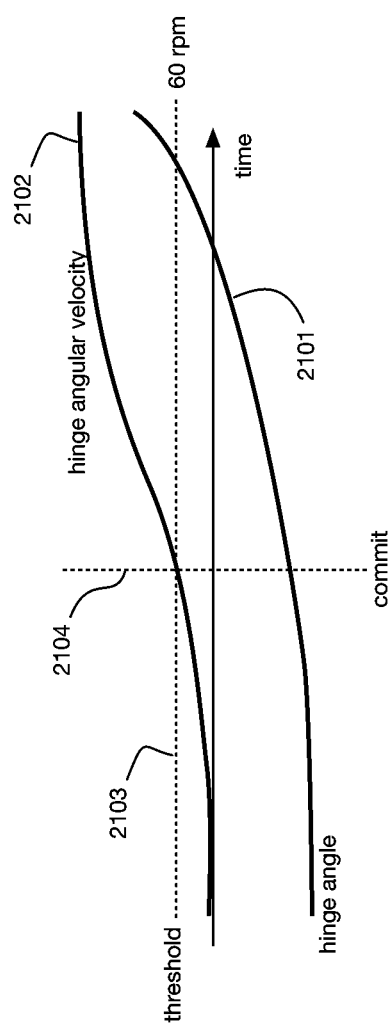
FIG. 21 shows a calculation of a commit event that may represent, for example, when the wrist snaps to release the bat from a cocked orientation to complete a swing.

FIG. 21 illustrates a method of calculating a commit event that may be used in one or more embodiments. The hinge angular velocity 2102 may be found by taking the first derivative of the hinge angle time series 2101. Any desired method may be used to calculate or estimate a derivative; for example, one or more embodiments may use a centered, five-sample window to reduce sample noise. The commit event 2104 may be defined as the instant when the hinge angular velocity 2102 exceeds a threshold value 2103 prior to impact. For example, a threshold value of 60 rpm (360 dps) is illustrated in FIG. 21.

Figure 22:
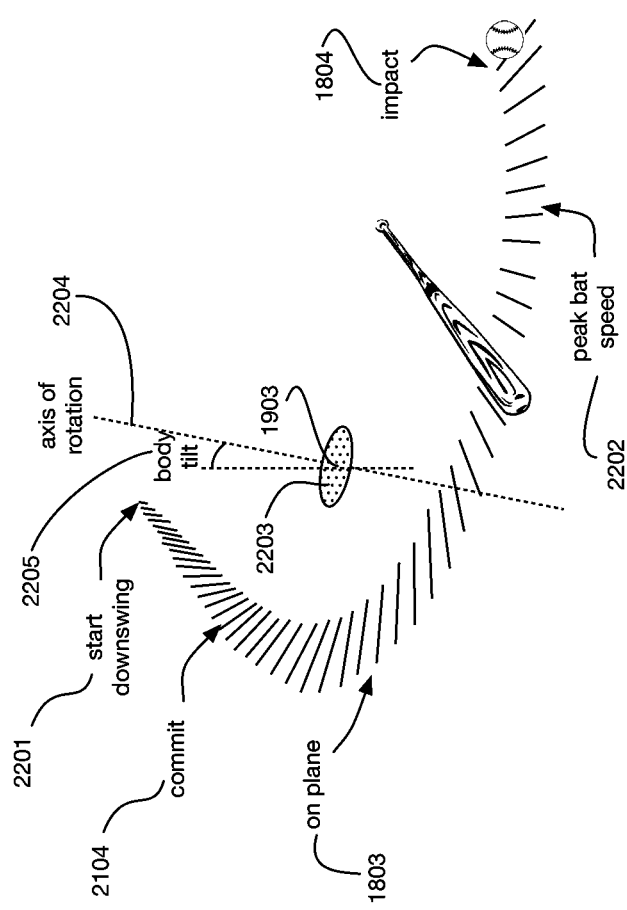
FIG. 22 shows an illustrative swing trajectory with several swing events annotated along the trajectory; it also illustrates a swing axis of rotation and a body tilt metric derived from this axis of rotation.

One or more embodiments may define a sequence of events through a swing, and may derive one or more metrics from these events. FIG. 22 shows an illustrative swing with events annotated at the point in the swing when they occur. Event 2201 is the start of the downswing of the swing. Start of downswing indicates the start of significant motion of the downswing. An illustrative algorithm that may be used in one or more embodiments to calculate the start of downswing is as follows. Start of downswing is calculated by looking at the gyro xy resultant time series. Starting from the peak value, work backwards one sample at a time. For each sample, fit a straight line through the peak value and the sample of interest. Find the moment in time where this straight-line approximation crosses through zero angular velocity. This is an estimate of the start of downswing. Repeat this for every sample until the angular velocity of the sample of interest is less than 10% of the peak value. Keep the latest start of downswing estimate that was found during this search. This start of downswing algorithm uses the xy resultant, which is a better proxy for overall bat motion than, for example, using only the y component of motion. The model-based algorithm also provides more consistent estimates than a threshold-based or zero-crossing algorithm. By fitting a model to the overall shape of the angular velocity curve, the algorithm ignores meaningless hand motion near the start of downswing, where the signal is on the same order of magnitude as the noise. In one or more embodiments, the angular velocity curve is decomposed into two additive components, body lever and bat lever, and a metric is derived therefrom and optionally reported to the user and/or utilized for internal calculations. In some embodiments, other metrics may also be reported including measuring and comparing two parts (body and bat rotation) and utilizing peak speed ratios, amount of rotation ratios, peak angular velocity ratios, centripetal acceleration, i.e., how quickly a user starts accelerating a bat through body rotation to form metrics. Another metric may be formed by dividing peak hand speed by peak bat speed or an average of the hand speed and bat speed from commit to impact to reduce variability in the measurement. In one or more embodiments, any of these metrics or any other metrics defined herein may be provided to the user through sound, for example if over, equal to, or under a predetermined threshold, or via a visual display, or AR/VR/MR display (or through both audio and visual) to provide the user with biofeedback for use by the user to observe and/or alter position, posture, swing.

Commit event 2014, also known as wrist release, occurs when the hinge angle is released, as described with respect to FIG. 21.

The on-plane event 1803 occurs when the sweet spot approaches to within a threshold (such as three inches, for example) of the swing plane, as described with respect to FIG. 18.

For a swing that hits a ball, impact event 1804 occurs when the bat hits the ball and when this impact is detected by the sensor or sensors. One or more embodiments may also detect a virtual impact event even when the bat does not hit a ball (for example, for an "air swing"), as described below.

For embodiments with an accelerometer, a simple impact detection may be performed by searching for a large discontinuity in accelerometer readings, corresponding to the shock of the impact. However, certain batters generate accelerometer noise greater than 4 g prior to true impact. This has been observed in internal testing and in pro-level swings. Analysis shows that this noise is almost always associated with high bat roll (z-axis angular velocity). Presumably, the bat is slipping in the grip, and the noise is caused by friction of the bat against the hands or gloves. Therefore, in one or more embodiments, the impact detection algorithm may use both the gyro and accelerometer to detect impact. The gyro search detects impact energy that is spread out over one or more subsequent samples. Searching forward, keep a running sum of the maximum gyro x, y, or z discontinuity. Reset the sum to zero if the discontinuity drops below 540 dps and remember that sample. Stop searching if the total discontinuity exceeds 1040 dps. The gyro-only impact is the last sample that was remembered.

Starting from the gyro-only impact sample, search backward until the accelerometer x, y, or z discontinuity is less than a threshold (80% of the saturation value). Usually, this occurs zero or one samples prior to the gyro-only impact, but sometimes it can more. Impact is defined as the sample just before the accelerometer discontinuity.

In rare cases, there is insufficient energy in the gyro signal to detect impact. In this case, impact is the defined as the sample just before the first accelerometer discontinuity that exceeds the threshold.

In one or more embodiments, air swings are supported by enabling an air swing version of the impact detection algorithm. If the system does not detect an impact event, the baseball swing processor determines whether the swing is a valid air swing. The air swing detection algorithm may for example look for peaks in the gyro xy resultant and accelerometer z component. A swing may be classified as a valid air swing if for example: the gyro xy peak exceeds 500 dps; the accelerometer z component peak exceeds 4 g; and the two peaks occur within 100 ms. In the case of a valid air swing, the time of the gyro xy peak may be used as a proxy for the impact event in all subsequent calculations. Processing of air swings continues the same as for impact swings. All swings may be considered invalid if the air swing criteria are not met, even if there is a valid impact signature.

Peak bat speed event 2202 occurs at the moment of maximum forward bat speed, which happens at or before the moment of impact. Peak bat speed is calculated using the forward bat speed time series. Working backwards from impact, peak bat speed is located by finding the sample with the peak value.

Average power generated during the swing may be calculated as power=mass×speed×acceleration, where mass is the effective mass of the bat, speed is the bat speed at impact, and acceleration is the average acceleration during the downswing (bat speed/time to contact). Power may be measured in Watts. The more mass the batter accelerates to high speed, the higher the power.

Based on the start of downswing event 2201 and the impact event 1804, a time to contact metric may be calculated as the elapsed time between start of downswing and impact. The clock starts when there is sufficient downswing motion and ends when the bat contacts the ball (or at a corresponding virtual impact event for an air swing). Time to contact measures the total time it takes to complete a swing. A major league fastball takes about 400 milliseconds from pitcher to home plate. In that time, the batter must recognize the pitch, decide whether to commit, and execute the swing. The quicker the time to contact, the more time the batter has to recognize and commit to good pitches. The ideal time to contact depends on age, strength, bat length and weight, experience level, and swing style. Our testing shows the typical time to contact for different age groups and skill levels: Little League: 230-400 milliseconds; Senior League: 185-325 milliseconds; High School: 140-260 milliseconds; College/Pro: 100-200 milliseconds.

FIG. 22 also illustrates metrics related to the orientation of the swing. For example, axis of rotation 2204, which is perpendicular to plane 2203 spanning points on the hand trajectory and is through center of rotation 1903, forms a body tilt angle 2205 with the vertical axis. The center of rotation is a point at the center of the arc traced by the hands and is usually near the body's center of rotation. The axis of rotation is the axis that the body rotates around and is usually aligned with the spine. The body tilt angle is the angle between the axis of rotation and vertical. The body and bat should rotate around the same axis. A large difference between the swing plane tilt angle and the body tilt angle is an indication of a disconnected swing. In an efficient swing, the swing plane tilt angle and body tilt angle should be closely-aligned.

Figure 23:
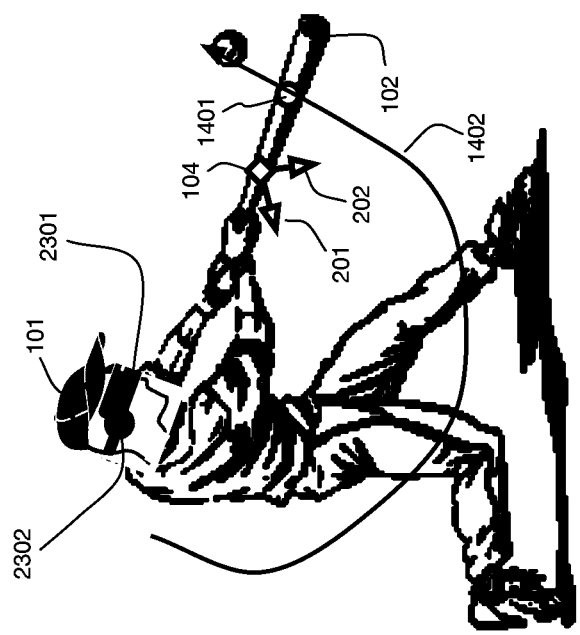
FIG. 23 shows an embodiment that provides bio-feedback to the user for setting posture or position or swing or any combination thereof via sound or AR/VR/MR visual displays, that enables working on postures, positions, swings and detecting proper or improper postures, positions, swings or portions thereof and to improve power and/or efficiency and to enable rehabilitation.

FIG. 23 shows an embodiment that provides bio-feedback to the user for setting posture or position or swing or any combination thereof via sound or AR/VR/MR visual displays, that enables working on postures, positions, swings and detecting proper or improper postures, positions, swings or portions thereof and to improve power and/or efficiency and to enable rehabilitation. One or more embodiments of the invention may include utilizing sound, e.g., via headphones 2302, or at least one Virtual Reality (VR), Augmented Reality (AR) or Mixed Reality (MR) display, glasses or goggles 2301 to provide bio-feedback to the user. In one or more embodiments the audio and/or image components 2301 and/or 2302 may be coupled with or formed into a helmet, such as a batter's helmet for example. This enables the user to see the pitch approach, wherein the headset tracks the ball coming to provide metrics, and after the ball is hit, the system provides the user with the hitting metrics and/or a 3D tracer overlay, for example of the swing. MR is also referred to as "hybrid reality" and includes use of real and virtual data to produce novel environments and visual displays that include real and computed objects and interact, which also may include real-time display of data. For example, in one or more embodiments, a sound or visual display may be utilized to provide feedback to the user to indicate a correct position, or movement has been achieved. This enables a user to work on portions of a swing or an entire swing using different body positions, for example to simulate different feet positions in a sand trap for a golf swing for example and obtain feedback regarding the position and/or swing using sound or visual feedback. In addition, by providing metrics regarding the body position, body movement, piece of equipment position, piece of equipment movement or any combination thereof, embodiments of the invention enable a user to work on developing more power and improving skills in a bio-feedback environment and/or combine environment. Embodiments of the system also enable rehabilitation and general training of the body based on the data gathered by the system to suggest areas of the body to strength or stretch to improve the range of motion to avoid injury through use of correct biomechanics.

Figure 24:
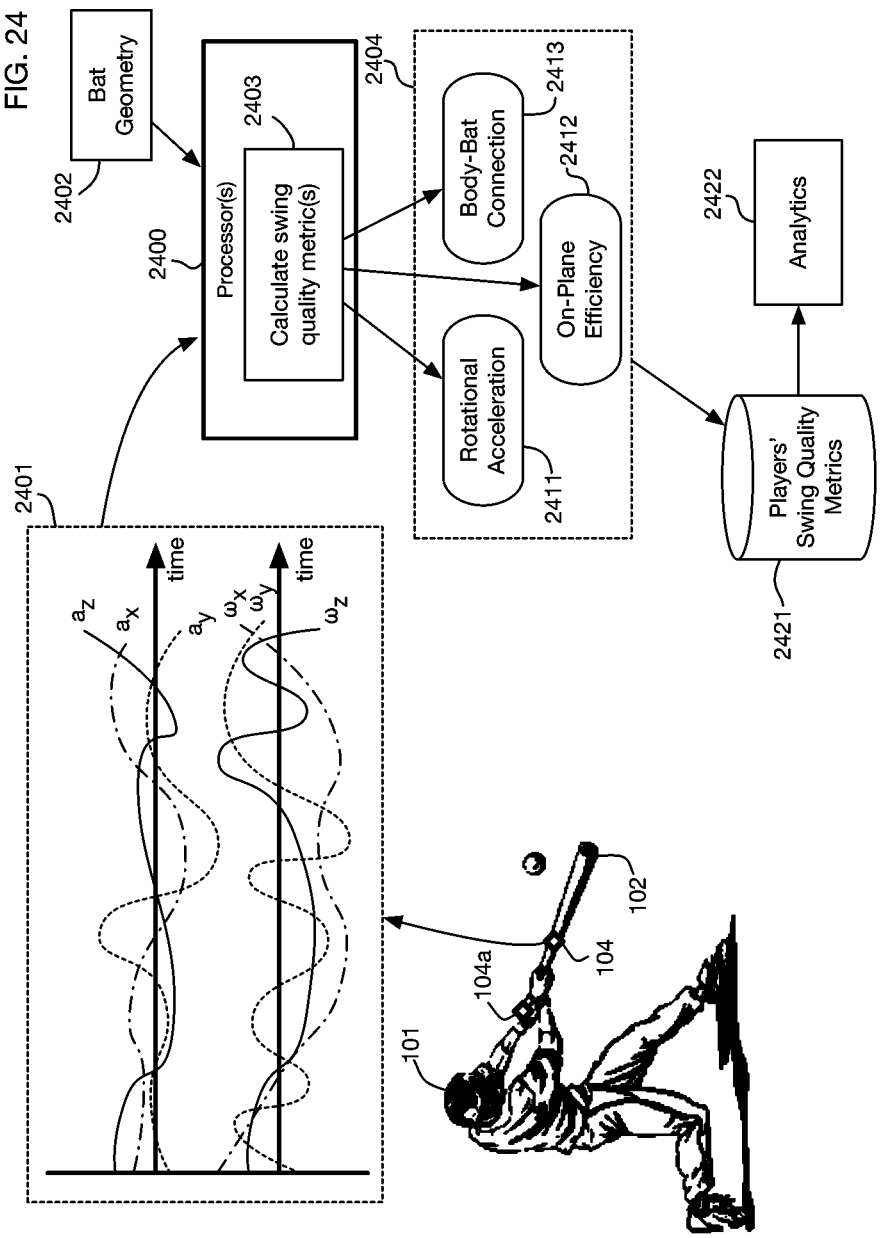
FIG. 24 shows an embodiment of the invention that calculates several swing quality metrics from acceleration and angular velocity data captured by an inertial sensor on a bat; illustrative swing quality metrics include rotational acceleration, on-plane efficiency, and body-bat connection.

One or more embodiments of the invention may include components that enable calculation of various swing quality metrics for a swing of a baseball bat, softball bat, or other equipment. Based on extensive analysis of swing data and swing biomechanics, the inventors have identified three swing quality metrics that appear to be valuable high-level summaries of how effectively a user swings a bat. One or more embodiments may extend or modify these three swing quality metrics in any desired manner. The three swing quality metrics described below are rotational acceleration, on-plane efficiency, and body-bat connection. A system that calculates these metrics is illustrated in FIG. 24. User 101 swings a bat 102 to hit a ball. An inertial sensor 104 is installed on bat 102. The sensor 104 may include for example a three-axis accelerometer and a three-axis gyroscope. Data 2401 may be transferred from inertial sensor 104 to a processor 2400, for example over a network connection. The processor may be for example a mobile device such as a smart phone or a laptop, or any other computer such as a desktop or server computer. In one or more embodiments the processor may be a network of multiple processors. In one or more embodiments the processor or a portion of the processor may be integrated into the inertial sensor 104.

Embodiments of the invention may not include all of the components shown in FIG. 24. For example, one or more embodiments may not include the inertial sensor 104, but may instead receive data 2401 generated by another inertial sensor or similar device. One or more embodiments of the invention may not include processor 2400, but may include software that executes on this processor to analyze data 2401.

Data 2401 may include a time series of acceleration data captured by an accelerometer, and a time series of angular velocity data captured by a gyroscope. The accelerometer and gyroscope may have three axes, and the time series may each have three sub-series for each of the three axes. Processor 2400 may also access a bat geometry definition 2402, which may for example describe physical characteristics of the bat 102. Based on the acceleration and angular velocity time series 2401, and the bat geometry 2402, the processor or processors 2400 may execute one or more steps 2403 to calculate one or more swing quality metrics 2404. These metrics may include any or all of rotational acceleration 2411, on-plane efficiency 2412, and body-bat connection 2413. The swing quality metrics 2404 may include other metrics in addition to these three metrics, or a subset of the metrics shown. Data and metrics from multiple batters may be captured in a database 2421, and analytics 2422 may be generated from this database. These analytics may for example be used to optimize batting orders, to improve individual players' swings, to assign exercise programs, to assist with recruiting, to match players to coaches, or to plan pitching strategies or adjustments.

One or more embodiments may have or use sensors instead of or in addition to inertial sensor 104 on bat 102. For example, FIG. 24 shows optional inertial sensor 104a on one of the hands of batter 101, for example in a batting glove; this sensor may capture data on motion of the hands. Sensors may be installed on any part or parts of the batter's body or on or in any equipment, such as on a belt, cap, or shoes. Data from these sensors may be fused with data from bat sensor 104 to analyze and characterize the swing.

FIG. 24A shows an embodiment of the invention that uses video camera data instead of inertial sensor data to track the motion of the bat. The sensors of FIG. 24 (inertial) and FIG. 24A (video) are illustrative; one or more embodiments may obtain bat motion data or motion data on other items such as the batter's hands using any type or types of sensors, including but not limited to inertial sensors and video camera sensors. Sensor data from any sensor or sensors may include or may be transformed to acceleration and angular velocity data 2401, which in turn may be used to calculate swing quality metrics.

In FIG. 24A, three video cameras 2431, 2432, and 2433 capture images of the swing of bat 102 by batter 101. One or more embodiments may use any number of video cameras. A potential benefit of using multiple cameras it that the bat may be visible at any point in the swing from at least one camera. In this illustrative embodiment, no sensor or marker is placed on bat 102 (or on player 101). Although markers may facilitate motion tracking using video images, in some situations they may be awkward or time-consuming to use; therefore, one or more embodiments may use markerless motion tracking using analysis of video images only without markers. Video streams from cameras 2431, 2432, and 2433 are combined into image sensor data 2435, which consists of a time sequence of frames from each camera. These frames 2435 are input into a step 2440 that generates the bat acceleration and angular velocity time series 2401 by analyzing the changes in the images over time. Techniques for tracking objects in video frames without markers are known in the art, as are techniques for generating data such as acceleration and angular velocity from the tracked object positions in frames. These techniques are used for example in markerless motion capture systems that recreate 3D motion from a series of 2D video streams, without attaching markers to the objects of interest. Image processing and recognition techniques may be used for example to identify the bat (or portions of the bat that are visible) in each frame, and stereo or multi-view triangulation may be used to recover 3D positions of the bat's points from the 2D projections of the bat in each frame.

Step 2440 of calculating acceleration and angular velocity from the video frames 2435 may be performed by processor or processors 2400, or by any other system or systems. For example, in one or more embodiments the cameras 2431, 2432, and 2433 may perform all or part of this processing internally. Processor 2400 may either obtain acceleration and angular velocity data 2401 directly from a sensor, or it may calculate this data from one or more sources of sensor data from one or more sensors of any type or types. Sensor data in this context may represent any data that represents or reflects motion of any object, including but not limited to inertial sensor data, video camera frames, or combinations thereof. One or more embodiments may combine data from inertial sensor 104 and cameras 2431, 2432, and 2433 (or other arrangements of one or more cameras) and may perform sensor fusion to calculate data 2401.

In one or more embodiments of the invention, sensor measurements, metrics and calculations such as those illustrated in FIGS. 24 and 24A may be applied to movements other than the swinging of a bat. For example, without limitation, calculation 2403 of quality metrics 2404 from inertial or video data may be applied to movements such as a golf swing, a tennis racket swing, a hockey stick shot, a lacrosse stick shot, or to movements without stick-like equipment such as a basketball shot, a soccer shot, a volleyball hit, a jump, a spin of a figure skater, or a baseball pitch or throw. Any type of motion may be analyzed with respect to a natural plane of rotation for that motion or an axis of rotation for the motion. The quality of the motion may be summarized in one or more quality metrics, such as metrics that capture the acceleration of the motion, the connection between the body of the person performing the motion and any equipment or other body parts involved in the motion or between different body parts involved in the motion, and the efficiency of the motion with respect to the natural plane for the motion. As an example, connection metrics for a spin of a figure skater may measure how the skater extends his or her arms or legs during the spin, or how the arm and leg positions relate to each other or to the body orientation. Quality metrics may be calculated from inertial sensor data or data from any other sensor on equipment or on the user's body, or they may be calculated from analysis of video captured during the motion. In one or more embodiments, metrics and calculations may also measure the stress on one or more joints of the user during the motion; these stresses may be related to the motion quality metrics since efficient motions may generate less stress on the joints.

An illustrative bat geometry definition 2402 is shown in FIG. 25. This bat geometry includes the location of a hand position 2501 on the bat 102, and a position of a sweet spot 2502 on the bat 102. These positions may be located for example along the longitudinal axis 210 of the bat. Positions may be measured for example relative to a position 2500 of the inertial sensor 104 on the bat. In one or more embodiments the positions 2501 and 2502 may be set to any convenient locations; they may or may not match actual hand positions of a specific real batter or a physical sweet spot position of a bat. They may be set to average values or typical values, for example. Typically, but not necessarily, the hand position 2501 may be near the knob end of bat 102, and the sweet spot position may be at or near a position that is an optimal spot on the bat for contacting a ball. An optimal position for contacting a ball may correspond for example, without limitation, to a position that maximizes energy transfer, a position that maximizes ball speed, or a position that minimizes vibration when the bat hits the ball at this position along the longitudinal axis 210. The bat geometry definition 2402 or any portions of this definition may be for example stored in memory on the inertial sensor 104, or it may be stored in any memory accessible to the processor such RAM, ROM, or a hard disk containing a file or database. A simple bat geometry definition file may contain for example only two numbers: the distance between points 2501 and 2500, and the distance between points 2502 and 2500.

Figure 26:
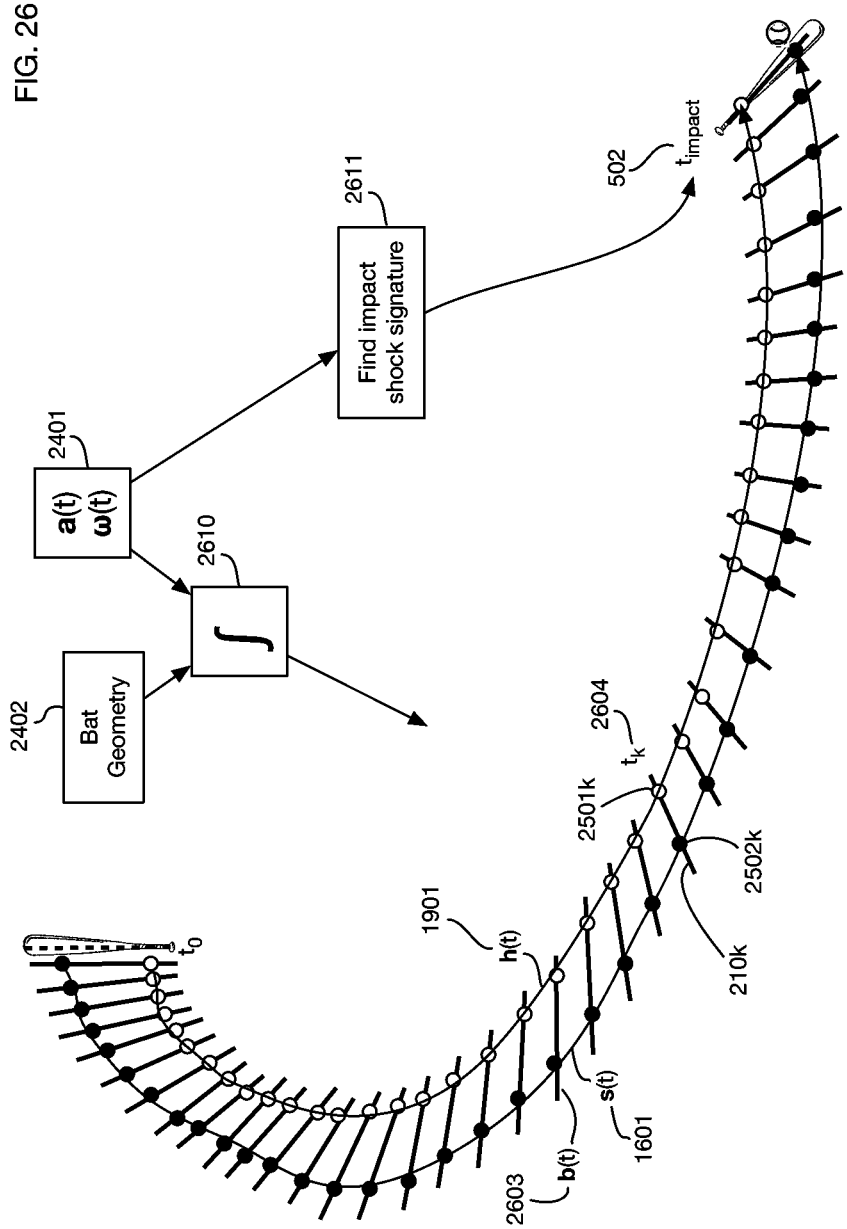
FIG. 26 shows illustrative processing steps that may be used in one or more embodiments to calculate swing quality metrics; these steps may include integrating acceleration and angular velocity data, detecting impact, and calculating trajectories of bat orientation and of the positions of the hands and the sweet spot on the bat.
Figure 27:
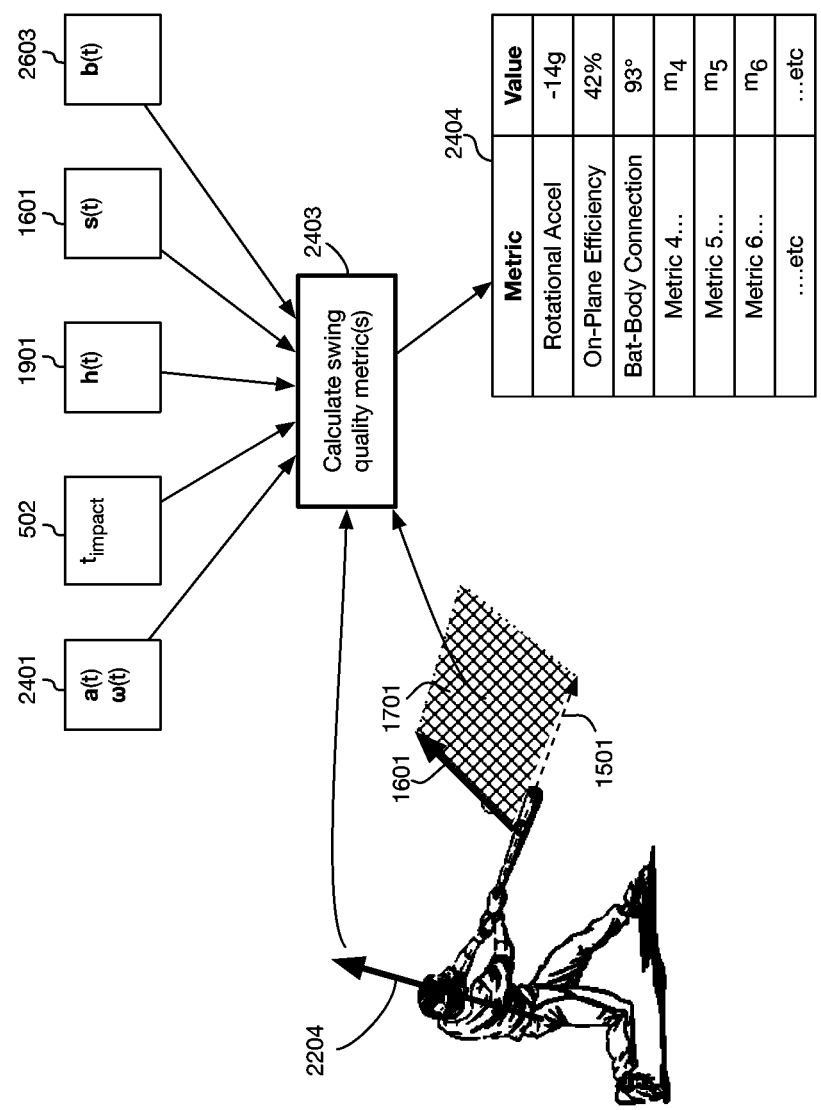
FIG. 27 expands on the flowchart of FIG. 26 to show additional data that may be calculated to determine swing quality metrics, including a swing plane and a body tilt axis.

One or more embodiments may perform several preliminary calculations before or during the generation of swing quality metrics. FIGS. 26 and 27 show illustrative calculations that may be performed in one or more embodiments. In FIG. 26, the acceleration and angular velocity time series 2401 obtained from the inertial sensor or derived from camera image data may be integrated in step 2610 to determine the position and orientation of the sensor over time. Furthermore, the bat geometry 2402 may be used to calculate the position and orientation over time of the bat and of specific points on the bat. For example, the processor of the system may calculate a trajectory of the longitudinal axis of the bat 2603 at points in time through the swing. It may calculate a trajectory 1901 of the hand position on the bat at points in time through the swing. And it may calculate a trajectory 1601 of the sweet spot position on the bat at points in time through the swing. FIG. 26 shows an illustrative state of the bat at time 2604 in the swing, with bat longitudinal axis 210k, hand position 2501k, and sweet spot position 2502k at this time. The system may determine specific events of interest in the swing and may locate points in time in the sensor data time series 2401 that correspond to these events. In particular the system may perform step 2611 to locate the impact of the bat with a ball or other object, to find impact time 502.

FIG. 27 illustrates how the data calculated in the steps shown in FIG. 26 may be used in one or more embodiments to calculate swing quality metrics. The acceleration and angular velocity time series 2401, the impact time 502, the hand position trajectory 1901, the sweet spot position trajectory 1601, and the bat longitudinal axis trajectory 2603 may be analyzed in calculations 2403 to generate metrics 2404. Additional inputs to the calculations 2403 may include the swing plane 1701, and the body tilt axis 2204, which are described above with respect to FIG. 17 for the swing plane, and with respect to FIGS. 19 and 22 for the body tilt axis.

FIGS. 28 through 36 describe how the data shown in FIG. 27 may be used in one or more embodiments to calculate the illustrative swing quality metrics shown in 2404: rotational acceleration, on-plane efficiency, and bat-body connection.

Figure 28:
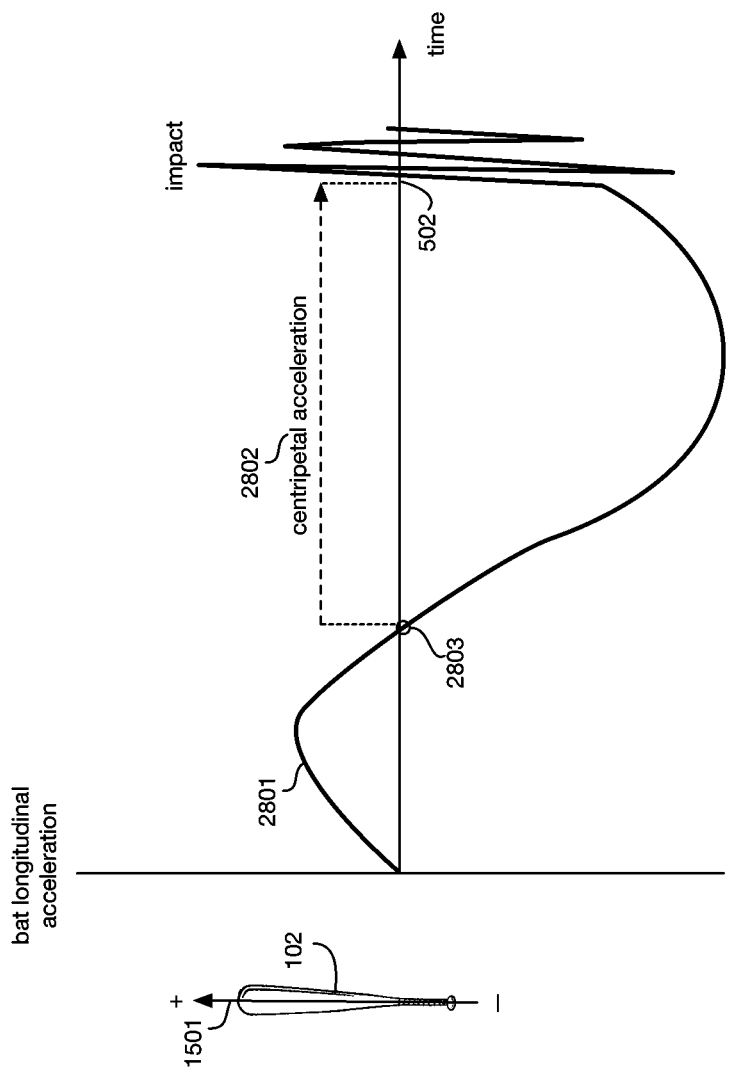
FIG. 28 illustrates determination of a final phase of a swing that corresponds to centripetal (negative) acceleration along a bat's longitudinal axis.

Turning first to rotational acceleration, one or more embodiments may separate a swing into a loading phase at the beginning of the swing, and a rotational phase when the batter completes the swing and accelerates to hit the ball. One method that may be used in one or more embodiments to define these two phases is to use the acceleration along the bat's longitudinal axis. This approach is illustrated in FIG. 28. The longitudinal axis 1501 of bat 102 is oriented so that the positive direction from the knob of the handle towards the barrel. An accelerometer on the bat may measure acceleration in this longitudinal direction, either directly if an axis of the accelerometer is aligned with this longitudinal axis 1501, or indirectly along multiple axes. In a typical swing, the batter adjusts the bat orientation in a loading phase, and then swings in an approximately circular motion. The circular motion results in centripetal acceleration along the longitudinal axis, which corresponds to a negative acceleration. FIG. 28 shows a plot of acceleration 2801 along the axis 1501. At time 2803 this acceleration changes sign, and it stays negative until impact 502. The phase 2802 of centripetal (negative) acceleration may be used to define the rotational phase of the swing. The point 2803 corresponding to the sign change may be used to define the transition between the loading phase of the swing and the rotational phase of the swing.

Figure 29:
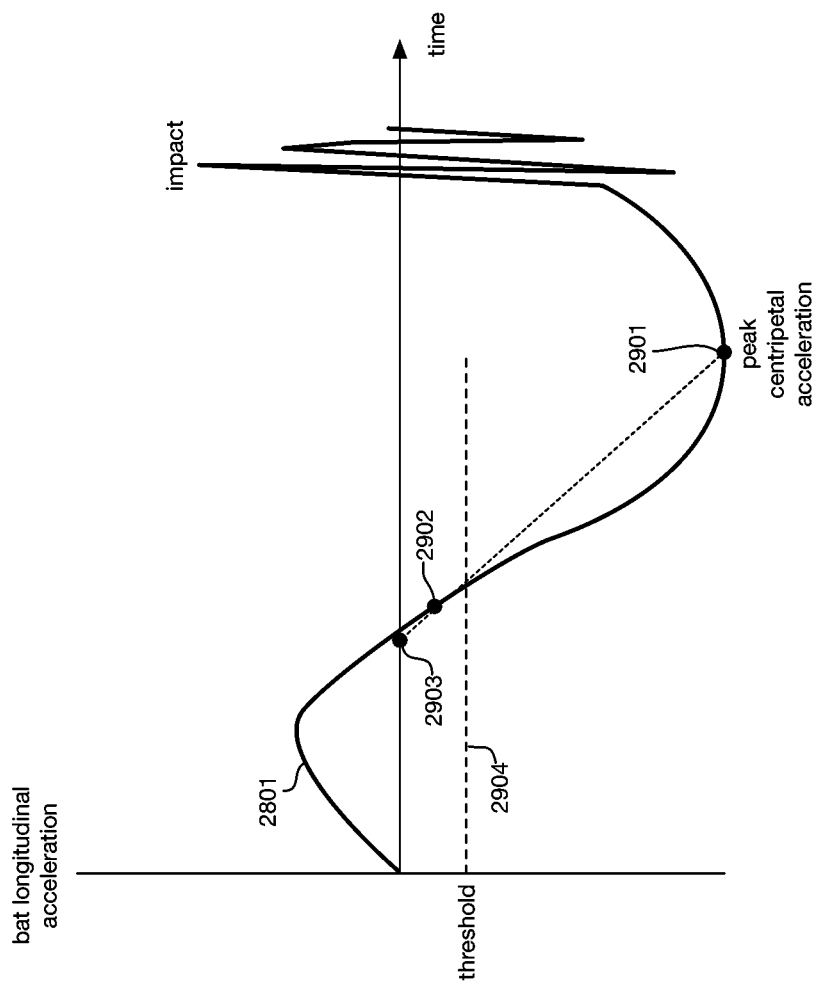
FIG. 29 illustrates a method that may be used in one or more embodiments to determine the start of the centripetal acceleration phase.

One or more embodiments may define a start of a centripetal acceleration phase in any desired manner, including but not limited to defining it as a zero crossing such as point 2803 in FIG. 28. In one or more embodiments, the start of centripetal acceleration event may be determined based on a model of the rotational patterns of a swing. FIG. 29 illustrates a technique for defining the start of centripetal acceleration that may be used in one or more embodiments. A threshold 2904 may be defined to locate points on longitudinal acceleration curve 2801 that are relatively small compared to the peak centripetal acceleration 2901. For example, the threshold may be set to 10% of the peak centripetal acceleration. For every sample starting at this threshold value and working backwards in time, a straight line may be fit through the peak centripetal acceleration point 2901 and the sample. The time when this line crosses zero acceleration may be used as an estimate of the start of centripetal acceleration. This is illustrated in FIG. 29 for sample 2902; the line through points 2901 and 2902 intersects the zero-acceleration axis at time 2903. Point 2903 may therefore be used as an estimate of the start of centripetal acceleration. In one or more embodiments this process may be repeated for different samples working back in time until the acceleration magnitude of the sample is less than a smaller threshold value, such as for example 1% of the peak centripetal acceleration, and the latest time of the intersection of the line through the sample may be used as the start of centripetal acceleration. This procedure may generate a start of centripetal acceleration that is at or near the point in time when the centripetal acceleration changes sign.

Figure 30:
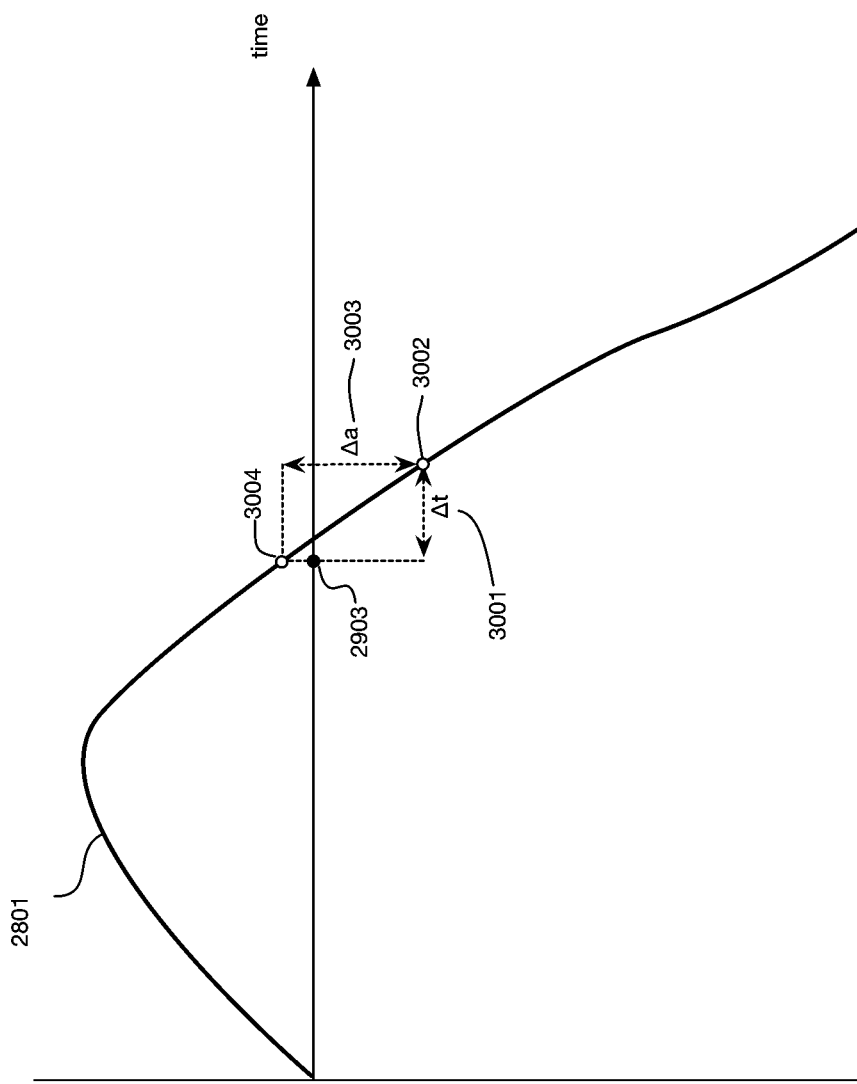
FIG. 30 illustrates a method of calculating a rotational acceleration swing quality metric as a change in acceleration a short time after the beginning of the centripetal acceleration phase.

Having identified a start of centripetal acceleration event, one or more embodiments may calculate a rotational acceleration swing quality metric by measuring the centripetal acceleration at a specific time offset after this event. This calculation is illustrated in FIG. 30. A time interval 3001 is fixed, and the point 3002 on centripetal acceleration curve 2801 is located at this time interval after the start of centripetal acceleration 2903. The acceleration difference 3003 between the centripetal acceleration at 3002 and the centripetal acceleration at time 2903 may be used as a rotational acceleration metric. The time interval 3001 may be fixed so that comparisons of rotational acceleration across players measure how rapidly each player is able to accelerate the swing over a common period of time.

This rotational acceleration metric 3003 is a measure of how the hitter accelerates the bat into rotation. In one or more embodiments, it may be measured early in the rotational phase of the swing to capture information about the coordination and control patterns of the athlete; measuring early in the swing may make this metric less susceptible to swing differences based on pitch location. For example, the time interval 3001 may be selected, without limitation, in a range between 10 and 50 milliseconds, inclusive.

Rotational acceleration is a useful metric to separate hitters between levels. Hitters with high rotational acceleration exhibit high-level movement patterns and proper sequencing of segments through the swing. This is due in large part because it is simply not possible to achieve high values of rotational acceleration without utilizing proper sequencing to accelerate the bat into rotation. A high magnitude of rotational acceleration is the result of proper timing and sequencing of bat load as aggressive body rotation pulls the bat down into rotation. The higher the magnitude, the more functionally proficient the player is in accelerating the bat into a rotational path in a more dynamically adjustable swing. At elite levels, quickly and efficiently generating energy that can be transferred through the kinetic chain is essential to be a successful hitter, given the incredibly dynamic and variable nature of the task.

Figure 31:
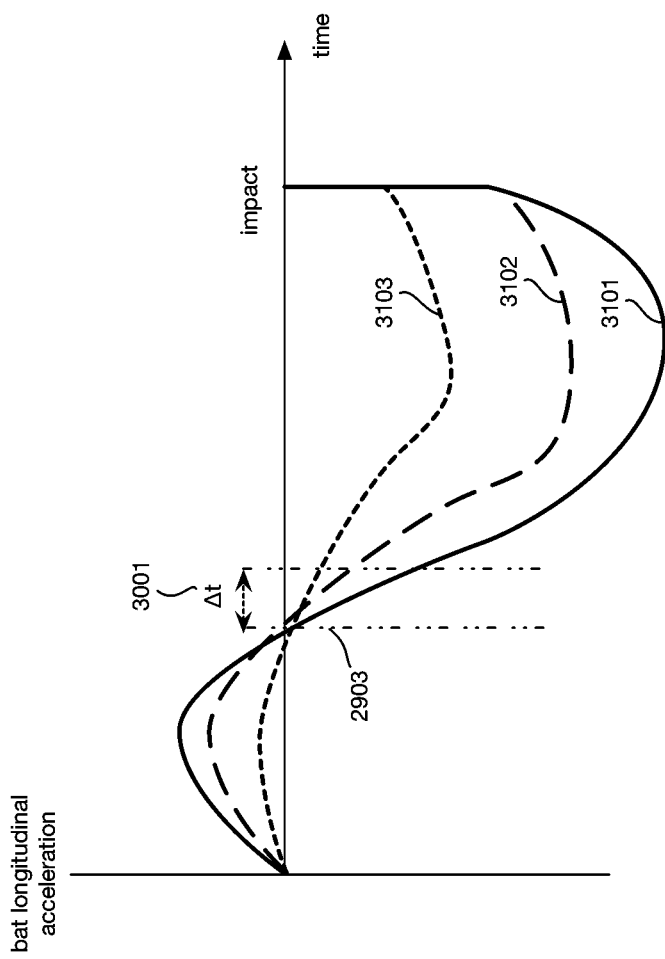
FIG. 31 shows illustrative rotational acceleration for three types of swings.

FIG. 31 shows three illustrative swings 3101, 3102, and 3103. Swing 3101 is from a power hitter who achieves early torso rotation. Swing 3102 is from a player who rotates the body less early in the swing, and therefore achieves less power. Swing 3103 is from a player who primarily uses the arms and hands rather than the body, and therefore has very little hitting power.

The major league baseball average for rotational acceleration is approximately 17 g's. Elite hitters are consistently in the mid 20 g's with some hitters reaching the 30 g's. Hitters with average rotational acceleration values are often "block rotators", that initiate rotation with the hips and shoulders simultaneously. Hitters with low rotational acceleration are commonly hand-dominant hitters who pull the knob of the bat with their upper body to initiate the swing.

Figure 32:
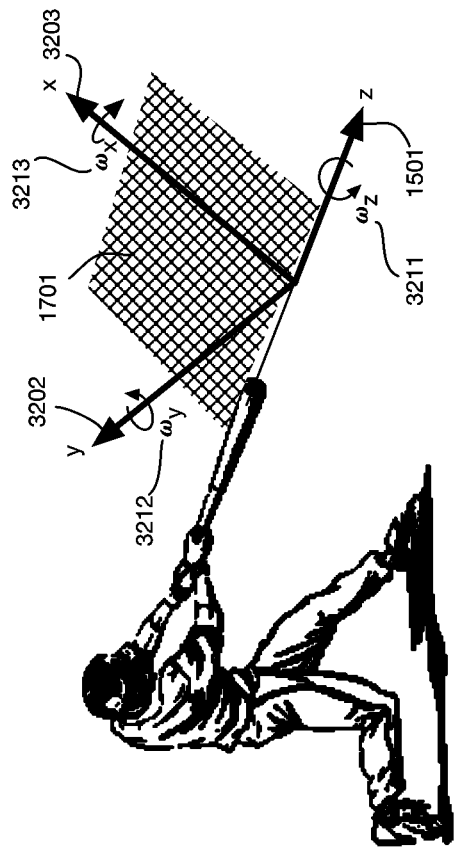
FIG. 32 shows a coordinate system defined using the swing plane, and angular velocities along the coordinate axes of this coordinate system.

Turning now to a second swing quality metric, on-plane efficiency, FIG. 32 shows swing plane 1701 and a coordinate system that may be defined with respect to the swing plane. This coordinate system consists of a z-axis 1501 along the longitudinal axis of the bat, a y-axis 3202 normal (perpendicular) to swing plane 1701, and an x-axis 3203 orthogonal to the y and z axes. (The labels x, y, and z for these axes are arbitrary; one or more embodiments may use any names or labels for any axes.) On-plane efficiency measures how much of the rotation of the bat is around the y-axis 3202. Rotation around other axes does not contribute to the velocity at impact, which lies in the swing plane 1701. Therefore, a higher degree of on-plane efficiency reflects a more efficient swing.

Angular velocity data from the inertial sensor on the bat may be transformed into the coordinate system of FIG. 32. This transformation results in three components of angular velocity: the y-axis angular velocity 3212, which is the primary contributor to swing efficiency, the x-axis angular velocity 3213, and the z-axis angular velocity 3211. The z-axis angular velocity 3211 is bat roll along the longitudinal axis of the bat, which is not a major factor in swing efficiency; however, a large amount of x-axis angular velocity 3213 may reflect an inefficient swing.

Figure 33B:
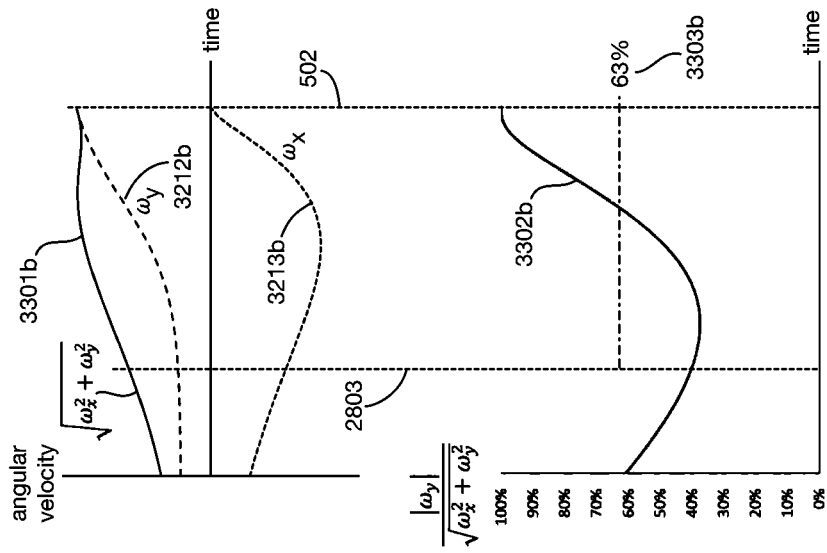
FIGS. 33A and 33B show illustrative calculations of an on-plane efficiency swing quality metric for two types of swings, one with a high value of on-plane efficiency and the other with a relative low value of on-plane efficiency.
Figure 33A:
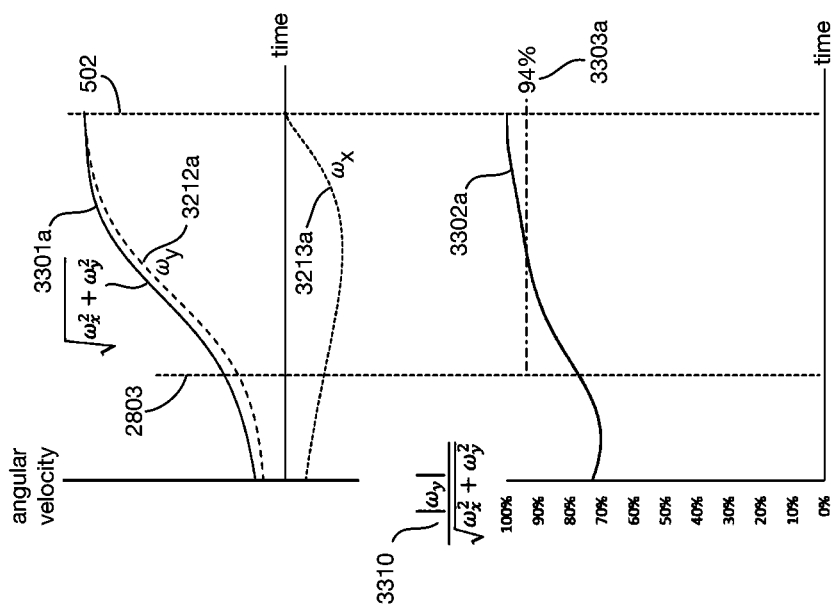

In one or more embodiments, a rotation-on-plane ratio may be calculated at any point in time during the swing as the ratio of the magnitude of the y-axis angular velocity 3212 to the magnitude of the vector sum of x-axis angular velocity 3213 and y-axis angular velocity 3212. This ratio is 100% for pure rotation around axis 3202; as more off-plane rotation occurs around axis 3203, the ratio decreases. (Angular velocity 3211 around the z-axis is ignored in this analysis because it is typically a minor factor.) An on-plane efficiency metric may be calculated as the value of this rotation-on-plane ratio at a point in time, or as an average over a period of time. In one or more embodiments, the on-plane efficiency metric may be calculated as an average of the rotation-on-plane ratio between the start of centripetal acceleration and impact. This method is illustrated in FIGS. 33A and 33B, which show x-axis and y-axis angular velocity for two illustrative swings. Curves 3212a and 3212b show y-axis angular velocity for the two swings; curves 3213a and 3213b show x-axis angular velocity for the two swings, and curves 3301a and 3301b show the magnitude of the vector sum of the x-axis and y-axis angular velocities for the two swings. Curves 3302a and 3302b show the rotation-on-plane ratio 3310 over time for the two swings. The values of the rotation-on-plane ratios are averaged across the time interval 2803 (start of centripetal acceleration) to 502 (impact), giving average values 3303a and 3303b for the two swings. The swing of FIG. 33A has a higher on-plane efficiency swing quality metric, since the y-axis angular velocity 3212a is a relatively larger fraction of the total xy angular velocity 3301a than the corresponding ratio for 3212b and 3301b.

On-plane efficiency measures how early a swing gets on plane and how well it stays on plane as it approaches impact. In an efficient swing, the hitter wants to build as much forward bat speed on plane as possible, to maximize functional bat speed at impact. Swinging the bat on plane is one of the most important skills necessary to becoming a high-level hitter. It is also one of the most variable swing components when comparing hitters. An efficient swing is one in which the hitter gets the barrel on plane very early and deep in the swing path, which allows them to better optimize acceleration of the barrel through the zone. Deviations from the swing plane are the direct result of changes in arm and wrist kinematics relative to the body rotations. The better the hitter is at minimizing these variable arm/wrist degrees of freedom, the longer the hitter's bat will be on plane. In a connected swing, the hitter will read the pitch early and make adjustments through the core and the body instead of the arms and wrist in order to align the swing plane with the pitch location. A good functional swing will have an average on-plane efficiency starting at 70% or higher. A typical dynamic range for on-plane efficiency is 65%-85%. Moving the on-plane efficiency metric higher is desired and directly indicative of a more connected swing.

Figure 34:
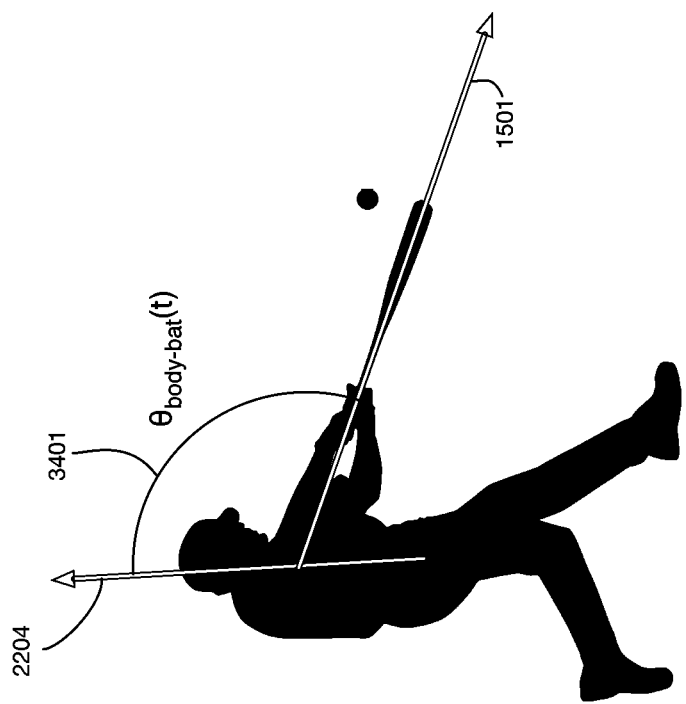
FIG. 34 shows an illustrative definition of a body-bat connection metric using the bat direction and the body tilt axis.

Turning now to the body-bat connection swing quality metric, this metric measures the relationship between the hitter's body and the bat. Ideally this relationship is approximately perpendicular throughout the rotational portion of the swing. FIG. 34 illustrates a definition of body-bat connection that may be used in one or more embodiments. The body tilt axis 2204 may be defined from three points on the trajectory of the hands, as discussed above with respect to FIGS. 19 and 22. This axis 2204 is calculated as a single axis for the entire swing. The bat longitudinal axis 1501 moves through the swing; therefore, the angle 3401 between the body axis 2204 and the bat axis 1501 is a function of time. This angle 3401 may be used as the body-bat connection metric at that point in time, with an ideal value of 90°.

Figure 35B:
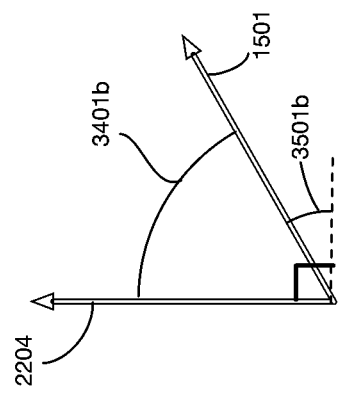
FIGS. 35A and 35B show illustrative calculations of a disconnection metric, which is the offset between the connection metric and 90 degrees.
Figure 35A:
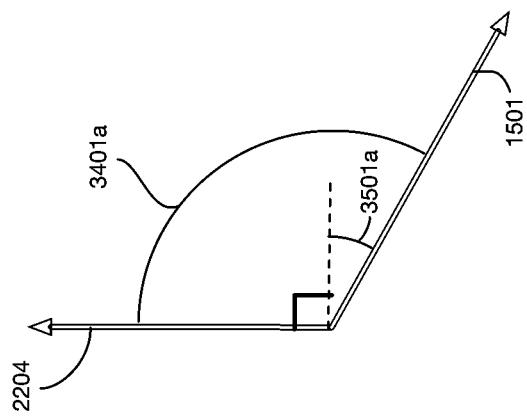

In one or more embodiments it may also be useful to calculate a disconnection metric, which is the complement of connection (the absolute value of the difference between the body-bat connection angle and 90°). Disconnection is illustrated in FIGS. 35A and 35B. In FIG. 35A, the connection angle 3401a is greater than 90°, and the disconnection angle 3501a is angle 3401 less 90°. In FIG. 35B the connection angle 3401b is below 90°, and the disconnection angle 3501b is 90° less angle 3401b. Use of disconnection instead of connection may be more useful when averaging or integrating connection angles over time, since use of absolute differences prevents a negative difference at one point in time from compensating for a positive difference at a different point in time.

Figure 36:
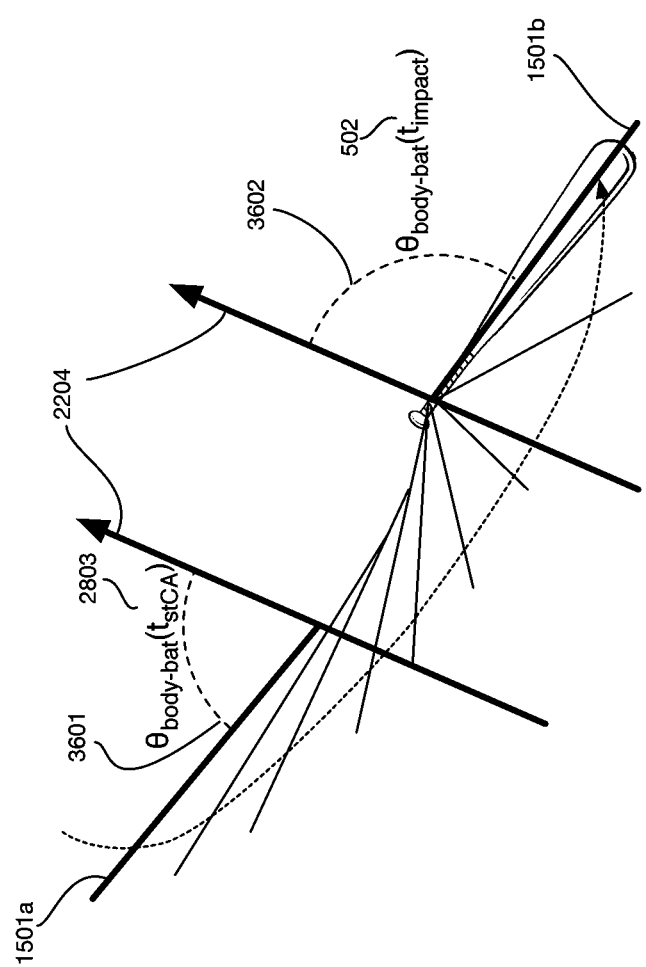
FIG. 36 shows illustrative body-bat connection values at the start of centripetal acceleration and at impact.

As illustrated in FIG. 36, one or more embodiments may measure the body-bat connection (and/or disconnection) at the point of impact 502 and at the start of centripetal acceleration 2803. The angle 3601 between the axis 2204 and the bat axis 1501a may be referred to as the early connection or connection-early, and the angle 3602 between axis 2204 and bat axis 1501b at impact may be referred to as the connection-at-impact. The connection-early and connection-at-impact values may be averaged to generate an overall body-bat connection metric, or equivalently the disconnection-early and disconnection-at-impact values may be averaged to generate an average body-bat disconnection metric.

Connection is important measure of the athlete's ability to dynamically adjust for different pitch types and locations, as well as executing consistent mechanics swing to swing. Connection and the relationship between early connection and connection-at-impact is also highly related to on-plane efficiency. In a good functional swing, the hitter adjusts to different pitch locations using their body tilt, keeping their connection values consistent. Hitters who adjust to different pitch locations by manipulating the barrel with their hands will have variable connection values across pitch locations. This introduces additional degrees of freedom at the wrist into the swing that are difficult to control and execute with consistency.

The typical range for major league baseball players for connection-at-impact is 80°-95°. Values for connection-early are typically in the range of 75°-130°. High connection-early values (110° and greater) typically indicate a very steep vertical bat angle as the hitter begins to rotate. Hitters with connection-early values 110° and greater will either need to correct their connection quickly as they begin to rotate, or they will have poor on-plane efficiency values. Connection values ideally will not change based on pitch location and will be consistently near 90° for all vertical bat angles. However, variable connection is common for hitters who manipulate the barrel with their hands. The bat axis orientation will change based on pitch location and the hitter should adjust their body tilt to match that change.

Figure 37:
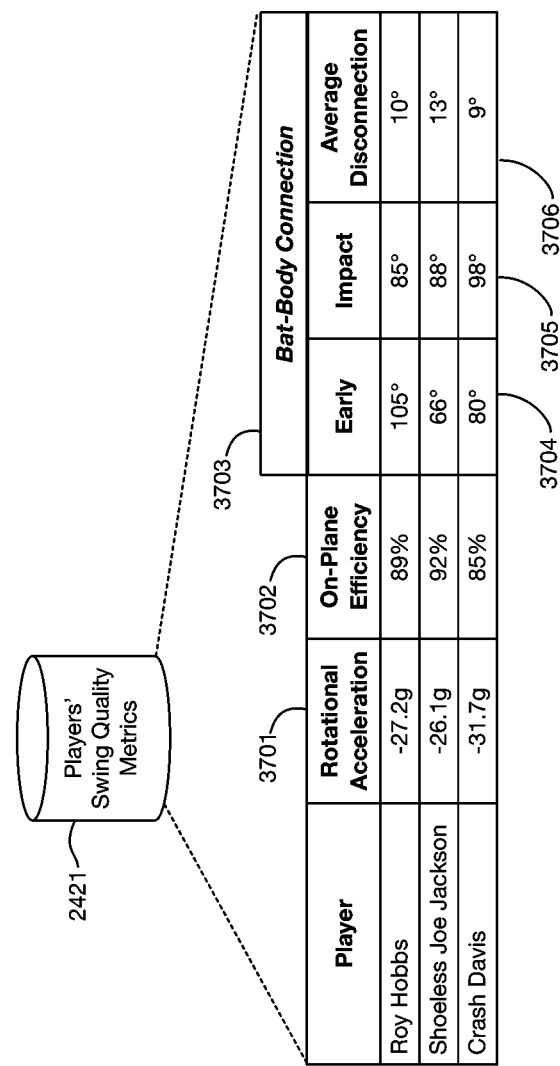
FIG. 37 shows illustrative values for three swing quality metrics—rotational acceleration, on-plane efficiency, and body-bat connection—for three players.

FIG. 37 shows the three illustrative swing quality metrics for hypothetical swings by three players. These metrics may be stored for example in database 2421. The rotational acceleration 3701 and on-plane efficiency 3702 are calculated as described above. For bat-body connection 3703, three values are shown: the early connection 3704, the connection-at-impact 3705, and the average disconnection 3706.

In one or more embodiments of the invention, analysis of a swing may include calculation of a rotational profile for the swing. This rotational profile may be calculated from sensor data captured by a sensor attached to or integrated into a piece of equipment that is moved by a user, such as a baseball bat or a golf club. The illustrative examples described below show calculation of a rotational profile for a baseball swing, but one or more embodiments may calculate a similar rotational profile for any type of motion of a piece of equipment such as a softball bat, cricket bat, tennis racket, golf club, hockey stick, or other equipment used in any type of activity.

The rotational profile as described below may provide information to answer questions such as the following: How well does the user load? How quickly can the user accelerate? What is the user's peak force? How much force does the user produce over the swing? How long does it take for the user to produce that force? How well does the user sequence? How do users compare?

Figure 38:
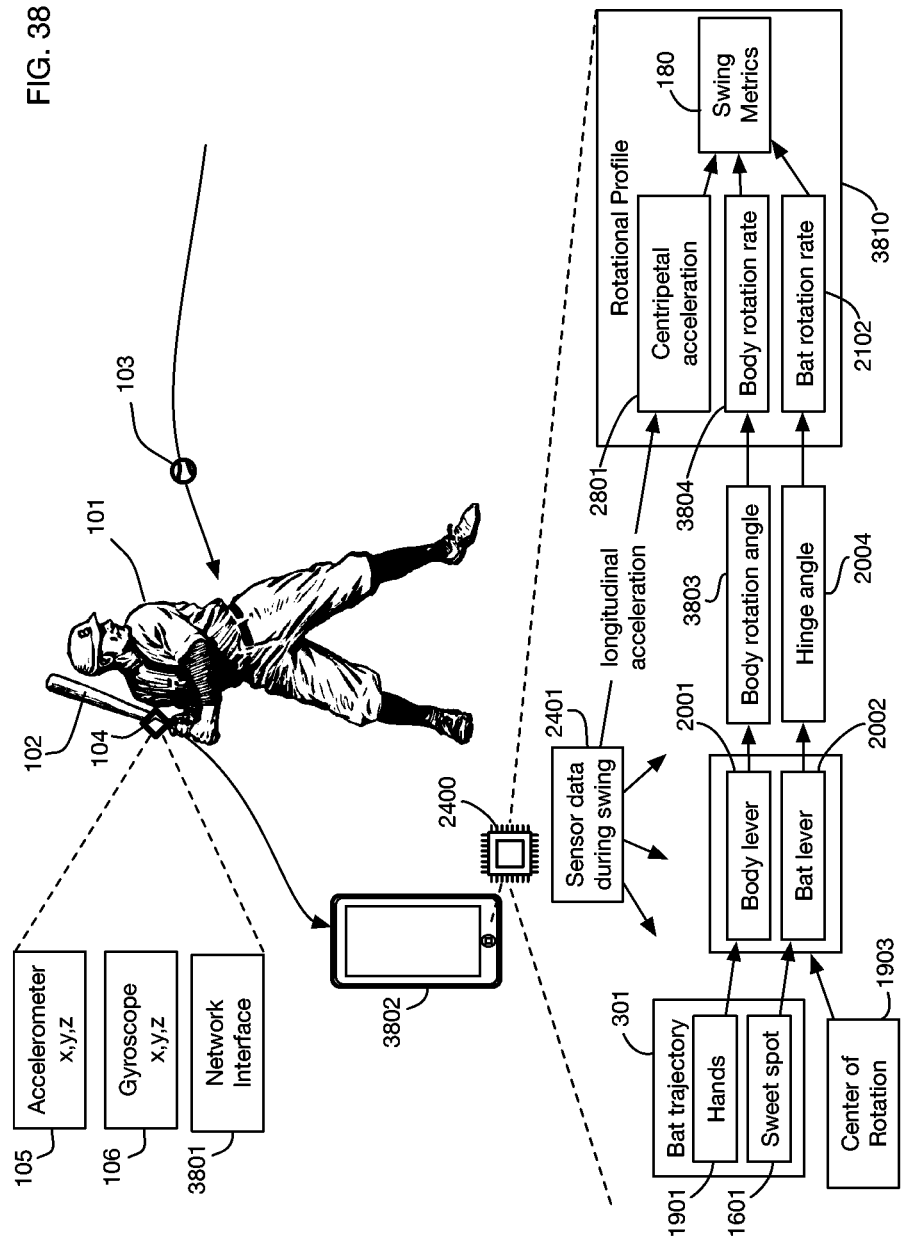
FIG. 38 shows an illustrative swing analysis system that calculates a rotational profile from data obtained from an inertial sensor on the bat.

FIG. 38 illustrates calculation of a rotational profile 3810 for a swing of bat 102 by user 101 to hit ball 103. The bat may have one or more sensors 104, which may include for example inertial motion sensors such as 3-axis accelerometer 105 and 3-axis rate gyroscope 106. Sensor(s) 104 may also include or be attached to a network interface 3801. In one or more embodiments, the sensor device may include a processor and a memory. Data captured by sensors 105 and 106 during a swing may be transmitted to a processor 2400 over a network connection (which may be wired or wireless) for analysis. The processor may for example be installed in a mobile device 3802, such as a smartphone. In one or more embodiments, processor 2400 may be a network of processors; for example, mobile device 3802 may forward data to one or more servers for all or part of the analysis.

FIG. 38 shows illustrative calculation steps that may be performed by processor(s) 2400 to obtain rotational profile 3810 for a swing. The sensor data 2401 captured during the swing may be analyzed in several stages. A bat trajectory 301 may be calculated, as described above for example with respect to FIG. 1. This trajectory may include the position and velocity of points on the bat at a sequence of times during the swing. Specific points on the bat that may be of interest may include the position 1901 of the hands on the bat and the position 1601 of the sweet spot (which may be selected as any convenient location on the bat that is away from the hands, towards the barrel end of the bat for example). As described above with respect to FIG. 19, a center of rotation 1903 may also be calculated for the swing.

As described above with respect to FIG. 20, using the center of rotation 1903 and the position 1901 of the hands and position 1601 of the sweet spot, the swing may be analyzed using a two-lever model that treats the motion of the bat as resulting from rotation of body lever 2001 between the center of rotation and the hands, and rotation of the bat lever 2002 between the hands and the sweet spot. Motion of each of these two levers may be analyzed separately, which provides insight into the rotational profile of the swing. For example, in an effective swing, the user typically begins with body rotation and then later in the swing the user releases the wrists to move the bat lever so that the bat contacts the ball with high velocity.

The body lever 2001 and the bat lever 2002 rotate throughout the swing, as illustrated for example in FIG. 19. A body rotation angle 3803 may be calculated at each point in time as the angle between the body lever at that time and the initial body lever at the start of the swing. A hinge angle 2004 may be calculated at each point in time based on the relative orientation of the bat lever and the body lever at that time; for example, as shown in FIG. 20, the hinge angle 2004 may be calculated as the angle between the perpendicular 2003 to the body lever 2001 and the bat lever 2002. In one or more embodiments, the body rotation angle and the hinge angle may be calculated in the swing plane; for example, the body lever and bat lever may be first projected onto the swing plane and the angles may be calculated based on these projected levers.

The time rates of change of these angles 3803 and 2004 may form part of the rotational profile 3810. The body rotation rate 3804 at a point in time may be calculated as the instantaneous rate of change (the time derivative) of the body rotation angle 3803, and the bat rotation rate 2102 may be calculated as the instantaneous rate of change of the hinge angle 2004. In one or more embodiments the bat rotation rate may be calculated as the rate of change of the absolute angle of the bat lever, rather than of the relative angle between the bat lever and the body lever.

In one or more embodiments, the rotational profile 3810 may also include the centripetal acceleration 2801 of the bat at each point in time, measured along the bat's longitudinal axis 1501, as illustrated for example in FIG. 28. This longitudinal axis may for example correspond to one of the axes of the accelerometer on the bat, or the acceleration vector may be projected onto this axis to calculate the centripetal acceleration. Centripetal acceleration may be oriented so that it is positive when the acceleration is towards the tip of the bat, and negative when the acceleration is towards the knob of the bat.

One or more embodiments of the invention may also include one or more swing metrics 180 in the rotational profile 3810. These metrics 180 may be calculated from sensor data 2401 or from any of the derived values shown in FIG. 38 or elsewhere in this application. They may include any of the metrics described above. Some illustrative additional metrics that may be calculated from the rotational profile curves 2801, 3804 and 2102 are described below.

Figure 39A:
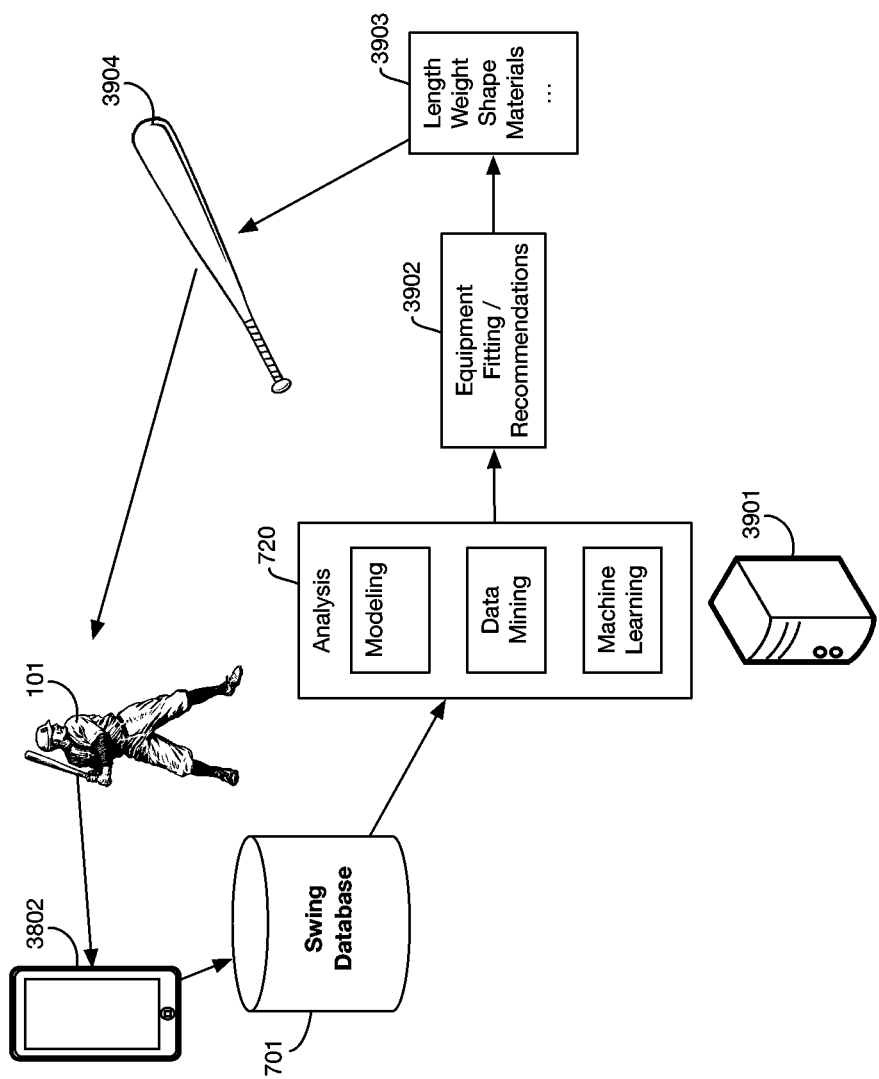
FIG. 39A illustrates use of rotational profile data or other swing analysis data to recommend equipment or to fit equipment for a user.

As described above with respect to FIG. 7, in one or more embodiments the sensor data and derived values calculated from this data may be stored in a swing database 701. This database may contain values from swings by multiple users, and analyses 720 may be performed on the data to compare and evaluate users' swing performance. As shown in FIG. 39A, these analyses may be performed by a computer (or network of computers) 3901. In addition to the analyses illustrated in FIG. 7, analyses 720 may generate equipment fitting or equipment recommendation analyses 3902 for the user 101. For example, these recommendations may include values 3903 such as the recommended length, weight, shape, or materials of a bat, or a recommended specific model 3904. These recommendations may for example be transmitted to mobile device 3802 associated with user 101. The user 101 may for example take one or more swings, and sensor data transmitted to mobile device 3802 may be forwarded to swing database 701 for storage or analysis; equipment recommendations may then be sent back to the mobile device 3802 shortly thereafter so that the user receives immediate advice on optimal equipment. FIG. 39B shows another illustrative application of the analysis and fitting system of FIG. 39A. User 101 may take swings with multiple equipment options, such as bats 3910a, 3910b, and 3910c, to determine which of these options functions best for that user. Sensor data collected from each of these bat options may be collected by device 3802 and analyzed by processor 3901. For example, this analysis may generate a comparison table 3920 that shows swing metrics 3921, 3922, and 3923 for swings from each of the bats 3910a, 3910b, and 3910c. In one or more embodiments, any number of equipment options may be compared using any number of metrics. In this illustrative example, the reported metrics include bat swing speed at impact 3921, the time of the swing (between start of swing and contact) 3922, and the acceleration impulse 4305 (which is calculated from the rotational acceleration curve of the rotational profile, and is described below with respect to FIG. 43). Metrics may include for example any values derived from acceleration or gyro data, or from the rotational profile. Table 3920 also includes a combined score 3924 for each bat, which may for example be a weighted sum (or any other function) of the metrics 3921, 3922, and 3923. Bat 3910b has the highest combined score 3930, so this bat may be recommended to user 101. In one or more embodiments, users may be able to select one or more metrics that are most important, assign weights, and compare bat rankings on this basis.

FIG. 40 shows elements of an illustrative rotational profile 3810a, including centripetal acceleration 2801a, body rotation rate 3804a, and bat rotation rate 2102a. Each of these elements is a sequence of values over time throughout the swing, shown in FIG. 40 as corresponding graphs with the time axis 4001 normalized to a fraction of the total swing duration. The shape of these curves may provide insights into the quality of the swing, and differences in curves across players may help differentiate player performance and skill level. For example, FIG. 41A shows centripetal acceleration curves for swings from players of five different skill levels. Curve 4101 is from a US Major League Baseball (MLB) "power hitter"; the peak (negative) centripetal acceleration of this player is lower (more negative) than the corresponding peak for the other players. Curve 4102 is from an MLB all-star. Curve 4103 is from an MLB top prospect. The curves with the highest (least negative) peak centripetal acceleration are curve 4104 from a player with a high strikeout rate, and curve 4105 from an MLB drafted player who was not successful. In these examples there is a clear relationship between performance and the centripetal acceleration curve of the rotational profile.

FIG. 41B shows body rotation rate and bat rotation rate curves for swings from players of three different skill levels. These curves provide indicators of how well the different players sequence their motions through the swing. Ideally the body should rotate first, with minimal change to the hinge angle, and then the bat should be released for a rapid change in the hinge angle. Profile 4110d shows a player with minimal bat-body sequencing; the bat rotation rate 2102d increases from the start along with the body rotation rate 3804d. Profile 4110e shows a player with moderate bat-body sequencing, and profile 4110f shows a player with excellent bat-body sequencing. The inventors have found that proper sequencing, as revealed by these rotational profile curves, is closely correlated with higher (more negative) values for centripetal acceleration as the player is effectively using the body to accelerate the bat as opposed to initiating the swing with hand motion towards the ball or wrist motions. For example, the average rotational acceleration through the swing of 4110d is 8.6 g, the average rotational acceleration through the swing of 4110e is 13.1 g, and the average rotational acceleration through the swing of 4110f is 21.2 g, showing that the last player develops more power via excellent sequencing.

In one or more embodiments of the invention, analysis of swing data may include partitioning the swing into phases. The timing of theses phases may provide insight into how a user sequences the different actions that constitute a complete swing. For example, in an efficient swing the batter successively rotates the lower body, the upper body, and then the bat.

Illustrative phases are shown in FIG. 42 for a swing with centripetal acceleration curve 2801a. (Phases may be calculated based on any sensor data or derived data, including but not limited to the centripetal acceleration.) A start of swing time 4201 may be defined or calculated, as well as an end of swing time 4202 (which may for example correspond to impact between the bat and the ball). Between the start 4201 and end 4202, four swing phases 4211, 4212, 4213, and 4214 may be calculated. The load phase 4211 may start at the start of swing 4201 and may end for example at point 4203 when centripetal acceleration 2801a crosses the zero axis and changes from a positive value to a negative value. The accelerate phase 4212 follows the load phase, and is the phase when centripetal acceleration changes rapidly. The peak phase 4213 follows the accelerate phase, and corresponds to the bat unhinging from the body and accelerating from the body. The transfer phase 4214 follows the peak phase and continues to the end of swing 4202.

FIGS. 43 and 44 show illustrative swing metrics that may be calculated from the centripetal acceleration and rotational rate curves, and from the phases illustrated above in FIG. 42. One or more embodiments of the invention may calculate any desired metrics from this data or from any of the sensor data or other derived quantities. FIG. 43 shows five illustrative metrics 4301, 4302, 4303, 4304, and 4305 that may be calculated from the centripetal acceleration curve 2801a. The peak loading acceleration 4301 may be calculated as the acceleration value at the peak (positive) maximum point 4311 in the load phase. For the accelerate phase, the rate of acceleration metric 4302 may be calculated as the slope of the line segment between point 4203 at the start of the acceleration phase and the point 4312 at the end of the acceleration phase; this value 4302 also equals the average rate of change of centripetal acceleration over the accelerate phase. In the peak phase, the peak acceleration metric 4303 may be calculated as the acceleration value at the minimum (most negative) point 4313, and the time to peak force metric 4304 may be calculated as the time difference between the start of the accelerate phase and the time at the minimum point 4313. A smaller time to peak force may give a player more time to react to an incoming pitch. The acceleration impulse metric 4305 may be calculated as the integral of the centripetal acceleration curve across the accelerate, peak, and transfer phases; this integral corresponds to the shaded area shown in FIG. 43. This acceleration impulse metric may for example be correlated with the total centripetal force produced during the downswing.

FIG. 44 shows three illustrative metrics 4401, 4402, and 4403 that may be calculated from the body rotation rate 3804b and the bat rotation rate 2102b. The peak body rotation rate 4401 may be calculated as the maximum value during the swing of the body rotation rate, and the peak bat rotation rate 4402 may be calculated as the maximum value during the swing of the bat rotation rate. The rotation rate ratio 4403 may be calculated as the ratio of the peak bat rotation rate 4402 to the peak body rotation rate 4401. One or more embodiments may include additional metrics calculated from the rotation rates, such as metrics that combine sequencing, timing, and peak data into a quality score, and metrics that measure stability and balance.

The discussion above focuses primarily on the example of a baseball bat swing to illustrate calculation and use of a rotational profile for a piece of equipment moved by a user. In one or more embodiments, the same or similar features may be applied to movement of other types of equipment, such as equipment used for other sports. The terms "bat trajectory", "bat lever", "bat rotation rate", "peak bat rotation rate", etc. may be interpreted in one or more embodiments of the invention as "equipment trajectory", "equipment lever", "equipment rotation rate", "peak equipment rotation rate" and so forth, for any type of equipment.

For many sports, a "swing" or other movement of a piece of equipment may be analyzed using a two-lever model similar to the model described above for a baseball swing. This two-lever model may be used for example for equipment that is held by a user and that has a portion of the equipment (which may be called the "sweet spot") that may strike or contact a ball or other object. The "body lever" may extend from a center of rotation (which may be a point on the user's body) to the position of the hands on the equipment. The "equipment lever" may extend from the hand position to the sweet spot. The motion of the equipment may be viewed as a combination of a rotation of the body lever around the center of rotation, and a rotation of the equipment lever relative to the body lever at the joint of the hands. A rotational profile and various metrics may be calculated for this equipment motion using the devices and techniques described above for a baseball bat swing.

FIG. 45 shows an example of calculating a rotational profile for a golf swing. Like the baseball swing examples described above, this example illustrates a general technique that may be used for any type of equipment. In this embodiment of the invention, an inertial sensor may be attached to a golf club to collect data when user 4501 swings the club. Data may be transferred to and analyzed by one or more processors, as shown for example in FIG. 38; this data may be stored in a database and used for fitting or other analyses, as shown for example in FIGS. 39A and 39B.

A two-lever model may be used to analyze the golf swing shown in FIG. 45 with procedures that are similar to those described above for a baseball bat swing. A center of rotation 4504 may be calculated for all or a portion of the swing. A body lever 4507 may extend from the center of rotation 4504 to the hand position 4503 on the golf club, and a club lever (a type of equipment lever) 4506 may extend from the hand position 4503 to the sweet spot (on the club face) 4502 of the club, which may be for example any spot on the club that may be used to strike the golf ball. The center of rotation 4504 may for example be calculated using three points 4511, 4512, and 4513 on the trajectory of the sweet spot, by locating the point coplanar with these three points and equidistant from each point; this method is analogous to the method shown in FIG. 19 for a baseball bat swing.

In one or more embodiments of the invention, motion of a piece of equipment may be analyzed in stages. For example, for the swing of the golf club shown in FIG. 45, path 4510 shows the trajectory of the sweet spot of the club in the downswing, and a different path 4514 shows the trajectory of the sweet spot during the backswing. The downswing and backswing may therefore have different centers of rotation 4504 and 4515, respectively. Physically this may correspond for example to a weight shift to the front foot and forward translation of the golfer's center of mass that may occur during the first half of the downswing. Illustrative points on the downswing trajectory that may be used to calculate center of rotation 4504 may be the point at impact, the point at 75% of the time from the start of the downswing to impact, and the point at 87.5% of the time from the start of downswing to impact. The start of downswing may be defined for example as the point where the magnitude of the angular velocity of the clubhead along the plane perpendicular to the club's longitudinal axis is at a minimum. For the backswing, illustrative points to determine center of rotation 4515 may for example include the point of peak clubhead angular velocity (along the plane perpendicular to the longitudinal axis), the point halfway (by time) between the start of backswing and this peak angular velocity point, and the point halfway (by time) between the peak angular velocity point and the start of the backswing.

A rotational profile 4520 and various swing metrics 4524 may be calculated for a golf swing in a manner analogous to that described above for a baseball swing. For example, rotational profile 4520 may include the curve 4521 of centripetal acceleration along the golf club longitudinal axis (along the shaft), body rotation rate curve 4522 for the rate of change of the angle of body lever 4507, and equipment (club) rotation rate curve 4523 for the rate of change of the "hinge angle" between body lever 4507 and equipment (club) lever 4506. Metrics 4524 may be calculated from the rotation profile 4520 or from any sensor data; illustrative metrics that may be used for golf may include for example, without limitation, the peak body rotation rate, the peak equipment (club) rotation rate, and the rotation rate ratio, defined for golf as in FIG. 44 for baseball.

While the ideas herein disclosed has been described by means of specific embodiments and applications thereof, numerous modifications and variations could be made thereto by those skilled in the art without departing from the scope of the invention set forth in the claims.

What is claimed is:

1. A swing analysis system that calculates a rotational profile, comprising:
   an inertial sensor comprising
      an accelerometer;
      a gyroscope; and
      a network interface;
         wherein
            said inertial sensor is coupled to equipment;
            said equipment is associated with a longitudinal axis;
            said equipment comprises
               a hand position; and
               a sweet spot position;
            said inertial sensor is configured to capture inertial sensor data at a sequence of times during a swing of said equipment by a user;
   a processor coupled to said inertial sensor via a network connection, wherein said processor is configured to
      receive said inertial sensor data; and
      based on said inertial sensor data, calculate
         a trajectory of said equipment comprising
            said hand position at said sequence of times; and
            said sweet spot position at said sequence of times;
         a center of rotation of said swing;
         a body lever at said sequence of times that extends from said center of rotation to said hand position;
         an equipment lever at said sequence of times that extends from said hand position to said sweet spot position;
         a body rotation angle at said sequence of times, comprising an angle between said equipment lever and a starting equipment lever at a start of said swing;
         a hinge angle at said sequence of times, comprising an angle between said equipment lever and a tangent perpendicular to said body lever;
         a body rotation rate at said sequence of times, comprising a rate of change of said body rotation angle;
         an equipment rotation rate at said sequence of times, comprising a rate of change of said hinge angle;
         a centripetal acceleration of said equipment along said longitudinal axis at said sequence of times; and,
         a rotational profile comprising
            said body rotation rate at said sequence of times;
            said equipment rotation rate at said sequence of times; and,
            said centripetal acceleration at said sequence of times.

2. The swing analysis system of claim 1, wherein said equipment comprises a bat.

3. The swing analysis system of claim 1, wherein said equipment comprises a golf club.

4. The swing analysis system of claim 1, further comprising
   a database comprising
      said rotational profile associated with each user of a plurality of users, wherein said plurality of users comprises said user; and,
   wherein said swing analysis system with said database is configured to compare said rotational profile across said plurality of users.

5. The swing analysis system of claim 4, wherein said swing analysis system is further configured to generate recommended equipment for said user.

6. The swing analysis system of claim 5, wherein said generate said recommended equipment for said user comprises
calculate one or more swing metrics for swings by said user of a plurality of equipment options;
calculate a score for each equipment option of said plurality of equipment options from said one or more swing metrics; and,
identify said recommended equipment as an equipment option of said plurality of equipment options with a highest value of said score.

7. The swing analysis system of claim 6, wherein said one or more swing metrics comprise
an equipment swing speed at impact; and,
a swing time to contact.

8. The swing analysis system of claim 7, wherein said one or more swing metrics further comprise one or more addition metrics calculated from said rotational profile.

9. The swing analysis system of claim 1, wherein said processor is further configured to
partition said sequence of times into phases, wherein said phases comprise
a load phase ending when said centripetal acceleration changes from positive to negative;
an accelerate phase following said load phase;
a peak phase following said accelerate phase; and,
a transfer phase following said peak phase and ending at an end of said swing when said equipment impacts a ball.

10. The swing analysis system of claim 9, wherein said rotational profile further comprises one or more swing metrics calculated from one or more of
said inertial sensor data;
said body rotation rate at said sequence of times;
said equipment rotation rate at said sequence of times; and,
said centripetal acceleration at said sequence of times.

11. The swing analysis system of claim 10, wherein said one or more swing metrics comprise
a peak loading acceleration, comprising a maximum positive centripetal acceleration during said load phase.

12. The swing analysis system of claim 10, wherein said one or more swing metrics comprise
a rate of acceleration, said rate of acceleration comprising an average rate of change of said centripetal acceleration during said accelerate phase.

13. The swing analysis system of claim 10, wherein said one or more swing metrics comprise
a peak acceleration, said peak acceleration comprising a minimum negative centripetal acceleration after said load phase and before said end of said swing.

14. The swing analysis system of claim 10, wherein said one or more swing metrics comprise
an acceleration impulse, said acceleration impulse comprising an integral of said centripetal acceleration between a start of said accelerate phase and said end of said swing.

15. The swing analysis system of claim 10, wherein said one or more swing metrics comprise a time to peak force, said time to peak force comprising a time difference between a start of said accelerate phase and a time when said centripetal acceleration reaches a minimum negative value after said start of said accelerate phase.

16. The swing analysis system of claim 10, wherein said one or more swing metrics comprise
a peak equipment rotation rate, said peak equipment rotation rate comprising a maximum value of said equipment rotation rate between a start of said load phase and said end of said swing; and,
a peak body rotation rate, said peak body rotation rate comprising a maximum value of said body rotation rate between a start of said load phase and said end of said swing.

17. The swing analysis system of claim 16, wherein said one or more swing metrics further comprise a ratio between said peak equipment rotation rate and said peak body rotation rate.

18. The swing analysis system of claim 10, wherein said one or more swing metrics comprise
a peak loading acceleration, said peak loading acceleration comprising a maximum positive centripetal acceleration during said load phase;
a rate of acceleration, said rate of acceleration comprising an average rate of change of said centripetal acceleration during said accelerate phase;
a peak acceleration, said peak acceleration comprising a minimum negative centripetal acceleration after said load phase and before said end of said swing;
an acceleration impulse, said acceleration impulse comprising an integral of said centripetal acceleration between a start of said accelerate phase and said end of said swing;
a time to peak force, said time to peak force comprising a time difference between a start of said accelerate phase and a time when said centripetal acceleration reaches a minimum negative value after said start of said accelerate phase;
a peak equipment rotation rate, said peak equipment rotation rate comprising a maximum value of said equipment rotation rate between a start of said load phase and said end of said swing;
a peak body rotation rate, said peak body rotation rate comprising a maximum value of said body rotation rate between a start of said load phase and said end of said swing; and,
a ratio between said peak equipment rotation rate and said peak body rotation rate.

* * * * *